US009884920B2

(12) United States Patent
Holmes et al.

(10) Patent No.: US 9,884,920 B2
(45) Date of Patent: Feb. 6, 2018

(54) ANTIBODIES SPECIFIC FOR 4,6-DIAMINO-5-(FORMAMIDO)PYRIMIDINE AND USES THEREOF

(71) Applicant: FLORIDA STATE UNIVERSITY RESEARCH FOUNDATION, INC., Tallahassee, FL (US)

(72) Inventors: Eric Holmes, Tallahassee, FL (US); Gary Ostrander, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 0 days.

(21) Appl. No.: 15/289,783

(22) Filed: Oct. 10, 2016

(65) Prior Publication Data

US 2017/0101481 A1 Apr. 13, 2017

Related U.S. Application Data

(60) Provisional application No. 62/239,686, filed on Oct. 9, 2015.

(51) Int. Cl.
*C07K 16/44* (2006.01)
*A61K 47/48* (2006.01)
*G01N 33/53* (2006.01)
*G01N 33/574* (2006.01)

(52) U.S. Cl.
CPC ......... *C07K 16/44* (2013.01); *G01N 33/5308* (2013.01); *G01N 33/574* (2013.01); *C07K 2317/14* (2013.01); *C07K 2317/33* (2013.01); *C07K 2317/565* (2013.01)

(58) Field of Classification Search
CPC ... C07K 16/44; G01N 33/5308; G01N 33/574
See application file for complete search history.

(56) References Cited

U.S. PATENT DOCUMENTS

| 6,187,551 | B1 | 2/2001 | Holmes et al. |
| 6,900,291 | B2 * | 5/2005 | Holmes ............ G01N 33/57484 424/193.1 |
| 2003/0186344 | A1 | 10/2003 | Holmes et al. |
| 2007/0269824 | A1 | 11/2007 | Albrecht et al. |
| 2013/0177921 | A1 | 7/2013 | Chastain et al. |

OTHER PUBLICATIONS

Jaruga, P., et al., "Mouse NEIL1 Protein is Specific for Excision of 2,6-Diamino-4-hydroxy-5-formamidopyrimidine and 4,6-Diamino-5-formamidopyrimidine from Oxidatively Damaged DNA," *Biochemistry*, 2004, vol. 43, pp. 15909-15914.
Kryston, T.B., et al., "Role of oxidative stress and DNA damage in human carcinogenesis," *Mutation Research*, 2011, vol. 711, pp. 193-201.
Acharya, A. et al. "Redox regulation in cancer: A double-edged sword with therapeutic potential" *Oxidative Medicine and Cellular Longevity*, 2010, 3:23-34.
Aruoma, O.I. et al. "Damage to the bases in DNA induced by hydrogen peroxide and ferric ion chelates" *J. Biol. Chem.*, 1989, 264:13024-13028.
Aw, T. "Cellular redox: a modulator of intestinal epithelial cell proliferation" *News Physiol Sci.*, 2003, 18:201-204.
Aw, T. "Molecular and cellular responses to oxidative stress and changes in oxidation-reduction imbalance in the intestine" *Am J Clin Nutr.*, 1999, 70:557-565.
Cheng, K.C. et al. "8-Hydroxyguanine, an abundant form of oxidative DNA damage, causes G----T and A----C substitutions" *J Biol Chem.*, 1992, 267:166-172.
Cho, B.P. and Evans, F.E. "Structure of oxidatively damaged nucleic acid adducts. 3. Tautomerism, ionization and protonation of 8-hydroxyadenosine studied by 15N NMR spectroscopy" *Nucleic Acids Research*, 1991, 19(5):1041-1047.
Cho, B.P. et al. "15N nuclear magnetic resonance studies on the tautomerism of 8-hydroxy-2'-deoxyguanosine, 8-hydroxyguanosine, and other C8-substituted guanine nucleosides" *Chem. Res. Toxicol.*, 1990, 3:445-452.
Circu, M.L. and Aw, T. "Reactive oxygen species, cellular redox systems, and apoptosis" *Free Radic Biol Med.*, 2010, 48:749-762.
Dizdaroglu, M. "Application of capillary gas chromatography-mass spectrometry to chemical characterization of radiation-induced base damage of DNA: implications for assessing DNA repair process" *Anal. Biochem.*, 1985, 144:593-603; abstract only.
Dizdaroglu, M. "The use of capillary gas chromatography-mass spectrometry for identification of radiation-induced DNA base damage and DNA base-amino acid cross-links" *J. Chromatog.*, 1984, 295:103-121.
Dizdaroglu, M. and Gajewski, E. "Selected-ion mass spectrometry: assays of oxidative DNA damage" *Methods Enzymol.*, 1990, 186:530-544.
Djuric, Z. et al. "Quantitation of 5-(hydroxymethyl)uracil in DNA by gas chromatography with mass spectral detection" *Chem Res Toxicol.*, 1991, 4:687-691.
Floyd, R.A. et al. "Hydroxyl free radical mediated formation of 8-hydroxyguanine in isolated DNA" *Arch Biochem Biophys.*, 1988, 262:266-272.

(Continued)

*Primary Examiner* — Shafiqul Haq
(74) *Attorney, Agent, or Firm* — Saliwanchik, Lloyd & Eisenschenk

(57) ABSTRACT

The invention includes monoclonal and polyclonal antibodies, and antigen-binding fragments thereof, having specific binding affinity for 4,6-diamino-5-(formylamino)pyrimidine (FAPY-adenine); hybridomas producing such antibodies; immunoconjugates comprising an antibody or antigen-binding fragment of the invention coupled to a moiety; and in vitro and in vivo methods for using such antibodies, antibody fragments, and conjugates based on binding to FAPY-adenine; nucleic acids encoding the heavy and/or light chains of the antibodies; vectors comprising the nucleic acid sequences encoding the heavy and/or light chains; host cells comprising and, optionally, expressing the nucleic acid sequences; and methods for the production of the aforementioned materials.

20 Claims, 24 Drawing Sheets
(9 of 24 Drawing Sheet(s) Filed in Color)

(56) References Cited

OTHER PUBLICATIONS

Kalam, M.A. et al. "Genetic effects of oxidative DNA damages: comparative mutagenesis of the imidazole ring-opened formamidopyrimidines (Fapy lesions) and 8-oxo-purines in simian kidney cells" *Nucleic Acids Res.*, 2006, 34:2305-2315.

Loft, S. et al. "8-Hydroxydeoxyguanosine as a urinary biomarker of oxidative DNA damage" *J Toxicol Environ Health*, 1993, 40:391-404; abstract only.

Malins, D.C. et al. "The etiology of breast cancer. Characteristic alterations in hydroxyl radical-induced DNA base lesions during oncogenesis with potential for evaluating incidence risk" *Cancer*, 1993, 71:3036-3043.

Miller, E.C. and Miller, J.A. "Mechanisms of chemical carcinogenesis" *Cancer*, 1981, 47(suppl 5):1055-1064.

Reid, T.M. et al. "Endogenous mutations and cancer" *Princess Takamatsu Symp.*, 1991, 22:221-229.

Shigenaga, M.K. and Ames, B.N. "Assays for 8-hydroxy-2'-deoxyguanosine: a biomarker of in vivo oxidative DNA damage" *Free Radic Biol Med.*, 1991, 10:211-216.

Slaga, T.J. et al. "Studies on the mechanisms involved in multistage carcinogenesis in mouse skin" *J Cell Biochem*, 1982, 18:99-119.

Smela, M.E. et al. "The aflatoxin $B_1$ formamidopyrimidine adduct plays a major role in causing the types of mutations observed in human hepatocellular carcinoma" *Proc Natl Acad Sci USA*, 2002, 99:6655-6660.

Steenken, S. "Purine bases, nucleosides and nucleotides: aqueous solution redox chemistry and transformation of their radical cations e- and OH adducts" *Chem. Rev.*, 1989, 89:503-520.

\* cited by examiner 4-amino, 6-aminobutyrate(5-formamido)pyrimidine

FIG. 18

Heavy chain: DNA sequence (1404 bp)
Leader sequence-FR1-CDR1-FR2-CDR2-FR3-CDR3-FR4-Constant region-Stop codon ATGAACTTTGGGCTGAGCTTGATTTTCCTTGTCCTTAATTTTAAAAGTGTCCAGTGTGAAGTGATGC
TGGTGGAGTCTGGGGGAGGCTTAGTGAAGCCTGGAGGGTCCCTGAAACTCTCCTGTGCAGCCTCTGG
ATTCCCTTTCAGTAGTTATGTCATGTCTTGGGTTCGCCAGACTCCAGACACTGCGGAAGAGGCTGGAGTGGGTC
GCAACCATTAGTAGTGGTGGTGGTAGTACCTTCTATCCAGACAGTGTGAAGGGTCGGTTCACCATCT
CCAGAGACAATGCCAAGAACAACCTGTACCTGCAAATGAGCAGTCTGAGGACACGGCCTT
GTATTACTGTGCGAGCTTTATTACTACGGTCGTGGGGCTTACTGGGGCCAAGGGACTCTGGTCACT
GTCTCTGCAGCTACAACAGCCCCATCGGTGTCCCTTGGTCTGCAGTGACACATCTG
GATCCTCGGTGACACTGGGATGCCTTGTGCGCAGCCGGTGACCTCATCATCTGTGCCCAGACTCTGCAGCGTAACTGTAAAATGGAA
CTATGGAGCCCGTGTCCAGCCGGTGTGCAGCACACCTGGACTCTGCAGTCTGCAACGTAGCCACC
AGCAGCTTGGTGTACACCCTCAGCAGCGTCATCTGCAACGTAGCCCACCCCCCAGG
CAGCCAGCAAGACAGAGTTGATCAACATGAGAATACCTAAGGCCCTAGAATCCGTCTTCATCCTCCCCCAAAGCCAAG
TTCTTCATGCCACCTGGTAACATCCTAACCCCCAAGGTTACGTGGTGTGTGGACAAAGAAGTACACAGCCCCATCCAGCCTGAGTGCCCTGGATGTGAGCGAGGATGACC
CAGATGTCCAGTCCATGGGTTTGTGGACAACAACCCTCAAGGTCAACAAAGAAGTACACAGCCCTGGACACAGCAGCCCCGTGA
AGCTCAGTAGTACAACAGTACCTTCCAGGTAAATGCAAGGTCAACAACAACACCCTCAGTGCTCCCGAGATCAGGGAG
GGCAAGGAGTTCAAATGCAAAGTCAACAACAAAGATATACCCCCATCGAGAAGACCATCTCAA
AACCCAAAGGGAAGAGCCCAGACCTTGTGCTGATTACGCCCCCAACTTCTTCCACCCCCAACCTCTGTGAACAAATGTCCAA
GAAGAAGGTTAGTGTCTGACCTGGAAGGCCATCAGTGTGGAGTGGGAA
AGGAACGGAGAACTGGAGCAGGATTACAAGACAGACTCCAGCAGTTGGTTGCAAGGAGACCTGGACTACT
TCCTCTACAGCAAGCTCACTGTGGATACAGAAGGGATGGGAAATTTTTACCTGCTCCGT
GGTGCCATGAGGCTCTCCATAACCACCACCACAGAAGAACCTGTCTCGCTCCCCCTGGTAAATGA

FIG. 19

Heavy chain: Amino acids sequence (467 AA)
Leader sequence-FR1-CDR1-FR2-CDR2-FR3-CDR3-FR4-Constant region-Stop codon MNFGLSLIFLVLILKGVQCEVMLVESGGGLIVKPGGSLKLSCAASGFFSSYVMSWVRQTPQKRLEWV
ATISSGGGSTSNPDTVKGRFTISRDNAKNNLYLQMDSLRSEDTALYYCASLYYYGRGAYWGQGTLVT
VSAATTTAPSVYPLVPGCSDTSGSSVTLGCLVKGYFPEPVTVKWNYGALSSGVRTVSSVLQSGFYSL
SSLVTVPSSTWPSQTVICNVAHPASKTELIKRIEPRIPKPSTPPGSSCPPGNILGGPSVFIFPPKPK
DALMISLTPKVTCVVVDVSEDDPDVHVSWFVDNKEVHTAWTQPREAQYNSTFRVVSALPIQHQDWMR
GKEFKCKVNNKALPAPIERTISKPKGRAQTPQVYTIPPPREQMSKKKVSLTCLVTNFFSEAISVEWE
RNGELEQDYKNTPPILDSDGTYFLYSKLTVDTDSWLQGEIFTCSVVHEALHNHHTQKNLSRSPGK

FIG. 20

Light chain: DNA sequence (705 bp)
Leader sequence-FR1-CDR1-FR2-CDR2-FR3-CDR3-FR4-Constant region-Stop codon ATGGCCTGGATTTCACTTATACTCTCTCTCCTGGCTCAGCTCAGGGGCCATTCCCAGGCTGTTG
TGACTCAGGAATCTGCACTCACCAGTCACTCACTCTGTCGCTCAAGTTC
TGGGCCTGTTACAACCAGTAACTAGTAACAACCGAGAAAGACCAGTCTCAGGTTCATTATTCACTAAT
CTAATAGGTGGTACCAACAACCGAGCTCCAGTGTGTTCCTGCCAGATTCTCAGGTTCCCTGATTGGAG
ACAAGGCTGCCCTCCACCATCAGTGGCACAGAACCAAACTGCTGTCCTAGGCCAGCCACACTCTTCG
GTACAGTAACCATTGGTGTTCCACCTTCCCTCTGAGACTCGAGACAGTGGAAGGTAGATGGTACCCTCA
CCATCAGTCACTCTGATTCTACCAGGTGTGTCCAAACAGAGACAACAAGTACATGGCTAGCAGTACC
CGATCACTGATTCTACCAGGTGCCAGGAAGTGGAAGTGGACTGGAAGGTAGATGGCTAGCAGTACCTGACC
GGGTATGGAGACAAGAACCGAGCCTTCCAAACAGAGACAACAAGTACATGGCTAGCAGTACCTGACC
CTGACAGCAAGAGACATGGGAAAAGCATAGCAGTTACAGCTGCCAGGTCACTCATGAAGGTCACACTG
TGGAGAAGAGTTTGTCCCGTGCTGACTGTTCCTAG

FIG. 21

Light chain: Amino acids sequence (234 AA)
Leader sequence-FR1-CDR1-FR2-CDR2-FR2-CDR3-FR4-Constant region-Stop codon MAWISLILSLLALSSGAISQAVVTQESALTTSPGETVTLTCRSSSGPVTTSNYANWVQERPDHLFTN
LIGGTNNRAPGVPARFSGSLIGDKAALTITGAQTEDEAIYFCALWYSNHLVFGGGTKLTVLGQPKSS
PSVTLFPPSSEELETNKATLVCTITDFYPGVVTVDWKVDGTPVTQGMETTQPSKQSNNKYMASSYLT
LTARAWERHSSYSCQVTHEGHTVEKSLSRADCS

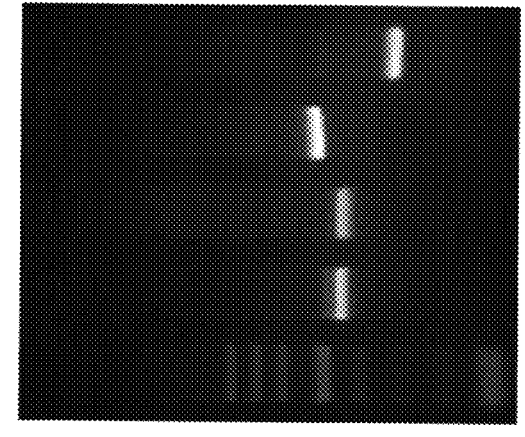

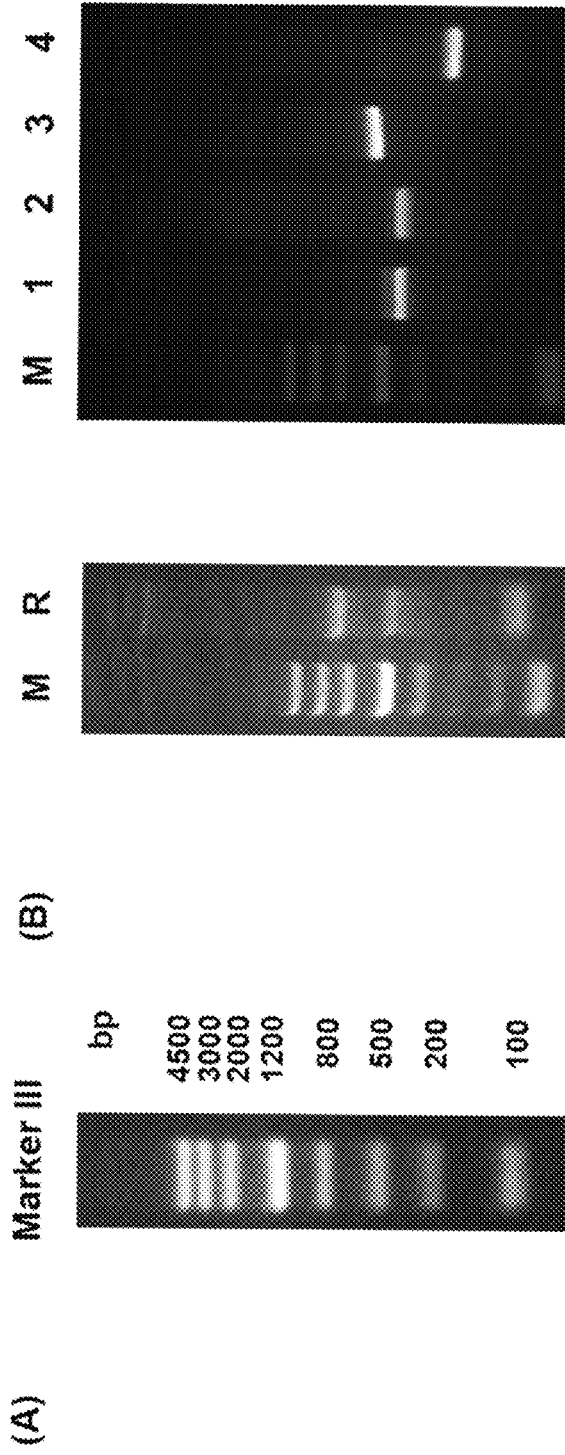

SEQUENCE LISTING

```
<160> NUMBER OF SEQ ID NOS: 8

<210> SEQ ID NO 1
<211> LENGTH: 1404
<212> TYPE: DNA
<213> ORGANISM: Mus musculus

<400> SEQUENCE: 1
atgaactttg ggctgagctt gattttcctt gtcctaattt taaaaggtgt ccagtgtgaa      60
gtgatgctgg tggagtctgg gggaggctta gtgaagcctg gagggtccct gaaactctcc     120
tgtgcagcct ctggattccc tttcagtagt tatgtcatgt cttgggttcg ccagactccg     180
cagaagaggc tggagtgggt cgcaaccatt agtagtggtg gtggtagtac ctctaatcca     240
gacactgtga agggtcggtt caccatctcc agagacaatg ccaagaacaa cctgtacctg     300
caaatggaca gtctcaggtc tgaggacacg gccttgtatt actgtgcgag cctttattac     360
tacggtcgtg gggcttactg gggccaaggg actctggtca ctgtctctgc agctacaaca     420
acagccccat ctgtctatcc cttggtccct ggctgcagtg acacatctgg atcctcggtg     480
acactgggat gccttgtcaa aggctacttc cctgagccgg taactgtaaa atggaactat     540
ggagccctgt ccagcggtgt gcgcacagtc tcatctgtcc tgcagtctgg gttctattcc     600
ctcagcagct tggtgactgt accctccagc acctggccca gccagactgt catctgcaac     660
gtagcccacc cagccagcaa gactgagttg atcaagagaa tcgagcctag aatacccaag     720
cccagtaccc ccccaggttc ttcatgccca cctggtaaca tcttgggtgg accatccgtc     780
ttcatcttcc ccccaaagcc caaggatgca ctcatgatct ccctaacccc caaggttacg     840
tgtgtggtgg tggatgtgag cgaggatgac ccagatgtcc atgtcagctg gtttgtggac     900
aacaaagaag tacacacagc ctggacacag ccccgtgaag ctcagtacaa cagtaccttc     960
cgagtggtca gtgccctccc catccagcac caggactgga tgaggggcaa ggagttcaaa    1020
tgcaaggtca acaacaaagc cctcccagcc cccatcgaga gaaccatctc aaaacccaaa    1080
ggaagagccc agacacctca agtatacacc ataccccac ctcgtgaaca aatgtccaag    1140
aagaaggtta gtctgacctg cctggtcacc aacttcttct ctgaagccat cagtgtggag    1200
tgggaaagga cggagaact ggagcaggat tacaagaaca ctccacccat cctggactca    1260
gatgggacct acttcctcta cagcaagctc actgtggata cagacagttg gttgcaagga    1320
gaaattttta cctgctccgt ggtgcatgag gctctccata accaccacac acagaagaac    1380
ctgtctcgct cccctggtaa atga                                          1404

<210> SEQ ID NO 2
<211> LENGTH: 467
<212> TYPE: PRT
<213> ORGANISM: Mus musculus

<400> SEQUENCE: 2
```

```
Met Asn Phe Gly Leu Ser Leu Ile Phe Leu Val Leu Ile Leu Lys Gly
  1               5                  10                  15
Val Gln Cys Glu Val Met Leu Val Glu Ser Gly Gly Gly Leu Val Lys
             20                  25                  30
Pro Gly Gly Ser Leu Lys Leu Ser Cys Ala Ala Ser Gly Phe Pro Phe
             35                  40                  45
Ser Ser Tyr Val Met Ser Trp Val Arg Gln Thr Pro Gln Lys Arg Leu
         50                  55                  60
Glu Trp Val Ala Thr Ile Ser Ser Gly Gly Gly Ser Thr Ser Asn Pro
 65                  70                  75                  80
Asp Thr Val Lys Gly Arg Phe Thr Ile Ser Arg Asp Asn Ala Lys Asn
                 85                  90                  95
Asn Leu Tyr Leu Gln Met Asp Ser Leu Arg Ser Glu Asp Thr Ala Leu
                100                 105                 110
Tyr Tyr Cys Ala Ser Leu Tyr Tyr Gly Arg Gly Ala Tyr Trp Gly
            115                 120                 125
Gln Gly Thr Leu Val Thr Val Ser Ala Ala Thr Thr Thr Ala Pro Ser
130                 135                 140
Val Tyr Pro Leu Val Pro Gly Cys Ser Asp Thr Ser Gly Ser Ser Val
145                 150                 155                 160
Thr Leu Gly Cys Leu Val Lys Gly Tyr Phe Pro Glu Pro Val Thr Val
                165                 170                 175
Lys Trp Asn Tyr Gly Ala Leu Ser Ser Gly Val Arg Thr Val Ser Ser
                180                 185                 190
Val Leu Gln Ser Gly Phe Tyr Ser Leu Ser Ser Leu Val Thr Val Pro
            195                 200                 205
Ser Ser Thr Trp Pro Ser Gln Thr Val Ile Cys Asn Val Ala His Pro
210                 215                 220
Ala Ser Lys Thr Glu Leu Ile Lys Arg Ile Glu Pro Arg Ile Pro Lys
225                 230                 235                 240
Pro Ser Thr Pro Pro Gly Ser Ser Cys Pro Pro Gly Asn Ile Leu Gly
                245                 250                 255
Gly Pro Ser Val Phe Ile Phe Pro Pro Lys Pro Lys Asp Ala Leu Met
                260                 265                 270
Ile Ser Leu Thr Pro Lys Val Thr Cys Val Val Val Asp Val Ser Glu
            275                 280                 285
Asp Asp Pro Asp Val His Val Ser Trp Phe Val Asp Asn Lys Glu Val
290                 295                 300
His Thr Ala Trp Thr Gln Pro Arg Glu Ala Gln Tyr Asn Ser Thr Phe
305                 310                 315                 320
Arg Val Val Ser Ala Leu Pro Ile Gln His Gln Asp Trp Met Arg Gly
                325                 330                 335
Lys Glu Phe Lys Cys Lys Val Asn Asn Lys Ala Leu Pro Ala Pro Ile
                340                 345                 350
Glu Arg Thr Ile Ser Lys Pro Lys Gly Arg Ala Gln Thr Pro Gln Val
            355                 360                 365
Tyr Thr Ile Pro Pro Pro Arg Glu Gln Met Ser Lys Lys Lys Val Ser
370                 375                 380
Leu Thr Cys Leu Val Thr Asn Phe Phe Ser Glu Ala Ile Ser Val Glu
385                 390                 395                 400
Trp Glu Arg Asn Gly Glu Leu Glu Gln Asp Tyr Lys Asn Thr Pro Pro
                405                 410                 415
```

```
Ile Leu Asp Ser Asp Gly Thr Tyr Phe Leu Tyr Ser Lys Leu Thr Val
            420                 425                 430

Asp Thr Asp Ser Trp Leu Gln Gly Glu Ile Phe Thr Cys Ser Val Val
            435                 440                 445

His Glu Ala Leu His Asn His His Thr Gln Lys Asn Leu Ser Arg Ser
450                 455                 460

Pro Gly Lys
465

<210> SEQ ID NO 3
<211> LENGTH: 705
<212> TYPE: DNA
<213> ORGANISM: Mus musculus

<400> SEQUENCE: 3
atggcctgga tttcacttat actctctctc ctggctctca gctcaggggc catttcccag      60
gctgttgtga ctcaggaatc tgcactcacc acatcacctg gtgaaacagt cacactcact     120
tgtcgctcaa gttctgggcc tgttacaact agtaactatg ccaactgggt ccaagaaaga     180
ccagatcatt tattcactaa tctaataggt ggtaccaaca accgagctcc aggtgttcct     240
gccagattct caggttccct gattggagac aaggctgccc tcaccatcac aggggcacag     300
actgaggatg aggcaatata tttctgtgct ctatggtaca gtaaccattt ggtgttcggt     360
ggaggaacca aactgactgt cctaggccag cccaagtctt cgccatcagt caccctgttt     420
ccaccttcct ctgaagagct cgagactaac aaggccacac tggtgtgtac gatcactgat     480
ttctacccag gtgtggtgac agtggactgg aaggtagatg gtaccccctgt cactcagggt     540 atggagacaa cccagccttc caaacagagc aacaacaagt acatggctag cagctacctg     600
accctgacag caagagcatg ggaaaggcat agcagttaca ctgccaggt cactcatgaa     660 ggtcacactg tggagaagag tttgtcccgt gctgactgtt cctag                    705

<210> SEQ ID NO 4
<211> LENGTH: 234
<212> TYPE: PRT
<213> ORGANISM: Mus musculus

<400> SEQUENCE: 4

Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Ser Gly Pro Val
        35                  40                  45

Thr Thr Ser Asn Tyr Ala Asn Trp Val Gln Glu Arg Pro Asp His Leu
    50                  55                  60

Phe Thr Asn Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Leu Val Phe Gly Gly Thr Lys Leu Thr Val Leu
        115                 120                 125

Gly Gln Pro Lys Ser Ser Pro Ser Val Thr Leu Phe Pro Pro Ser Ser
    130                 135                 140
```

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly Met Glu Thr Thr Gln Pro Ser Lys Gln Ser Asn Asn
            180                 185                 190

Lys Tyr Met Ala Ser Ser Tyr Leu Thr Leu Thr Ala Arg Ala Trp Glu
        195                 200                 205

Arg His Ser Ser Tyr Ser Cys Gln Val Thr His Glu Gly His Thr Val
    210                 215                 220

Glu Lys Ser Leu Ser Arg Ala Asp Cys Ser
225                 230

<210> SEQ ID NO 5
<211> LENGTH: 593
<212> TYPE: DNA
<213> ORGANISM: Mus musculus

<400> SEQUENCE: 5
atgaacttcg ggctgagctt gattttcctt gtcctaattt taaaaggtgt ccagtgtgaa     60
gtgatgctgg tggagtctgg gggaggctta gtgaagcctg agggtccct gaaactctcc    120 tgtgcagcct ctggattccc tttcagtagt tatgtcatgt cttgggttcg ccagactccg    180
cagaagaggc tggagtgggt cgcaaccatt agtagtggtg gtggtagtac ctctaatcca    240
gacactgtga agggtcggtt caccatctcc agagacaatg ccaagaacaa cctgtacctg    300
caaatggaca gtctcaggtc tgaggacacg gccttgtatt actgtgcgag ctttattac    360 tacggtcgtg gggcttactg gggccaaggg actctggtca ctgtctctgc agctacaaca    420 acagcccat ctgtctatcc cttggtccct ggctgcagtg acacatctgg atcctcggtg    480
acactgggat gccttgtcaa aggctacttc cctgagccgg taactgtaaa atggaactat    540
ggagccctgt ccagcggtgt gcgcacagtc tcatctgtcc tgcagtctgg gtt         593

<210> SEQ ID NO 6
<211> LENGTH: 505
<212> TYPE: DNA
<213> ORGANISM: Mus musculus

<400> SEQUENCE: 6
agccggtaac tgtaaaatgg aactatggag ccctgtccag cggtgtgcgc acagtctcat     60
ctgtcctgca gtctgggttc tattccctca gcagcttggt gactgtaccc tccagcacct    120
ggcccagcca gactgtcatc cgcaacgtag cccacccagc cagcaagact gagttgatca    180
agagaatcga gcctagaata cccaagccca gtacccccc aggttcttca tgcccacctg    240
gtaacatctt gggtggacca tccgtcttca tcttcccccc aaagcccaag gatgcactca    300
tgatctccct aacccccaag gttacgtgtg tggtggtgga tgtgagcgag gatgacccag    360
atgtccatgt cagctggttt gtggacaaca agaagtaca cacagcctgg acacagcccc    420
gtgaagctca gtacaacagt accttccgag tggtcagtgc cctccccatc cagcaccagg    480
actggatgag gggcaaggag ttcaa                                          505

<210> SEQ ID NO 7
<211> LENGTH: 465
<212> TYPE: DNA
<213> ORGANISM: Mus musculus

<400> SEQUENCE: 7

```
gctcagtaca acagtacctt ccgagtggtc agtgccctcc ccatccagca ccaggactgg      60
atgaggggca aggagttcaa atgcaaggtc aacaacaaag ccctcccagc ccccatcgag     120
agaaccatct caaacccaa aggaagagcc cagacacctc aagtatacac catacccca      180 cctcgtgaac aaatgtccaa gaagaaggtt agtctgacct gcctggtcac caacttcttc    240
tctgaagcca tcagtgtgga gtgggaaagg aacggagaac tggagcagga ttacaagaac    300
actccaccca tcctggactc agatgggacc tacttcctct acagcaagct cactgtggat    360
acagacagtt ggttgcaagg agaaattttt acctgctccg tggtgcatga ggctctccat    420
aaccaccaca cacagaagaa cctgtctcgc ccccctggta aatga                    465

<210> SEQ ID NO 8
<211> LENGTH: 514
<212> TYPE: DNA
<213> ORGANISM: Mus musculus

<400> SEQUENCE: 8
atggcctgga tttcacttat actctctctc ctggctctca gctcagggc catttcccag      60 gctgttgtga ctcaggaatc tgcactcacc acatcacctg gtgaaacagt cacactcact    120
tgtcgctcaa gttctgggcc tgttacaact agtaactatg ccaactgggt ccaagaaaga    180
ccagatcatt tattcactaa tctaataggt ggtaccaaca accgagctcc aggtgttcct    240
gccagattct caggttccct gattggagac aaggctgccc tcaccatcac aggggcacag    300
actgaggatg aggcaatata tttctgtgct ctatggtaca gtaaccattt ggtgttcggt    360
gggggaacca aactgactgt cctaggccag cccaagtctt cgccatcagt caccctgttt    420
ccaccttcct ctgaagagct cgagactaac aaggccacac tggtgtgtac gatcactgat    480
ttctacccag gtgtggtgac agtggactgg aagg                                514
```

ANTIBODIES SPECIFIC FOR 4,6-DIAMINO-5-(FORMAMIDO)PYRIMIDINE AND USES THEREOF

CROSS-REFERENCE TO RELATED APPLICATION

The present application claims the benefit of U.S. Provisional Application Ser. No. 62/239,686, filed Oct. 9, 2015, which is hereby incorporated by reference herein in its entirety, including any figures, tables, nucleic acid sequences, amino acid sequences, or drawings.

BACKGROUND OF THE INVENTION

Oncogenesis is considered to be a multi-stage process involving introduction of alterations in the DNA which, if left unrepaired, often lead to mutagenic changes in the DNA of daughter cells after cell division (1-3). Accumulation of mutagenic damage in genomic DNA can ultimately lead to the necessary and sufficient conditions for malignant conversion and tumorigenesis. Diverse agents have been implicated in carcinogenesis, and lead to introduction of DNA modifications with mutagenic potential. Interest has focused on oxidative damage from single electron oxidative steps induced by multiple forms of reactive oxygen species (ROS) resulting from such in vivo exposures.

Modification of DNA bases by the introduction of a single oxygen atom in a purine ring is a type of single-electron oxidation caused by ROS. Such DNA base damage includes the production of 8-hydroxydeoxyguanine (8-hydroxy-Gua) and 8-hydroxydeoxyadenine (8-hydroxy-Ade). Studies indicate that these lesions are frequently present in substantial concentrations in the DNA in cancerous tumors or in histologically normal tissue from cancer patients, as high as 1 in $10^2$ or $10^3$ normal bases, but generally very low in normal healthy tissues. Studies have shown that there is a 1- to 2% level of misreading of 8-hydroxy derivatives during DNA replication resulting in base substitutions and transversions (4,5).

Analysis of single electron oxidations of adenine in solution has demonstrated that the redox status of the reaction controls the structure of the reaction product (6). Under oxidative conditions, the transient 8-oxo-Ade radical is quantitatively converted through the loss of an electron and protonation to form the 8-OH-Ade product, the structure of which is shown in FIG. 1B. Alternatively, under reductive conditions, an electron is added and after protonation and possible rearrangement the ring-opening formamidopyrimidine, 4,6-diamino-5-formamidopyridine (also referred to herein as FAPY-A, FAPY-Ade, or FAPY-adenine) derivative is the exclusive product. The structure of FAPY-Ade is shown in FIG. 1A. Recent studies have shown FAPY derivatives of purine bases to also be mutagenic (7,8). In particular, FAPY-A was shown to lead to A→C transversions and FAPY-G to G→T transversions (7).

Analysis of ROS-induced DNA base lesions present in normal human breast tissue, breast cancer tumors, and histologically normal breast tissue from breast cancer patients have been conducted using gas chromatography-mass spectrometry (GC-MS) (9). Two general types of results were obtained. Increased levels of 8-hydroxy purine derivatives were observed in both cancerous tumors and the surrounding normal tissue from cancer patients compared to normal, non-cancer specimens. In contrast, substantial elevations of the ring-opening FAPY derivatives were highly expressed in normal tissues but were very low in cancer derived tissues. This qualitative difference in the nature of ROS-induced DNA damage results from the fundamentally different redox status of cancerous or pre-cancerous tissues (oxidative) versus the more reductive environment of normal tissues (10-13). Because of their accumulation in cancerous tissues, 8-OH-derivatives of purines have been utilized as markers for carcinogenesis. However, redox chemistry suggests they may only be detectable in more oxidative tissues occurring in cancer and later stages of carcinogenesis. Thus, the alternate FAPY-derivatives may have greater utility in analyzing the earlier stages of carcinogenesis and potentially offer a useful risk assessment marker for predicting future cancer incidence. In particular, FAPY derivatives may have more mutagenic significance in early stages of carcinogenesis in normal tissues than 8-hydroxy derivatives whose expression is high in more oxidative conditions such as cancerous tissues and tumors.

To date, most studies focusing on effects of ROS on DNA have relied on chemical approaches for detection and quantitation. These include GC-MS/SIM (14-18) and high performance liquid chromatography-electrochemical detection (HPLC-ECD) (19-21) methodologies that require initial purification of tissue DNA in high purity, are time consuming, cumbersome, and not practical for applied diagnostic or screening uses outside of a research laboratory.

BRIEF SUMMARY OF THE INVENTION

To provide an improved quantitation method, the present inventors have developed antibodies highly specific for the FAPY-A structure. These antibodies can be used to directly measure genotoxic changes present in DNA via immunohistochemistry or a quantitative ELISA. This has the advantage of convenience, high sensitivity and, because it is applied to the DNA, measures effects on the organism directly involved in manifesting chronic damage to the organism, including cancer. Antibody-based detection methods have significant advantages of simplicity, flexibility, and speed, elements absolutely required for practical studies involving ROS modifications of DNA.

BRIEF DESCRIPTION OF THE DRAWINGS

The patent or application file contains at least one drawing executed in color.

Copies of this patent or patent application publication with color drawing(s) will be provided by the Patent and Trademark Office upon request and payment of the necessary fee.

FIG. 1A: 4,6-diamino-5-formamidopyridine (also referred to herein as FAPY-A, FAPY-Ade, or FAPY-adenine). FIG. 1B: 8-hydroxyadenine (also referred to herein as 8-OH-A, 8-OH-Ade, or 8-OH-adenine).

FIG. 18. FA5 antibody heavy chain DNA sequence (SEQ ID NO:1), encoding the leader sequence: nucleotides 1-57; framework region 1 (FR1): 58-147; complementarity determining region 1 CDR1: nucleotides 148-162; framework region 2 (FR2): nucleotides 163-204; complementarity determining region 2 (CDR2): nucleotides 205-255; framework region 3 (FR3): nucleotides 256-351; complementarity determining region 3 (CDR3): nucleotides 352-378; framework region 4 (FR4): nucleotides 379-411; constant region: nucleotides 412-1401; and stop codon: nucleotides 1402-1404.

FIG. 19. FA5 antibody deduced heavy chain amino acid sequence (SEQ ID NO:2), including leader sequence: amino acids 1-19; FR1: amino acids 20-49; CDR1: amino acids 50-54; FR2: amino acids 55-68; CDR2: amino acids 69-85; FR3: amino acids 86-117: CDR3: amino acids 118-126; FR4: amino acids 127-137; and constant region: amino acids 138-467.

FIG. 20. FA5 antibody light chain DNA sequence (SEQ ID NO:3), encoding the leader sequence: nucleotides 1-57; FR1: nucleotides 58-123; CDR1: nucleotides 124-165; FR2: nucleotides 166-210; CDR2: nucleotides 211-231; FR3: nucleotides 232-327; CDR3: nucleotides 328-354; FR4: nucleotides 355-384; constant region: nucleotides 385-702; and stop codon: nucleotides 703-705.

FIG. 21. FA5 antibody deduced light chain amino acid sequence (SEQ ID NO:4), including the leader sequence: amino acids 1-19; FR1: amino acids 20-41; CDR1: amino acids 42-55; FR2: amino acids 56-70; CDR2: amino acids 71-77; FR3: amino acids 78-109; CDR3: amino acids 110-118; FR4: amino acids 119-128; and constant region: amino acids 129-234.

FIGS. 22A and 22B. Agarose gel electrophoresis of total RNA of the provided hybridoma of 406686-1. DNA marker Marker III (FIG. 22A). Lane M, DNA marker Marker III; Lane R, Total RNA of 406686-1 (FIG. 22B).

FIG. 23. Agarose gel electrophoresis of PCR products of 406686-1. Lane M, DNA marker Marker III; Lane 1, $V_H$ of 406686-1; Lane 2, $V_L$ of 406686-1; Lane 3, $C_H$ of 406686-1; Lane 4, $C_L$ of 406686-1.

Figure 24:
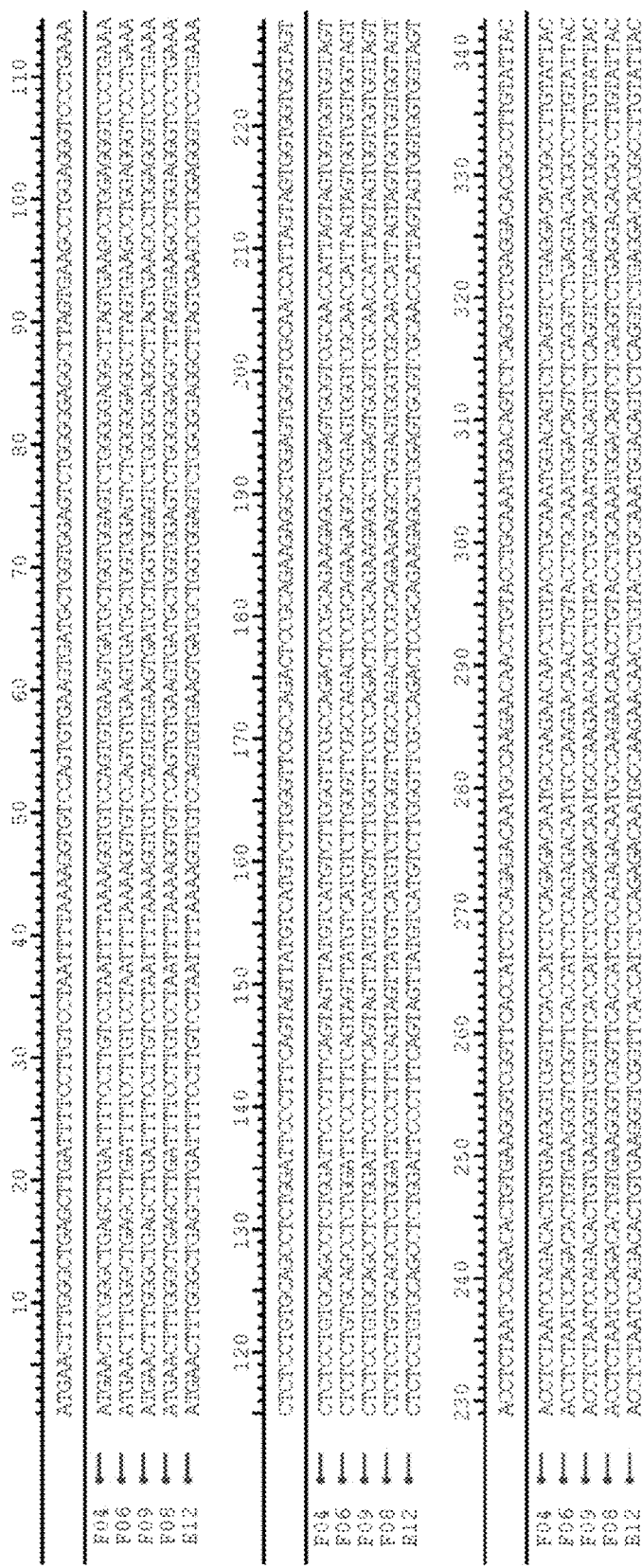
FIGS. 24 and 25. Sequence alignments of multiple clones (heavy and light chains, respectively). Five single colonies with correct $V_H$, $V_L$, $C_H$, and $C_L$ insert sizes were sent for sequencing, and the $V_H$, $V_L$, $C_H$, and $C_L$ genes of the five different clones were found nearly identical. The sequences in the sequence alignments are summarized below.
Figure 24:
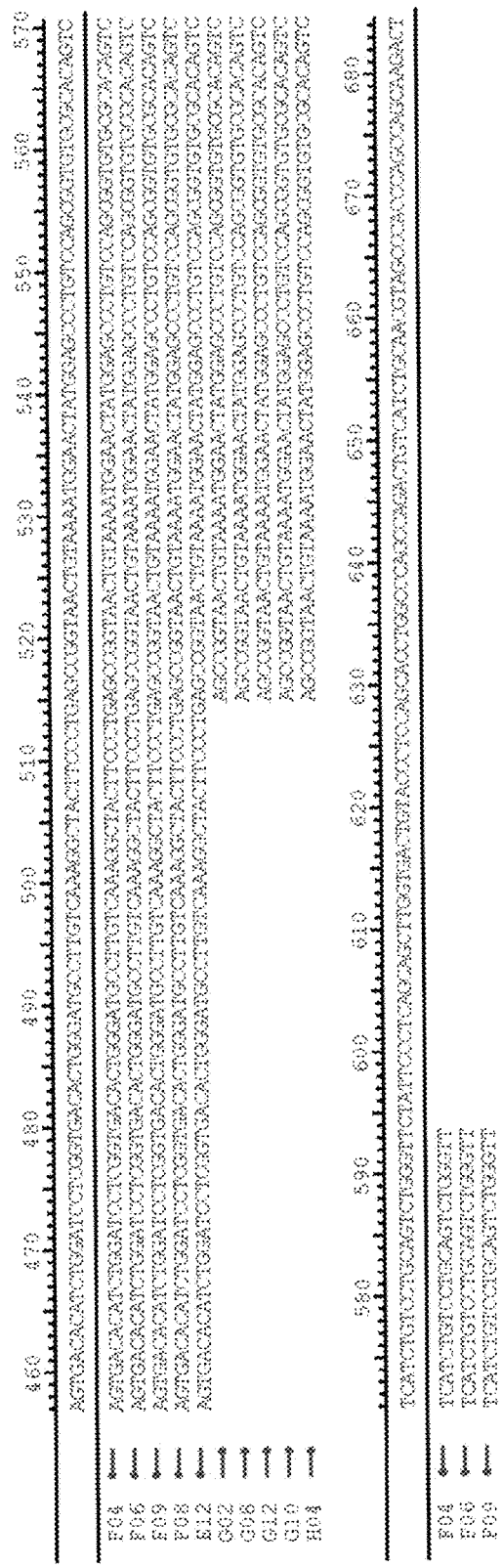
Figure 24:
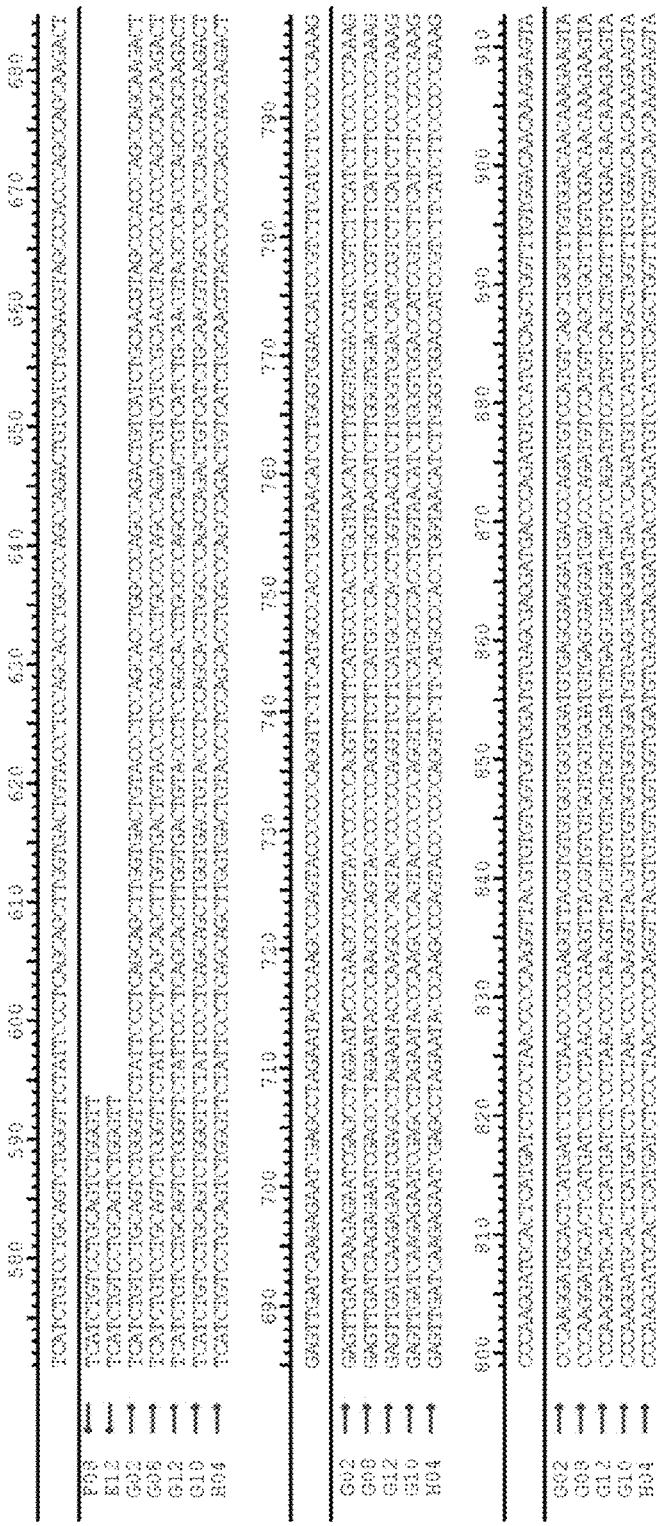

Sequences shown in FIG. 24 (heavy chains):

Top Row: positions 1 to 684 correspond to positions 1 to 684 of SEQ ID NO:1 and positions 685 to 1518 correspond to positions 571 to 1404 of SEQ ID NO:1; F04 (F04-A90585-406686-1-vh-G3-R234.a(1>633)): SEQ ID NO:5; F06 (F06-A90587-406686-1-vh-G3-R234.a(1>631)): corresponds to positions 1 to 593 of SEQ ID NO:1; F09 (F09-A90590-406686-1-vh-G3-R234.a(1>629)): corresponds to positions 1 to 593 of SEQ ID NO:1; F08 (F08-A90589-406686-1-vh-G3-R234.a(1>626)): corresponds to positions 1 to 593 of SEQ ID NO:1; E12 (E12-A90581-406686-1-vh-G3-R234.a(1>612)): corresponds to positions 1 to 593 of SEQ ID NO:1; G02 (G02-A90593-406686-1-CH-C16.ab1(32>536)): corresponds to positions 515 to 1019 of SEQ ID NO:1; G08 (G08-A90596-406686-1-CH-C16.ab1(32>536)): SEQ ID NO:6; G12 (G12-A90598-406686-1-CH-C16.ab1(32>536)): corresponds to positions 515 to 1019 of SEQ ID NO:1; G10 (G10-A90597-406686-1-CH-C16.ab1(32>536)): corresponds to positions 515 to 1019 of SEQ ID NO:1; H04 (H04-A90600-406686-1-CH-C16.ab1(32>536)): corresponds to positions 515 to 1019 of SEQ ID NO:1; G11 (G11-A90597-406686-1-CH-P258.ab1(16>554)): corresponds to positions 940 to 1404 of SEQ ID NO:1; H01 (H01-A90598-406686-1-CH-P258.ab1(15>551)): corresponds to positions 940 to 1404 of SEQ ID NO:1; G03 (G03-A90593-406686-1-CH-P258.ab1(11>563)): corresponds to positions 940 to 1404 of SEQ ID NO:1; H05 (H05-A90600-406686-1-CH-P258.ab1(10>556)): SEQ ID NO:7; G09 (G09-A90596-406686-1-CH-P258.ab1(9>559)): corresponds to positions 940 to 1404 of SEQ ID NO:1.

Figure 25:
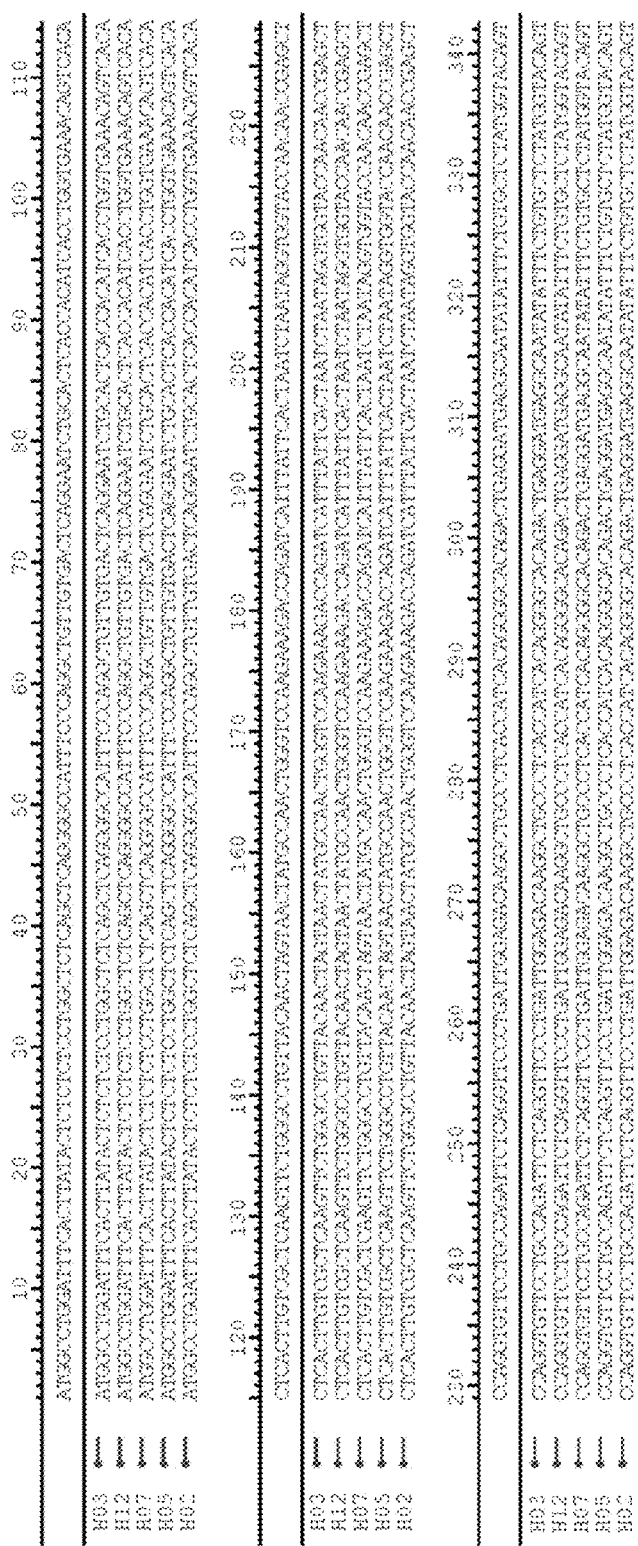
Figure 25:
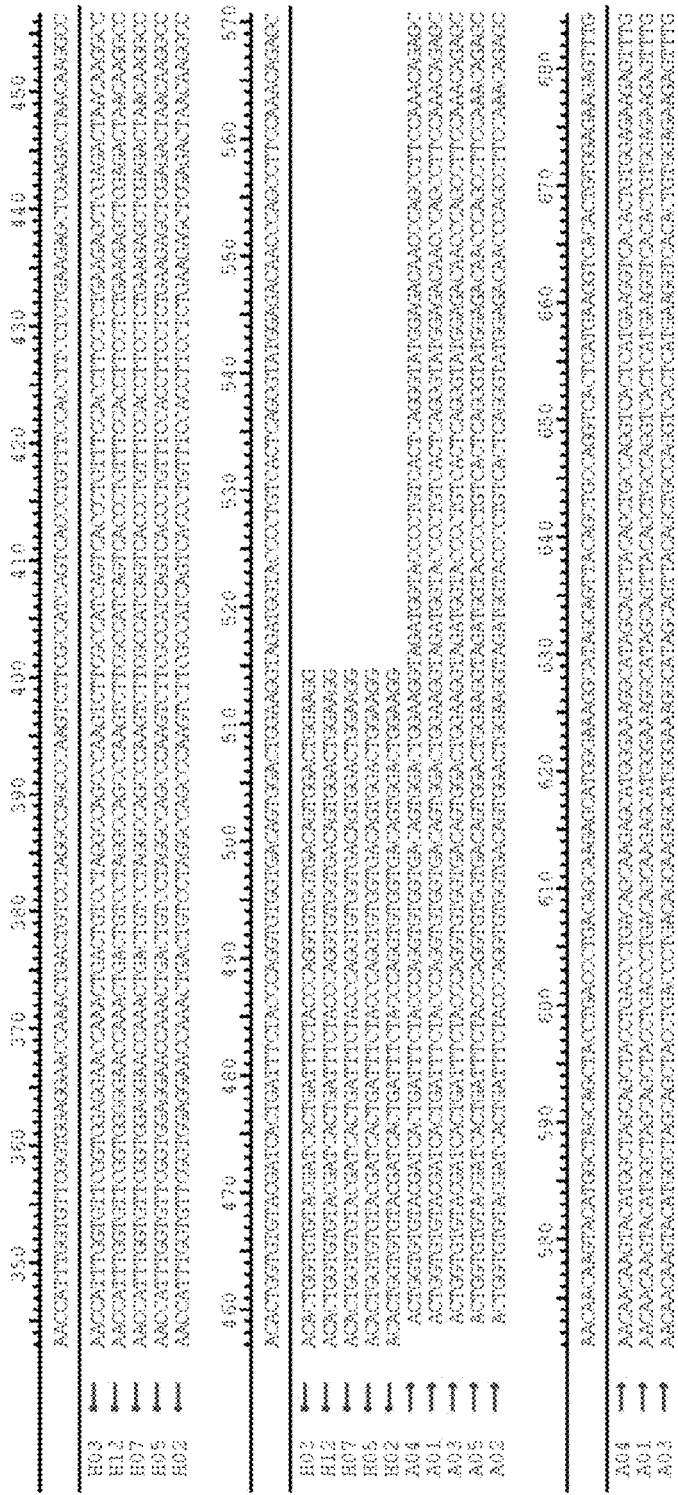
Figure 25:
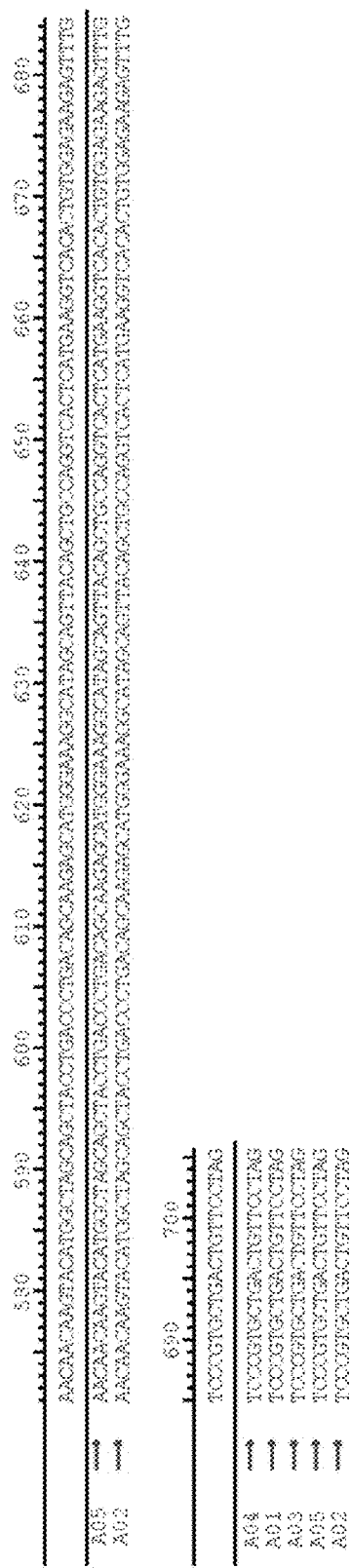

Sequences shown in FIG. 25 (light chains):

Top Row: positions 1 to 684 correspond to positions 1 to 684 of SEQ ID NO:3 and positions 685 to 819 correspond to positions 571 to 705 of SEQ ID NO:3; H03 (H03-A90602-406686-1-VL-M13-48.ab(7>520)): corresponds to positions 1 to 514 of SEQ ID NO:3; H12 (H12-A90608-406686-1-VL-M13-47.a(15>528)): SEQ ID NO:8; H07 (H07-A90606-406686-1-VL-M13-48.ab(8>521)): corresponds to positions 1 to 514 of SEQ ID NO:3; H05 (H05-A90604-406686-1-VL-M13-48.ab(7>520)): corresponds to positions 1 to 514 of SEQ ID NO:3; H02 (H02-A90601-406686-1-VL-M13-48.a(11>524)): corresponds to positions 1 to 514 of SEQ ID NO:3; A04 (A04-A90729-406686-1-CL-C32.ab1(4>335)): corresponds to positions 459 to 705 of SEQ ID NO:3; A01 (A01-A90726-406686-1-CL-C32.ab1(4>331)): corresponds to positions 459 to 705 of SEQ ID NO:3; A03 (A03-A90728-406686-1-CL-C32.ab1(4>332)): corresponds to positions 459 to 705 of SEQ ID NO:3; A05 (A05-A90730-406686-1-CL-C32.ab1(4>334)): corresponds to positions 459 to 705 of SEQ ID NO:3; A02 (A02-A90727-406686-1-CL-C32.ab1(4>331)): corresponds to positions 459 to 705 of SEQ ID NO:3.

Figure 26:
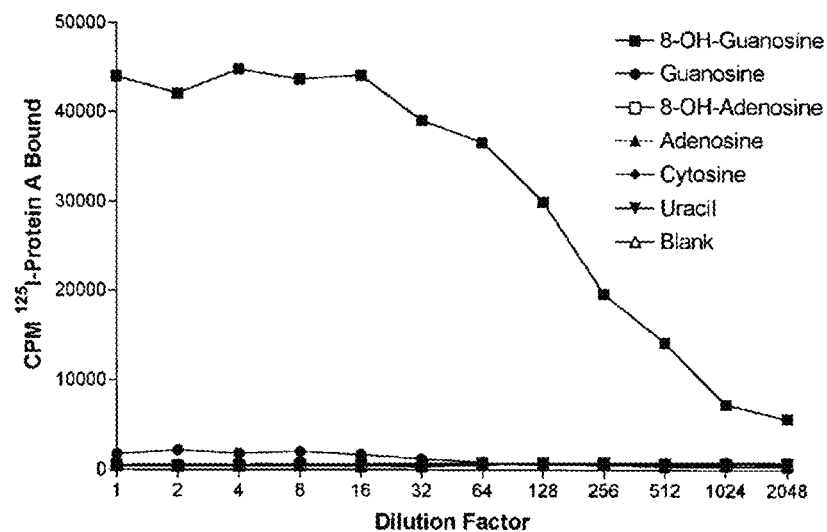

FIG. 26. 8-OH-Gua binding specificity of antibody 8G14. Serial dilutions of BSA conjugates with the indicated nucleosides were coated on assay plates and the amount of 8G14 antibody (IgM) from tissue culture supernatant bound was determined.

Figure 27A:
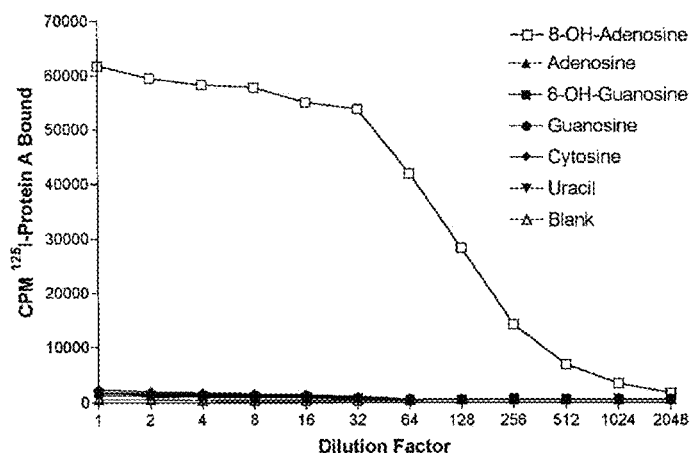
Figure 27B:
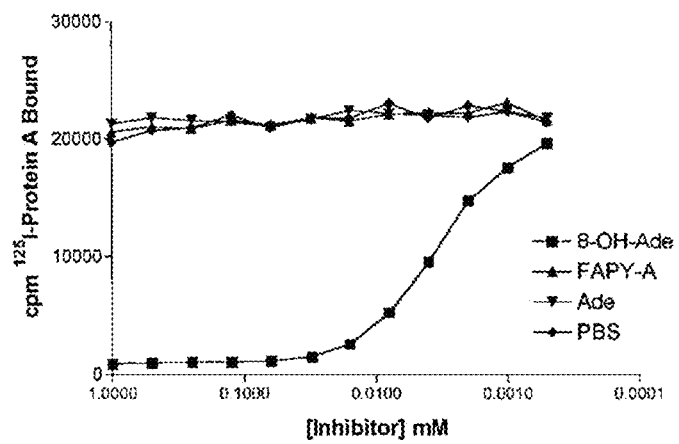

FIGS. 27A-27B. 8-OH-Ade binding specificity of antibody 8A6. FIG. 27A: Serial dilutions of BSA-nucleoside conjugates were coated on plates and the amount of 8A6 antibody (IgG1) bound was determined. FIG. 27B: Inhibition of 8A6 binding to the 8-OH-Ade BSA conjugate by serial dilutions of soluble antigens.

Figure 28A:
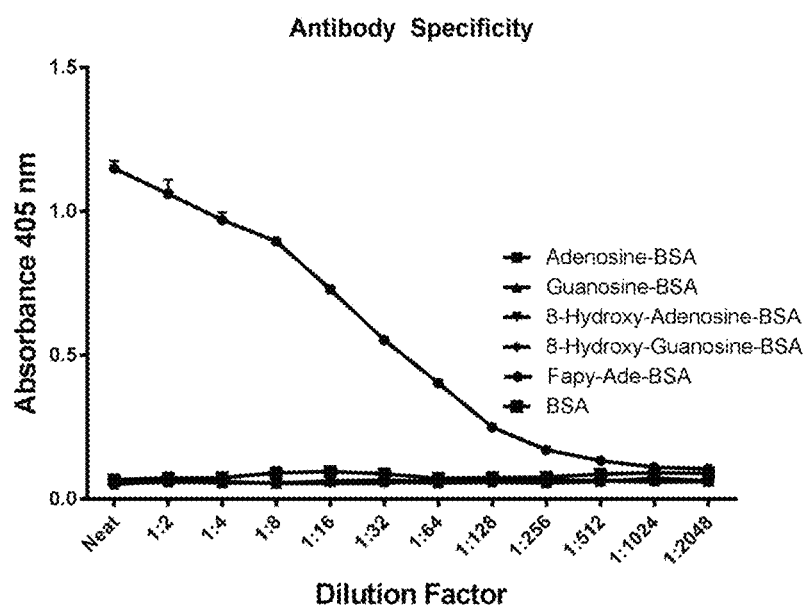
Figure 28B:
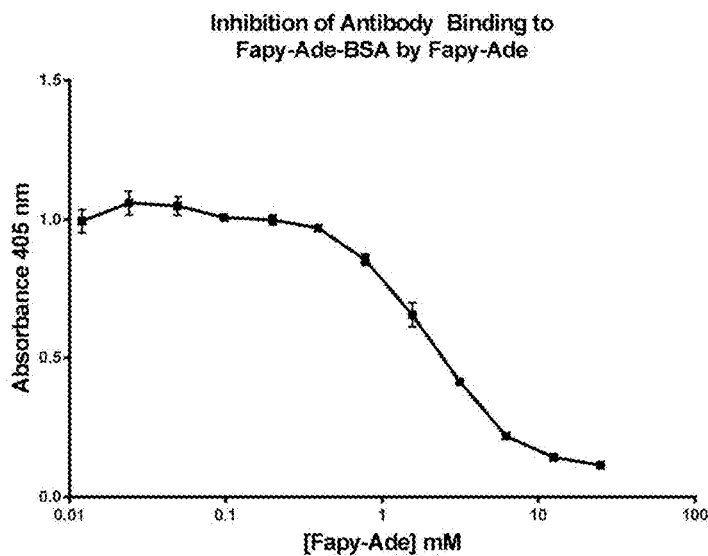

FIGS. 28A-28B. FAPY-Ade binding specificity of antibody FA5. FIG. 28A: Serial dilutions of BSA-nucleoside conjugates were coated on plates and the amount of FA5 antibody (IgG3) bound was determined. FIG. 28B: Inhibition of FA5 binding to the FAPY-Ade-BSA conjugate by serial dilutions of FAPY-Ade hapten.

Figure 29A:
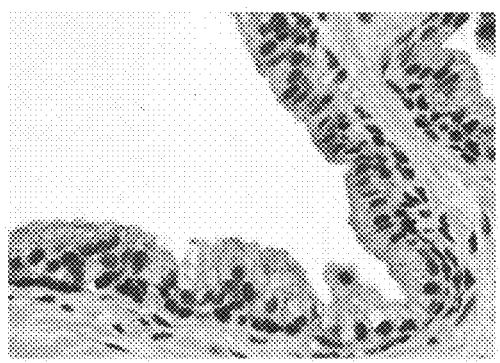
Figure 29B:
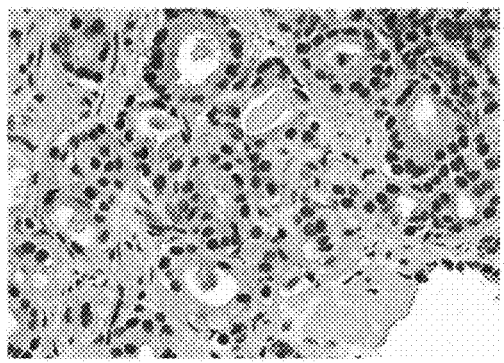

FIGS. 29A-29B. Immunohistochemistry (IHC) of benign (FIG. 29A) and cancerous (FIG. 29B) regions of prostatic cancer tissue with the 8-OH-Gua specific 8G14 antibody.

Significant staining (brown) is present in nuclei from both cancerous and surrounding benign tissue.

Figure 30A:
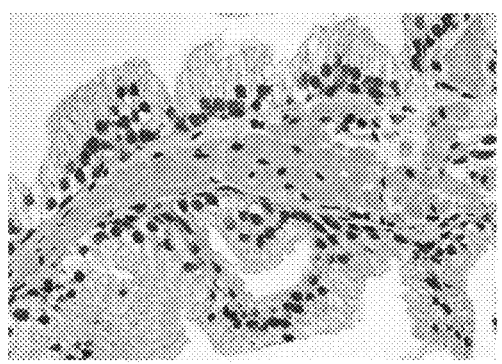
Figure 30B:
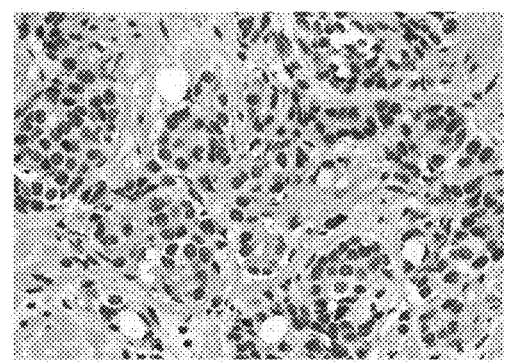

FIGS. 30A-30B. IHC of benign (FIG. 30A) and cancerous (FIG. 30B) regions of prostatic cancer tissue with the 8-OH-Ade specific 8A6 antibody. Significant staining (brown) is present in nuclei from both cancerous and surrounding benign tissue.

Figure 31A:
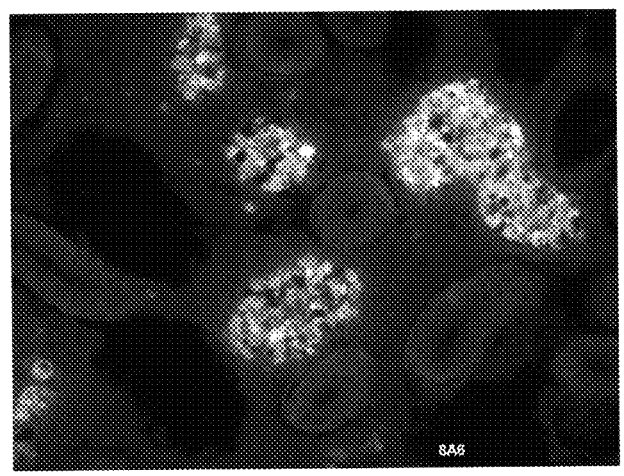
Figure 31B:
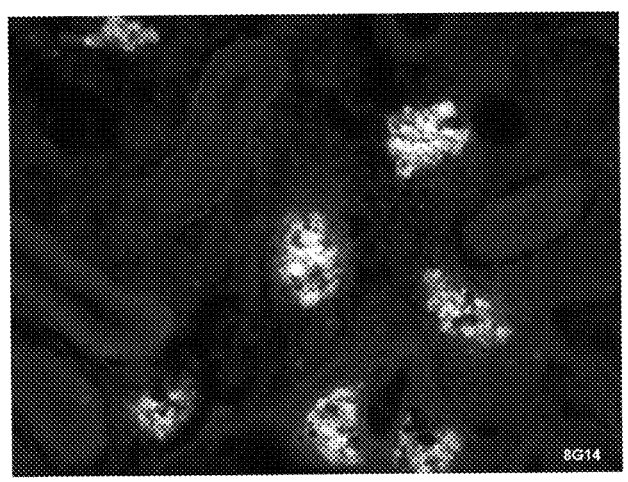
Figure 31C:
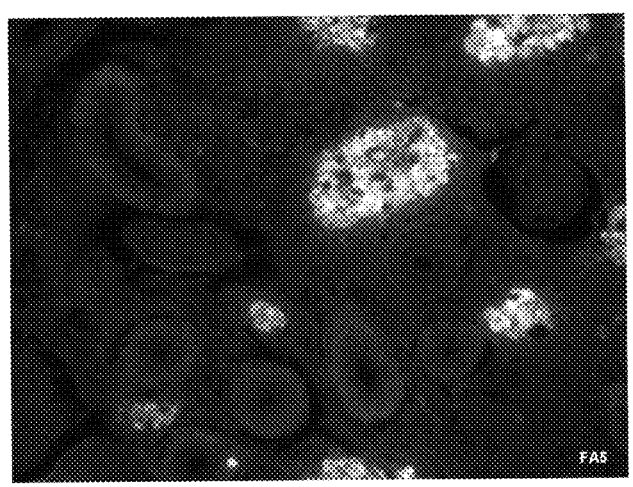

FIGS. 31A-31C. IHC of English sole kidney tissue with antibodies 8A6 specific for 8-hydroxy-adenine (IgG1) (FIG. 31A), 8G14 specific for 8-hydroxy-guanine (IgM) (FIG. 31B), and FA5 specific for FAPY-adenine (IgG3) (FIG. 31C). The tissue was derived from a 7 year old English sole from Eagle Harbor, Puget Sound, Wash. Eagle Harbor is known for aromatic hydrocarbon contaminated sediments and is associated with a high incidence of liver cancer in fish inhabiting that location.

BRIEF DESCRIPTION OF THE SEQUENCES

SEQ ID NO:1 is the FA5 antibody heavy chain DNA sequence (shown in FIG. 18), encoding the leader sequence: nucleotides 1-57; framework region 1 (FR1): 58-147; complementarity determining region 1 CDR1: nucleotides 148-162; framework region 2 (FR2): nucleotides 163-204; complementarity determining region 2 (CDR2): nucleotides 205-255; framework region 3 (FR3): nucleotides 256-351; complementarity determining region 3 (CDR3): nucleotides 352-378; framework region 4 (FR4): nucleotides 379-411; constant region: nucleotides 412-1401; and stop codon: nucleotides 1402-1404.

SEQ ID NO:2 is the FA5 antibody deduced heavy chain amino acid sequence (shown in FIG. 19), including leader sequence: amino acids 1-19; FR1: amino acids 20-49; CDR1: amino acids 50-54; FR2: amino acids 55-68; CDR2: amino acids 69-85; FR3: amino acids 86-117: CDR3: amino acids 118-126; FR4: amino acids 127-137; and constant region: amino acids 138-467.

SEQ ID NO:3 is the FA5 antibody light chain DNA sequence (shown in FIG. 20), encoding the leader sequence: nucleotides 1-57; FR1: nucleotides 58-123; CDR1: nucleotides 124-165; FR2: nucleotides 166-210; CDR2: nucleotides 211-231; FR3: nucleotides 232-327; CDR3: nucleotides 328-354; FR4: nucleotides 355-384; constant region: nucleotides 385-702; and stop codon: nucleotides 703-705.

SEQ ID NO:4 is the FA5 antibody deduced light chain amino acid sequence (shown in FIG. 21), including the leader sequence: amino acids 1-19; FR1: amino acids 20-41; CDR1: amino acids 42-55; FR2: amino acids 56-70; CDR2: amino acids 71-77; FR3: amino acids 78-109; CDR3: amino acids 110-118; FR4: amino acids 119-128; and constant region: amino acids 129-234.

SEQ ID NO:5 is F04-A90585-406686-1-vh-G3-R234.a (1>633) in FIG. 24. It is identical to positions 1 to 593 of SEQ ID NO:1 except for one nucleotide.

SEQ ID NO:6 is G08-A90596-406686-1-CH-C16.ab1 (32>536) in FIG. 24. It is identical to positions 515 to 1019 of SEQ ID NO:1 except for one nucleotide.

SEQ ID NO:7 is H05-A90600-406686-1-CH-P258.ab1 (10>556) in FIG. 24. It is identical to positions 940 to 1404 of SEQ ID NO:1 except for one nucleotide. SEQ ID NO:8 is H12-A90608-406686-1-VL-M13-47.a(15>528) in FIG. 25. It is identical to positions 1 to 514 of SEQ ID NO:3 except for one nucleotide.

DETAILED DESCRIPTION OF THE INVENTION

The present invention concerns monoclonal antibodies and polyclonal antibodies that are specific for 4,6-diamino-5-(formylamino)pyrimidine (CAS 5122-36-1). This structure (also termed FAPY-A; FAPY-Ade, and FAPY-adenine) is formed in DNA bases by single electron oxidation reactions caused primarily by oxygen free radicals. Damage to DNA of this sort, along with its alternate product, 8-hydroxy-pyrimidine derivatives, can result in mutations from misreading if not first repaired. In the case of free radical oxidations of the DNA base Adenine, FAPY-A and 8-OH-A are alternate reaction products, with FAPY-A being exclusively formed under more reducing conditions and 8-OH-A being formed under more oxidative redox conditions. These different reaction products and their expression in biological tissues seem to correlate well with precancerous and cancerous changes in tissues. Thus, detection of FAPY-A and 8-OH-A via immunoassay (immunohistochemistry or ELISA) may be utilized to provide important future cancer risk information to individuals.

Chemical detection is the alternate method for detection and quantitation of these DNA base lesions. This is a labor-intensive process involving initial isolation of high purity DNA from tissues, hydrolysis, and derivitization of the DNA to provide a mixture of DNA bases that are separated and quantitated by gas chromatography-selected ion monitoring mass spectrometry. The cumbersome nature of this procedure limits the throughput of samples and is not suitable for assays of large numbers of DNA specimens. Another drawback is that it first requires isolation of DNA from tissues and thus information about the specific cell type that expressed most DNA base lesions is lost.

In contrast, antibody detection methods such as immunohistochemistry (IHC) and enzyme-linked immunosorbent assay (ELISA) are fast and do not depend on DNA purification from tissues. IHC can be used to identify the specific cell populations that express the DNA lesions. The ability to rapidly detect and quantitate levels of pro-mutagenic DNA damage with a low cost method will allow a level of DNA damage screening that would be impossible by chemical detection methods. This information can potentially be used in clinical environments in relation to cancer incidence and avoidance.

Production of a panel of antibodies specific for FAPY-A was accomplished through the chemical synthesis of a FAPY-A-hapten structure containing a linker group that could easily be coupled to free amino groups expressed on proteins or other carrier molecules. This molecule lacks the ribose or deoxyribose moiety found on nucleotides or deoxynucleotides of RNA or DNA so that antibodies obtained from immunization with it coupled to the carrier KLH can be expected to have high affinity for the FAPY-A base structure. Screening of hybridomas generated in fusions of spleen cells from immunized animals using instead a FAPY-A-BSA conjugate demonstrated both the simplicity and efficacy of this method for preparing anti-FAPY-A monoclonal antibodies. In fact, 35 wells in fusion plates with hybridomas expressing antibodies having FAPY-A specificity were obtained upon initial screening from which a subset of 5 were cloned by limiting dilution to yield monoclonal antibody producing hybridomas of both IgM and IgG isotypes. These antibodies are novel as there is currently no other anti-FAPY-A specific monoclonal or polyclonal antibodies known to exist.

The genes for the heavy and light chains for antibody FA5 were sequenced and the amino acid sequence for each chain was deduced. Methods are known to improve antibody specificity and affinity by, for example, in vivo or in vitro affinity maturation. A variety of antibody engineering methods also exist to modify the antibody sequence to adjust affinity and specificity. Additionally, antibody fragments having the same or similar specificity and affinity of the full size antibody can be prepared and applied to diagnostic and therapeutic uses. One can easily recognize that the methods disclosed herein for the production of anti-FAPY-A antibodies can be utilized for the production of additional antibody clones having the desired specificity, affinity, or isotype depending on the needs of the specific application. The antibodies disclosed herein are useful for the detection and quantitation of the FAPY-A structure when present in DNA of organisms. Methods to detect FAPY-A in DNA or RNA include but are not limited to immunohistochemistry of tissues, ELISA of DNA derived from tissues, capture of FAPY-A from biological fluids for detection and quantitation, or a variety of other diagnostic or therapeutic uses involving antibody binding with the FAPY-A structure.

The present invention is directed to materials and methods for detecting FAPY-adenine in a sample of nucleic acids obtained from a biological specimen using monoclonal or polyclonal antibodies. In one aspect of the present invention, monoclonal and polyclonal antibodies are provided that are characterized by their specific reactivity with FAPY-adenine. Representative embodiments of this aspect of the invention are the monoclonal antibodies identified below, produced by the hybridomas also identified below:

Hybridoma strain (designated as "Murine Hybridoma (FA5)" (ATCC Accession No. PTA-121431) was deposited with American Type Culture Collection (ATCC), P.O. Box 1549, Manassas, Va. 20108, USA, on Jul. 24, 2014. The subject hybridoma strain has been deposited under conditions that assure that access to the culture will be available during the pendency of this patent application to one determined by the Commissioner of Patents and Trademarks to be entitled thereto under 37 CFR §1.14 and 35 USC §122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject hybridoma deposit will be stored and made available to the public in accordance with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The preferred antibodies for use in the assays of the present invention are monoclonal antibodies FA1-FA5, which are reactive with FAPY-adenine.

Monoclonal antibodies of this invention can be prepared according to conventional methods by using FAPY-adenosine conjugated to a carrier protein as an immunogen, as described in Current Protocols in Immunology, John Wiley & Sons, Inc. New York, N.Y. (1994), incorporated herein by reference. The synthesis of FAPY-adenosine is described in Cho et al. (22).

To prepare the immunogen the FAPY-adenosine product can be readily coupled to carrier proteins through the available amino groups by methods known in the art, although other types of antigen carrying molecules may be used. In an embodiment of the present invention, FAPY-adenosine is coupled to keyhole limpet hemocyanin (KLH) by condensation of the carboxyl group on the linker of the FAPY-A hapten structure to an amino group on the protein using the water soluble carbodiimide EDC (1-Ethyl-3-(3-dimethylaminopropyl)carbodiimide). KLH is a suitable conjugation protein for such a coupling reaction since it aids in stimulating an immune response from attached ligands. Harlow et al., Antibodies, Cold Spring Harbor Laboratory (1988). Because of this, such an antigen is not useful for hybridoma screening. Other antigen carrier molecules which may be suitable for practicing the present invention include, but are not limited to BSA, ovalbumin, nucleic acids, lipids, carbohydrates, and naturally occurring biological conjugates such as glucuronic acid conjugates.

Immunization may be carried out according to conventional methods well known to those skilled in the art, such as by subcutaneously, intravenously or intraperitoneally injecting the FAPY-adenosine conjugated to a carrier protein into an animal. More specifically, the immunogen may be diluted with PBS or physiological saline to a suitable concentration, and then injected into the animal, together with a suitable adjuvant if necessary. The immunogen should be injected several times (3 to 5 times) at an interval of 7 to 10 days with 50 to 100 μg of immunogen in 0.1 ml total volume until the total volume injected reaches 100 μl per animal. A conventional carrier may be used for the injection. Spleen cells isolated from the animal three days after the completion of the injection of the FAPY-adenine conjugate are desirable for use as immune cells.

In an embodiment of the present invention balb/c mice are injected subcutaneously in multiple sites with FAPY-adenosine-KLH conjugate, prepared by mixing the immunogen with PBS and Freund's incomplete adjuvant followed by emulsification. The mice are immunized four times at ten day intervals with a total volume of 100 μl of immunogen per animal. Three days after fusion, spleen cells are then isolated for use as immune cells.

The transformed mammalian cells immunized by a FAPY-adenosine conjugate are then fused with mammal plasmacytoma to produce hybridomas. A clone recognizing FAPY-adenosine is selected from the hybridomas and the target monoclonal antibody is then obtained from the clone. In the above process, there are few limitations to the mammal cells to be transformed with the immune antigen. It is desired that the immune antigen be selected taking its compatibility with the mammal plasmacytoma be fused into consideration. Mice, rats, rabbits and the like are generally preferable for use.

Various known myeloma cells can be used as mammal plasmacytoma to be fused with the above immune cells. Such myeloma cells include, for example, p3 (pe/x63-Ag8) (*Nature*, 256:495-497 (1975)), P3-U1 (*Current Topics of Microbiology and Immunology*, 81:1-7 (1987)), NS-1 (*Eur. J. Immunol.*, 6:511-519 (1976)), MPC-11 (Cell, 8405-415 (1976)), PS2/0 (*Nature*, 276:269-270 (1978)), FO (*J. Immunol. Meth.*, 35:1-21 (1980)), x63, 6, 5, 3 (*J. Immunol.*, 123:1548-1550 (1979)), S194 (*J. Exp. Med*, 148:313-323 (1978)), and R210 (*Nature*, 277:131-133 (1979)) of rat, and the like. In one embodiment of the present invention, mouse X63 myeloma cells are used.

The fusion of the immune cell and the plasmacytoma can be carried out in accordance with known methods, (see Harlow et al. (1988)) in the presence of a fusion accelerator and in a conventional nutritious medium. Conventional fusion accelerators, such as polyethylene glycol (PEG) and sendai virus (HVJ) can be used. Optionally, adjuvants such as dimethylsulfoxide and the like may be used in order to promote the efficiency of the fusion. A conventional fusion ratio of about 1-10 immune cells per one plasmacytoma may be used. As a medium for the fusion, any medium used for the cultivation of the plasmacytoma, such as RPMI 1640 medium and MEM medium, as well as other various media used for the cultivation of this type of cell, can be used. Serum obtained by removing serum complement from fetal calf serum (FCS) is a typical example of the type of medium that may be used.

The fusion is carried out by thoroughly mixing a prescribed amount of the immune cells with the plasmacytoma and blending this mixture with a medium to which about 30-60% (w/v) of a PEG (e.g., PEG with an average molecular weight of 1,000-6,000) solution which has been heated to about 37° C. in advance is added. The cultivation in the HAT medium is continued for a period sufficient for cells other than hybridoma (such as unfused cells) to die, usually for several days to several weeks. The hybridoma obtained is then subjected to a conventional limiting dilution method to detect the target cell lines producing the antibody of interest. In a preferred method of the present invention, the hybridoma is subjected to limited dilution cloning containing $8 \times 10^5$ mouse thymocytes as feeder cells per well. RPMI medium with 10% FCS and 1 mM pyrovate and 2 mM glutamine thymocytes were used as feeder cells both for original fusion and in subcloning.

The detection of the antibody-producing cell lines of the present invention may be carried out according to standard methods commonly used for the detection of antibodies, as described in the laboratory manual by Harlow et al. (1988) cited elsewhere herein, for example. Standard methods commonly used include the ELISA method, the plaque method, the spot method, the agglomeration reaction method, the Ouchterlony method, the radio immunoassay (RIA), and the like. Use of FAPY-adenosine-conjugated BSA as an antigen for the detection is desirable.

Supernatant can be tested for binding to FAPY-adenosine conjugated BSA in a solid phase binding assay. The initial differential screening of the fusion can be conducted with a FAPY-adenosine-BSA conjugate versus an adenosine-BSA conjugate, along with BSA alone. Reactivity of FAPY-adenosine selected clones from two independent fusions with alternate antigens is analyzed.

Hybridomas that show reactive antibodies are further analyzed for binding specificity by comparing the reactivity of BSA conjugates linked to FAPY-adenosine, native base structure, alternate oxidative products, irrelevant bases and oxidized products and a negative control. Antibody-producing cell lines are screened to obtain those cell lines that generate antibody having binding specificity for FAPY-adenosine. Hybridomas producing target monoclonal antibodies of the invention can be cultivated over generations in conventional media and can be stored in liquid nitrogen.

Collection of monoclonal antibodies of the present invention from hybridomas of the invention can be performed by cultivating the hybridoma according to conventional methods and obtaining the monoclonal antibody as a supernatant, or by administering the hybridoma to a mammal with which the hybridoma is compatible, allowing the hybridoma to proliferate, and collecting the desired antibodies from the ascites fluid. The former method is adaptable to the production of high purity monoclonal antibody, and the latter to mass production of monoclonal antibody; monoclonal antibodies thus obtained may be purified by means of salting, gel filtration, affinity chromatography, or in accordance with other methods.

One aspect of the invention concerns a monoclonal or polyclonal antibody (full-length), or an antigen-binding fragment of the monoclonal or polyclonal antibody, having specific binding affinity for FAPY-adenine. In some embodiments, the antibody is a monoclonal antibody, or antigen-binding fragment thereof, and is produced by the hybridoma having American Type Culture Collection (ATCC) Deposit Designation PTA-121431, deposited with the ATCC on Jul. 24, 2014. In some embodiments, the antibody or antigen-binding fragment specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

In some embodiments, the antibody or antigen-binding fragment comprises:

(a) an immunoglobulin heavy chain variable region ($V_H$) comprising CDR1 sequence at least 80% identical to the CDR1 in FIG. 19 (amino acids 50-54 of SEQ ID NO:2), a CDR2 sequence at least 80% identical to the CDR2 sequence in FIG. 19 (amino acids 69-85 of SEQ ID NO:2), and a CDR3 at least 80% identical to the CDR3 sequence in FIG. 19 (amino acids 118-126 of SEQ ID NO:2); and/or (b) an immunoglobulin light chain variable region ($V_L$) comprising CDR1 sequence at least 80% identical to the CDR1 in FIG. 21 (amino acids 42-55 of SEQ ID NO:4), a CDR2 sequence at least 80% identical to the CDR2 sequence in FIG. 21 (amino acids 71-77), and a CDR3 at least 80% identical to the CDR3 sequence in FIG. 21 (amino acids 110-118).

In some embodiments, the antibody or antigen-binding fragment comprises:

(a) an immunoglobulin heavy chain variable region ($V_H$) comprising CDR1 sequence at least 90%, at least 95%, or 100% identical to the CDR1 in FIG. 19 (amino acids 50-54 of SEQ ID NO:2), a CDR2 sequence at least 90%, at least 95%, or 100% identical to the CDR2 sequence in FIG. 19 (amino acids 69-85 of SEQ ID NO:2), and a CDR3 at least 90%, at least 95%, or 100% identical to the CDR3 sequence in FIG. 19 (amino acids 118-126 of SEQ ID NO:2); and/or (b) an immunoglobulin light chain variable region ($V_L$) comprising CDR1 sequence at least 90%, at least 95%, or 100% identical to the CDR1 in FIG. 21 (amino acids 42-55 of SEQ ID NO:4), a CDR2 sequence at least 90%, at least 95%, or 100% identical to the CDR2 sequence in FIG. 21 (amino acids 71-77), and a CDR3 at least 90%, at least 95%, or 100% identical to the CDR3 sequence in FIG. 21 (amino acids 110-118).

In some embodiments, the antibody or antigen-binding fragment comprises:

(a) an immunoglobulin heavy chain variable region ($V_H$) comprising the CDR1 sequence in FIG. 19 (amino acids 50-54 of SEQ ID NO:2), the CDR2 sequence in FIG. 19 (amino acids 69-85 of SEQ ID NO:2), and the CDR3 sequence in FIG. 19 (amino acids 118-126 of SEQ ID NO:2); and/or (b) an immunoglobulin light chain variable region ($V_L$) comprising the CDR1 in FIG. 21 (amino acids 42-55 of SEQ ID NO:4), the CDR2 sequence in FIG. 21 (amino acids 71-77), and the CDR3 sequence in FIG. 21 (amino acids 110-118).

In some embodiments, an antibody of the invention comprises heavy and light chain variable regions comprising amino acid sequences that are homologous to the amino acid sequences of the preferred antibodies described herein, and wherein the antibodies retain the desired functional properties of the anti-FAPY-adenine antibodies of the invention. Optionally, the VH domain comprises amino acid modifications of one or more CDR residues, e.g., where the modifications essentially maintain or improve affinity of the antibody. For example, the antibody variant may have one, two, three, or from one to about seven amino acid substitutions in the above VH or VL CDR sequences. For example, the invention provides an isolated monoclonal antibody, or antigen-binding portion thereof, comprising a heavy chain variable region and a light chain variable region, wherein: (a) the VH region comprises an amino acid sequence that is at least 50%, 60%, 70%, 80% or 90% identical to an amino acid sequence identified in the Figures; (b) the VL region comprises an amino acid sequence that is at least 50%, 60%, 70%, 80% or 90% identical to an amino acid sequence identified in the Figures; (c) the antibody specifically binds to FAPY-adenine.

In other embodiments, the CDR, VH and/or VL, or constant region amino acid sequences may be 50%, 60%, 70%, 80%, 85%, 90%, 95%, 96%, 97%, 98% or 99% identical to the sequences set forth above. An antibody having CDR, VH and/or VL regions having high (i.e., 80% or greater) identity to the CDR, VH and/or VL, or constant region regions of the sequences set forth above, can be obtained by mutagenesis (e.g., site-directed or PCR-mediated mutagenesis) of nucleic acid molecules encoding the CDR, VH and/or VL of sequences provided herein, followed by testing of the encoded altered antibody for retained function (e.g., FAPY-adenine binding affinity).

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm in a sequence analysis software. Protein analysis software matches similar sequences using measures of similarity assigned to various substitutions, deletions and other modifications, including conservative amino acid substitutions.

The percent identity between two amino acid sequences can be determined, e.g., using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Polypeptide sequences can also be compared using FASTA, applying default or recommended parameters. A program in GCG Version 6.1., FASTA (e.g., FASTA2 and FASTA3) provides alignments and percent sequence identity of the regions of the best overlap between the query and search sequences (Pearson, *Methods Enzymol.* 1990; 183: 63-98; Pearson, *Methods Mol. Biol.* 2000; 132:185-219). The percent identity between two amino acid sequences can also be determined using the algorithm of E. Meyers and W. Miller (*Comput. Appl. Biosci.,* 1988; 11-17) which has been incorporated into the ALIGN program (version 2.0), using a PAM120 weight residue table, a gap length penalty of 12 and a gap penalty of 4.

Another algorithm for comparing a sequence to other sequences contained in a database is the computer program BLAST, especially blastp, using default parameters. See, e.g., Altschul et al., *J. Mol. Biol.* 1990; 215:403-410; Altschul et al., *Nucleic Acids Res.* 1997; 25:3389-402 (1997); each herein incorporated by reference. The protein sequences of the present invention can there be used as a "query sequence" to perform a search against public databases to, for example, identify related sequences. Such searches can be performed using the XBLAST program (version 2.0) of Altschul, et al. 1990 (supra). BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 (supra). When utilizing BLAST and Gapped BLAST programs, the default parameters of the respective programs (e.g., XBLAST and NBLAST) can be used. See www.ncbi.nlm.nih.gov.

Since nucleic acid sequences for the monoclonal FAPY-A antibody have been obtained, it is possible to produce monoclonal antibodies, or antigen-binding fragments thereof, by recombinant techniques. The plasmids described herein comprising the heavy and light chain nucleic acid sequence can be used for this purpose. Coding sequences could also be synthesized, cloned into an expression vector, and expressed in a host cell to produce the antibody or antigen-binding fragment.

The nucleic acid sequences encoding the antibody heavy and light chains can be inserted into any suitable vector. Specifically exemplified herein is the use of a plasmid as a vector. However, other vectors, such as viruses and DNA fragments, can also be used to express or produce this monoclonal antibody. Thus, other aspects of the invention include the recombinant FAPY-A antibodies (full-length), antigen-binding fragments, immunoconjugates comprising the recombinant antibodies or antigen-binding fragments, nucleic acids encoding the heavy and/or light chains, vectors comprising the aforementioned nucleic acid sequences encoding the heavy and/or light chains, and host cells comprising and, optionally, expressing the nucleic acid sequences, and methods for the production of the aforementioned materials.

The vector selected should be appropriate for the intended host cell. Examples of vectors for mammalian systems such as Chinese hamster ovary (CHO) cells or cells of the human embryonic kidney cell line, HEK293, include but are not limited to, pcDNA3.3-TOPO vector (Invitrogen) and GS Gene expression system (Lonza). Examples of vectors suitable for non-mammalian systems include, but are not limited to, pRSET for bacteria, pFastBac1 for insect cells, pYES2 for yeast cells, and tobacco mosaic virus vector for plant systems.

In the vector, the antibody open reading frames can be located downstream of a promoter. A promoter drives transcription of mRNA from the antibody open reading frames that include a start codon and a stop codon. The antibody heavy chain and light chain coding sequences (open reading frames) can be constructed within a single vector, but they can also be inserted into two independent vectors. The vector that encodes antibody nucleic acid sequences can be introduced into host cells, which then express the recombinant antibody or antigen-binding fragment.

Various types of cells can be used as host cells to express the antibodies or antigen-binding fragments. Because antibodies contain amino acid residues requiring glycosylation, mammalian cells are the ideal host cells because they provide glycosylation similar to the native antibodies. Among the most commonly used mammalian cells are CHO cells, mouse myeloma, and HEK293 cells, which may be utilized. In addition, many other mammalian cells can also be used to express the FAPY-A antibody or antigen-binding fragment thereof, and are also included in this invention as host cells for the production of this antibody.

Furthermore, non-mammalian cells may also be used to express or produce the antibody or antigen-binding fragment. The non-mammalian cells may be eukaryotic cells, including but not limited to plant cells, insect cells, and yeast cells. The non-mammalian cells may also be prokaryotic cells, including but not limited to bacteria and fungi.

The methods that may be used to introduce the vector encoding the antibody sequences into host cells include those widely used in molecular biology. For plasmid transfection, commonly used methods are electroporation and liposome-based transfection but other methods can also be used for the same purpose.

In addition to the preferred cell culture approach, other methods can also be used to produce the antibody or antigen-binding fragment. For example, the antibody may be expressed in the organs of transgenic animals, such as in animal mammalian glands, muscles, or eggs. Furthermore, the antibody or antigen-binding fragment can be expressed in transgenic plants, such the leaves of a transgenic plant, etc.

In some embodiments, the antibody is a polyclonal antibody, or antigen-binding fragment thereof. The generation of polyclonal antibodies is known to those skilled in the art and, for example, described in Harlow, E., and Lane, D., "Antibodies: A Laboratory Manual," Cold Spring Harbor Laboratory, Cold Spring Harbor, N.Y., (1988), which is incorporated by reference herein in its entirety. The polyclonal antibodies can be obtained from the serum of an animal, such as a rabbit, mouse, rat, or goat, immunized against a polypeptide according to the usual procedures. Animals are immunized with FAPY-adenine, or a portion of FAPY-adenine bearing an epitope on the base portion of FAPY-adenine, as the target antigen. At four-week intervals, the animals are treated with injections of the antigen, and bled 10 to 14 days later. After the third injection, the antiserum is examined in order to determine its ability to bind to the antigen, radiolabeled with iodine, prepared by the chloramine-T method, and is then purified by chromatography on a carboxymethylcellulose (CMC) ion exchange column. The antibody molecules are then collected from the animals and can be isolated to the desired concentration by methods well known to those skilled in the art, for example, using DEAE Sephadex to obtain an immunoglobulin fraction such as an IgG fraction.

To improve the specificity of the polyclonal serum, the antibodies can be purified by immunoaffinity chromatography using immunizing polypeptides in solid phase. The antibody is brought into contact with the immunizing antigen in solid phase for a sufficient amount of time so as to immunoreact the antigen with the antibody molecule in order to form an immunocomplex in solid phase.

The invention also includes compositions comprising an antibody, antigen-binding fragment thereof, or an immunoconjugate of the invention. In one embodiment, the composition is a pharmaceutical composition intended for administration to a human or animal subject, which further includes a pharmaceutically acceptable carrier.

Immunoconjugates

Another aspect of the invention is an immunoconjugate comprising the monoclonal antibody or antigen-binding fragment of the invention coupled to a moiety. In some embodiments, the moiety is covalently linked to the antibody or antibody fragment.

Any moiety capable of linkage may be linked to the antibody or antibody fragment. In some embodiments, the moiety is a biologically active agent, such as a small molecule drug or biologically active biologic molecule.

For example, the moiety may be an immune-stimulating carrier molecule; nanoparticle; detectable label (e.g., a fluorescent tag or radiolabel); drug (e.g., anti-cancer agent such as a chemotherapeutic drug); toxin; chelating agent; biotinylated moiety; tumor targeting agent (e.g., alkylphosphocholine (APC) molecule), protein transduction domain or membrane permeating peptide (e.g., Antennapedia PTD or HIV-1 Tat protein) to make the antibody or antibody fragment a cell-permeable antibody; another antibody or antibody fragment; or part of a solid support. More than one moiety may be linked to the antibody or antibody fragment.

In some embodiments, the moiety is an anti-cancer agent such as a chemotherapeutic agent or immunotherapeutic agent.

As described above, the antibodies and antibody fragments described herein can be linked (also referred to herein as "coupled") to another moiety to produce an immunoconjugate. The moiety may be a moiety in isolation or the moiety may be part of a molecule, which may be a molecule in isolation or a molecule that is part of a larger structure. Non-limiting examples include another peptide or protein (albumin, another antibody, etc.), toxins, radioisotopes, cytotoxic agents or cytostatic agents. The terms "linked" or "coupled" relates to the chemical linking or covalent attachment of another molecule/moiety by recombinant methods. Antibodies disclosed herein may also be linked to one or more non-proteinaceous polymers, e.g., polyethylene glycol, polypropylene glycol, or polyoxyalkylenes (see, for example, U.S. Pat. Nos. 4,791,192; 4,766,106; 4,670,417; 4,640,835; 4,609,546; 4,496,689; 4,495,285; 4,301,144; and 4,179,337, which are each hereby incorporated by reference in their entireties).

A stable link between the antibody or antibody fragment and the moiety can be achieved by use of a linker. Linkers are based on chemical motifs such as disulfides, hydrazones or peptides (cleavable), or thioethers (noncleavable) and, in therapeutic contexts, can control the distribution and delivery of the conjugate to the target cell. Cleavable or non-cleavable linkers can be used. Cleavable linkers may be selected to be catalyzed by enzymes in the target microenvironment (e.g., cancer cell) where it releases the moiety as a payload (e.g., a cytotoxic agent). (see, for example, Kovtun, et al., "Cell killing by antibody-drug conjugates," *Cancer Letters*, 2007, 255(2):232-40; Bąchor et al., "New method of peptide cleavage based on Edman degradation". *Molecular Diversity*, 2013, 17(3):605-11; Axup et al., "Synthesis of site-specific antibody-drug conjugates using unnatural amino acids", *PNAS*, 2012, 109(40):16101-6; Wulbrand et al., "Alpha-particle emitting 213Bi-anti-EGFR immunoconjugates eradicate tumor cells independent of oxygenation", PLoS ONE, 2013, 8(5): e64730; and Cardoso et al., "Antibody-conjugated nanoparticles for therapeutic applications", *Current Medicinal Chemistry*, 2012, 19 (19): 3103-27).

Antibodies and antibody fragments of conjugates can be labeled with various trivalent radiometals for imaging or targeted radionuclide-therapy applications. The antibody or antibody fragment is first conjugated to a chelating agent that is able to form stable complexes with the radionuclide of interest. This conjugation step can be carried out as part of the solid-phase peptide synthesis, or it can be undertaken in the solution phase after synthesis and purification of the peptide. The chelating agent 1,4,7,10-tetraazacyclododecane-1,4,7,10-tetraacetic acid (DOTA) may be used as the complexing agent. For example, radionuclides $^{177}$Lu and $^{90}$Y may be for therapeutic applications. Radionuclides $^{111}$In or 99m-Tc may be used for imaging the conjugate within a subject. Various imaging agents may be coupled to the antibody or antibody fragment, with or without a further therapeutic agent, to facilitate imaging of the immunoconjugate within a subject.

In the context of cancer, there are both live cells and necrotic cells in tumors. Dead cells expose nuclear DNA, which may be partially denatured, thus exposing the FAPY-A antigen for binding by the immunoconjugate. Thus, for example, an immunoconjugate comprising an antibody, or antibody fragment thereof, coupled to a radiolabel, cytotoxic drug, or toxin, could kill live cancer cells through a bystander effect, resulting in a therapeutic benefit. Advantageously, the antibody or antibody fragment of the conjugate would effectively ignore live cells and only bind to areas of dead cells, avoiding undesired side effects on normal tissues. In another embodiment, the moiety may be a gold nanoparticle and the immunoconjugate is administered to a subject with cancer for photothermal cancer therapy or radiofrequency therapy.

In some embodiments, the moiety coupled to the antibody or antibody fragment is the moiety of a metallic nanoparticle, such as a gold nanoparticle. In some embodiments, the moiety coupled to the antibody or antibody fragment is the moiety of a magnetic nanoparticle. Magnetic materials transduce energy when exposed to a magnetic field of sufficient intensity; for example, an alternating magnetic field will induce an alternating current in the particle, producing heat. The magnetic nanoparticles, which when placed in a magnetic field, are selectively heated at a certain frequency of the magnetic field, as a function of their size, composition, or both. The nanoparticles may be used for selective nanoparticle heating and applications thereof, hyperthermia induction in cells or tissue, remote alteration of protein structure and/or drug delivery (see, for example, U.S. Patent Application Publication No. 20070164250 (Hamad-Schifferli et al.), which is incorporated herein by reference in its entirety). Metal or magnetic materials, such as $Fe_3O_4$, $Fe_2O_3$, silver, copper, platinum, palladium may be used for the nanoparticles. In another embodiment, the nanoparticles are made from $TiO_2$, $CeO_2$, Silver, CuO, yttrium aluminum garnet (YAG), $InO_2$, CdS, $ZrO_2$, or a combination thereof. Any metal oxide, metal alloy, metal carbide, transit metal, may be used. In some embodiments, the particles are coated, such that the coating does not alter their respective responsiveness to the applied field. In another embodiment, the nanoparticles are of magnetic materials. In another embodiment, they are made of paramagnetic or superparamagnetic materials.

The moiety coupled to the antibody or antibody fragment may be a targeting agent that targets the immunconjugate to a desired anatomical site, such as a tumor.

The moiety coupled to the antibody or antibody fragment can be an agent for making target cells permeable to the conjugate, such as a protein transduction domain (see, for example, Harada et al., *Breast Cancer*, 2006, "Antitumor protein therapy; Application of the protein transduction domain to the development of a protein drug for cancer treatment", Volume 13, Issue 1, pp 16-26). Examples include human immunodeficiency virus-1 TAT, *Drosophila Antennapedia* (Antp), herpes simplex virus-1 VP22, and the polyarginines, are peptide sequences that are able to cross the cell membrane and enter cells, and deliver covalently bound cargo molecules such as peptides, proteins, and nucleic acids into cells.

The antibody or antibody fragment can be bound to a solid support or conjugated with a detectable moiety or be both bound and conjugated as is well known in the art. (For a general discussion of conjugation of fluorescent or enzymatic moieties, see Johnstone & Thorpe, Immunochemistry in Practice, Blackwell Scientific Publications, Oxford, 1982.) The binding of antibodies to a solid support is also well known in the art (see for a general discussion Harlow & Lane Antibodies: A Laboratory Manual, Cold Spring Harbor Laboratory Publications, New York, 1988 and Borrebaeck, Antibody Engineering—A Practical Guide, W.H. Freeman and Co., 1992). The detectable moieties contemplated with the present invention include radiolabels and enzymes, for example. Specific examples of detectable labels include, but are not limited to, fluorescent labels, metallic labels, gold, ferritin, alkaline phosphatase, beta-galactosidase, peroxidase (e.g., horse radish peroxidase), urease, fluorescein, rhodamine, tritium, and iodination. Other types of detectable labels include chemical moieties such as biotin, which may be detected via binding to a specific cognate detectable moiety, e.g., labeled avidin.

Immunoconjugates including detectable moieties may be used in in vitro and in vivo diagnostic and therapeutic methods. For example, immunoconjugates of the invention may be utilized as the antibody or antibody fragment in the assays of the invention.

Assays

The antibodies and antigen-binding fragments of the present invention can be used to detect and quantitate (e.g., by use of a standard curve) the presence of FAPY-adenine in biological specimens of DNA. Procedures for doing this would include immobilizing the DNA, denaturing it to disrupt the base-pairing scheme exposing the free base structures, and quantitating the amount of FAPY-Ade present per amount of DNA in a quantitative immunoassay similar to those described below.

The presence of FAPY-Ade in a biological specimen can be analyzed at a high sensitivity and precision and with a high specificity in a simple manner by the use of antibodies and antigen-binding fragments of the invention in conventional immunoassay formats, such as enzymatic immunoassays EIA), enzyme-linked immunosorbent assays (ELISA), immunohistochemistry (IHC), immunoprecipitation, immunoelectrophoresis, dipstick (antibody, antigen-binding fragment, or immunoconjugate coupled to a solid support), radioimmunometric assays (RIA), immunoturbidimetric assays, or others known in the prior art. The lab manual by Harlow et al. (1988) discusses many of these methods. Because the antibodies of the present invention react with FAPY-Ade with specificity they are useful for the determination of FAPY-Ade in clinical samples by immunoassay, thus enabling screening for various diseases and exposure to toxicants associated with elevated levels of FAPY-Ade and associated with mutagenesis resulting from oxidative DNA damage. Thus, the present invention further provides immunoassay methods for determining the presence or amount of FAPY-Ade in a biological fluid specimen using the antibodies or antigen-binding fragment of the invention. The assay comprises immunochemical reagents for forming an immunoreaction product whose presence or amount relates, either directly or indirectly, to the presence or amount of FAPY-Ade in the sample. Those skilled in the art will appreciate that there are numerous well known clinical diagnostic procedures in which the immunochemical reagents of this invention can be used to form an immunoreaction product whose presence and/or amount relates to the presence and/or amount of FAPY-Ade present in a sample. While exemplary assay methods are exemplified herein, the invention is not limited to these. Various heterogeneous and homogenous protocols, either competitive or noncompetitive, can be employed in performing an assay of this invention.

For example, the antibodies of the present invention can be used in a direct solid phase immunoassay of antigen present in a biological specimen. DNA can be extracted from a tissue, cell or urine, for example, and subjected to a solid phase assay under conditions where the results with known amounts of DNA (e.g., by weight) are compared to a standard curve containing known amounts of antigen. This methodology could also be applied to impure DNA fractions or unfractionated biological specimens such as tissue, cells, or bodily fluid and the results normalized to another parameter such as protein concentration or nucleic acid using alternate means for determining the amount of nucleic acid present in the specimen (e.g., the amount of adenine present).

Furthermore, the antibodies and antigen-binding fragments of the present invention can be used in a quantitative immunohistochemical analysis of cells and tissues. For example, cells or tissue sections can be immobilized on glass slides or other supports under conditions which denature the cellular DNA, such as heating or drying the specimen. Analysis can be conducted with, for example, fluorescently or otherwise labeled FAPY-Ade specific antibodies or antigen-binding fragments of the antibodies under conditions where the fluorescence intensity of the stained sections is proportional to the amount of FAPY-Ade present in the specimen.

In other embodiments, the FAPY-Ade specific antibodies or antigen-binding fragments can be immobilized and used to absorb or capture soluble antigen from known amounts of biological specimens such as cells, tissue, and fluids, including bodily fluids. This can be used as a concentration step prior to elution and a detection and quantitation step using other methodologies. In addition, a detection and quantitation step involving inhibition of antibody or antibody fragment binding to antigen as discussed below could be applied.

Furthermore, soluble antigen present in known amounts of biological specimens, including bodily fluids, can be detected and quantitated either directly or after an initial concentration step by determining the amount of this material required to provide inhibition of antibody binding to immobilized antigen. In these procedures, the specimen would be combined with antibody or antibody fragment of the present invention and incubated for a period of time sufficient to allow antibody or antibody fragment complexes to form with the soluble antigen. The resulting mixture would be incubated with immobilized antigen and the amount of antibody or antibody fragment binding to the immobilized antigen determined. The concentration of antigen present in the specimen would be determined by comparison to the effect with known amounts of FAPY-Ade containing soluble fractions in either single determinations or in serial dilutions of the specimen. The dilution state required to relieve the inhibition of binding to the immobilized antigen to a proscribed level would be proportional to the concentration of FAPY-Ade present in the specimen.

In another embodiment, the immunoassay utilized is the surface plasmon resonance (SPR) assay (see, for example, Mullett W M et al., "Surface plasmon resonance-based immunoassays," *Methods*, 2000, 22(1):77-91, which his incorporated herein by reference in its entirety).

In another illustrative embodiment, a double antibody or "sandwich" immunoassay format may be employed comprising the steps of (a) forming a first immunoreaction admixture by admixing a sample with a first antibody or antigen-binding fragment thereof, e.g., a monoclonal antibody, wherein the antibody or fragment and FAPY-Ade present in the sample are capable of forming a first immunoreaction product (the first antibody or fragment can be coupled to a solid matrix); (b) maintaining the first immunoreaction admixture so formed under biological assay conditions for a time period sufficient to form the first immunoreaction product (the first immunoreaction product can then be separated from the sample); (c) forming a second immunoreaction admixture by admixing the first immunoreaction product with a second antibody or fragment, monoclonal or polyclonal, which recognizes FAPY-Ade; (d) maintaining the second immunoreaction admixture so formed under biological assay conditions for a period sufficient to form the second or "sandwich" immunoreaction product; and (e) determining the presence and, optionally, the amount of second immunoreaction product formed, and thereby the presence and, optionally, the amount of FAPY-Ade in the sample. Preferably, the second antibody is labeled, such as with with an enzyme, and thus the second immunoreaction product formed will be a labeled product to facilitate determination of the second immunoreaction product.

In preferred double antibody assay methods, the amount of immunoreaction product determined is related to the amount of immunoreaction product similarly formed and determined using a standard sample in place of the biological sample wherein the standard sample contains a known amount of FAPY-Ade in accordance with this invention. Alternatively, a synthetic secondary standard can be used.

It is also preferred that the second antibody or antibody fragment be directed to a site on the FAPY-Ade which is not the same as the site to which the first antibody or antibody fragment is directed. For example, the first antibody or antibody fragment can be directed to a site other than that which reacts with the antibodies of the present invention.

In any of the illustrative assays, the biological sample can be provided as a known or unknown quantity of urine, semen, seminal fluid, synovial fluid, saliva, exhaled breath condensate, tissue, blood, or a blood derived product such as serum or plasma. Samples for study of oxidative DNA damage generally come from two main sources: urinary excretions of oxidized nucleosides and bases from DNA isolated target tissue or cells, such as lymphocytes. Examples of tissue samples include but are not limited to breast, liver, prostate, testes, brain, and skin. First, the DNA in the specimen must be immobilized, and then denatured to disrupt the base pairing scheme, exposing the tree base structures. The amount of antibody used can be known or unknown. The admixture is maintained under biological assay conditions for a predetermined period of from about 1 hour to about 16 hours at a temperature of from about 4° C. to about 37° C., such as about 22° C.

Biological assay conditions are those that maintain the biological activity of the immunochemical reagents of this invention and the FAPY-Ade. Those conditions can generally include a temperature range of from about 4° C. to about 37° C., a pH value range of from at least about 6.0 to about 8.0, with a preferred range of 7.0 to 7.4, and an ionic strength varying from about 50 mM to 500 mM. Upon routine experimentation, other biological assay conditions may be learned. Methods for optimizing such conditions are well known to those skilled in the art.

Another assay format that may be used in practicing the present invention is the precipitation assay. In this embodiment, the process comprises formation of an immunoreaction admixture by admixing a DNA sample obtained from a biological specimen with an antibody or antigen-binding fragment of the invention to yield a precipitous immunoreaction product. The antibody or antibody fragment can be operatively linked to a solid particulate such as a microparticle or bead, such that when antibody-antigen cross-linking occurs, the particulate matter aggregates, indicating the presence of the target material.

Another method that may be utilized is immunoturbidimetry because of its adaptability to automatic analysis, enabling a large number of samples to be measured at one time. Specifically, an amount of FAPY-Ade in a sample of DNA obtained from urine, blood, or the like can be determined by adding one or more of the antibodies or antigen-binding fragments thereof of the present invention to the sample for the reaction and by measuring changes in the absorbance before and after the reaction.

In some embodiments, a cell/tissue specimen is examined by tissue microarrays (TMA). For example, multiple tissue samples may be taken from multiple such tissue specimens, and the multiple samples from a particular specimen are similarly placed at corresponding positions in the multiple supports. Each of the resulting supports contains an array of tissue samples from multiple specimens, in which corresponding positions in each of the arrays represent tissue samples from the same tissue specimen. In particular examples, each support is then sectioned into multiple similar sections with samples from the same tissue specimen at corresponding positions of the sequential sections. The different sections may then be subjected to different reactions, such as exposure to different histological stains or molecular markers, so that the multiple "copies" of the tissue microarrays can be compared for the presence of reactants of interest, such as FAPY-Ade. The large number of tissue samples, which are repeated in each of a potentially large number of sections of multiple substrates, can be exposed to as many different reactions as there are sections. For example, about 100,000 array sections may be obtained from a set of 1000 tissue specimens measuring 15×15×3 mm. This approach provides for high-throughput techniques, including rapid parallel analysis of many different tissue specimens.

In one embodiment, a sample can be processed by exposing different cut sections on the array to different biological reagents (such as standard stains, or immunohistochemical or genetic markers, oligonucleotides probes/primers, peptides, polypeptides, ligands, and small molecules, hormones, lipids, carbohydrates, lectins, etc.) that recognize biological structures in the cut sections. An imager then obtains an image of the cut processed sections, and an image processor identifies regions of the cut sections that contain images of biological interest (such as evidence of gene copy numbers), and stores images of the cut sections. If desired, quantities of biological reagents such as FAPY-Ade can be detected to quantify reactions, or to determine the distribution of the reagent in the sample.

Many other types of assays within the scope of this invention will be readily apparent to those skilled in the art.

Kits

The antibodies and antibody fragments of the present invention may form part of a kit comprising the antibody or antibody fragment of the invention and an agent for detecting an immunoreaction product comprising FAPY-Ade and the antibody or antibody fragment. Instructions for use of a packaged immunochemical reagent are also typically included in such a kit.

As used herein, the term "packaged" can refer to the use of a solid matrix or material such as glass, plastic, paper, fiber, foil and the like capable of holding within fixed limits an antibody of this invention. Thus, for example, a package can be a glass vial used to contain monoclonal milligram quantities of antibody of the present invention, or it can be a microliter plate well to which microgram quantities of a contemplated antibody has been operatively affixed. Alternatively, a package could include antibody-coated or antibody-fragment coated microparticles entrapped within a porous membrane or embedded in a test strip or dipstick, etc. Alternatively, the antibody or antibody fragment can be directly coated onto a membrane, test strip or dipstick, etc. which contacts the sample fluid. Many other possibilities exist and will be readily recognized by those skilled in this art.

Instructions for use typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an antibody or antibody fragment of the present invention.

The term "complex" as used herein refers to the product of a specific binding reaction such as an antibody-antigen, antibody fragment-antigen, or receptor-ligand reaction. Exemplary complexes are immunoreaction products.

As used herein, the terms "label", "detectable label", "labeling agent" in their various grammatical forms refers to single atoms and molecules that are either directly or indirectly involved in the production of a detectable signal to indicate the presence of a complex. Any label or indicating agent can be linked to or incorporated in an expressed protein, peptide, or antibody molecule that is part of the present invention, or used separately, and those atoms or molecules can be used alone or in conjunction with additional reagents. Such labels are themselves well known in the diagnostic art.

The label can be a fluorescent labeling agent that chemically binds to antibodies, antibody fragments, or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-diethylamine-1-natpthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis," *Antibody As a Tool*, Marchalonis et al., Eds., John Wiley & Sons, Ltd., pp. 189-231 (1982).

The indicating group may also be an enzyme such as horseradish peroxidase (HRP), glucose oxidase, or the like. In such cases where the principle indicating group is an enzyme such as HRP or glucose oxidase, additional reagents are required to indicate that a receptor-ligand complex (immunoreactant) has formed. Such additional reagents for HRP include hydrogen peroxide and an oxidation dye precursor such as diaminobenzidine. An additional reagent useful with glucose oxidase is 2,2,-azino-di-(3-ethyl-benz-thiazoline-G-sulfonic acid) (ABTS).

Radioactive elements are also useful labeling agents and may be used in practicing the present invention. An exemplary radiolabeling agent is a radioactive element that produces gamma ray emissions. Elements which themselves emit gamma rays, such as $^{124}I$, $^{125}I$, $^{128}I$, $^{132}I$ and $^{1}Cr$ represent one class of gamma ray emission-producing radioactive element indicating groups. Another group of useful labeling agents are those elements such as 1C, $^{18}F$, $^{15}O$ and $^{13}N$ which themselves emit positrons. Also useful is a beta emitter, such as $^{111}$indium or 3H. The linking of labels, i.e., labeling of peptides and proteins, is well known in the art. For instance, monoclonal antibodies produced by a hybridoma, or antigen-binding fragments of such antibodies, can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are also applicable. See, for example, Aurameas et al., *Scand. J Immunol.*, 8(7):7-23 (1978); Rodwell et al., *Biotech.*, 3:889-894 (1984); and U.S. Pat. No. 4,493,795.

The diagnostic test kit can also include, preferably as a separate package, a "specific binding agent," which is a molecular entity capable of selectively binding an antibody or antibody fragment of this invention or a complex containing such a species, but is not itself an antibody or antibody fragment of this invention. Exemplary specific binding agents are second antibody molecules or antibody fragments, complement, proteins or fragments thereof. Preferably the specific binding agent binds the antibody when it is present as part of a complex.

In some embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a complex.

The diagnostic kits of the present invention can be used in an "ELISA" format to detect the quantity of FAPY-Ade in biological samples of DNA obtained from biological specimens such as cells, plasma, saliva, serum, semen, synovial fluid, breath condensate, seminal fluid tissue, urine, or blood. "ELISA" refers to an enzyme linked immunosorbent assay such as those discussed above, which employ an antibody, antibody fragment, or antigen bound to a solid phase and an enzyme-antigen or enzyme-antibody conjugate to detect and quantify the amount of an antigen present in a sample.

Thus, in some embodiments, an antibody, or antigen-binding fragment thereof, with inherent specificity for FAPY-Ade can be affixed to a solid matrix to form a solid support. A reagent is typically affixed to a solid matrix by adsorption from an aqueous medium, although other modes of affixation applicable to proteins and peptides well known to those skilled in the art can be used.

Solid matrices useful as supports are also well known in the art. Such materials are water insoluble and include the cross-linked dextran available under the trademark SEPHADEX (Pharmacia Fine Chemicals, Piscataway, N.J.); agarose; polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

An example of a kit may include an antibody or antigen-binding fragment attached to a support (e.g., a dipstick). The support is then applied to a sample from a patient or to a surface that may contain FAPY-adenine and the surface of the substrate is then processed to assess whether specific binding occurs between the antibody or antibody fragment and FAPY-adenine within the sample. As will be understood by one of skill in the art, such binding assays may also be performed with a sample or object contacted with an antibody or antigen-binding fragment thereof and/or FAPYP-adenine that is in solution, for example in a 96-well plate or applied directly to an object surface.

The immunoreagents of any diagnostic system described herein can be provided in solution, as a liquid dispersion or as a substantially dry powder, e.g., in lyophilized form. Where the indicating agent is an enzyme, the enzyme's substrate can also be provided in a separate package. A solid support such as the above-described microtiter plate and one or more buffers can also be included as separately packaged elements in the diagnostic assay systems of this invention.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

Thus, the antibodies, antibody fragments, and immuno-conjugates of the present invention may be used in a variety of immunoassays to detect and quantitate FAPY-Ade in biological specimens. These assays may be useful for research, diagnosis of disease, prognosis and tracking of response to treatment. The following examples illustrate methods for making the antibodies of the present invention. Optionally, the methods of the invention can further include and utilize antibodies and antigen-binding fragments thereof that have binding affinity for 8-OH-A, the alternative product of the single electron oxidation reactions caused primarily by oxygen free radicals. Such antibodies, and methods for their use, are described in U.S. Pat. No. 6,187,551 (Holmes et al.) and U.S. Pat. No. 6,900,291 (Holmes et al.), which are incorporated herein by reference in their entirety.

The methods of the invention include methods for the diagnosis, monitoring the status of, and treating the onset of cancers and other diseases associated with elevated levels of FAPY-adenine. In some embodiments, the method for diagnosing or monitoring the status of a disease associated with elevated levels of FAPY-adenine in a human or animal subject, comprises the steps of:

a. contacting a biological specimen of nucleic acids from the human or animal subject with the antibody or antigen-binding fragment of or immunoconjugate of the invention to form a complex of: (i) antibody, antigen-binding fragment, or immunoconjugate, and (ii) FAPY-adenine; and b. determining the amount of complex formed as a measure of the presence or amount of FAPY-adenine in the specimen, wherein the amount of complex determined is indicative of the status of a disease associated with elevated levels of FAPY-adenine or is correlated with the status of a disease associated with elevated levels of FAPY-adenine.

Diseases caused, or exacerbated, by oxidative stress may be diagnosed or monitored. The disease may be cancer; Alzheimer's disease, Parkinson's disease, multiple sclerosis, amyolotrophic lateral sclerosis, or other neurodegenerative disease; emphysema or other chronic obstructive pulmonary disease (COPD); or diabetes, cardiovascular disease, autoimmune disease, or other age-related disease.

The methods may further comprise treating the disease by administering an agent or other treatment that alleviates one or more symptoms of the disease. In some embodiments, the agent comprises an antibody, antigen-binding fragment, or immunoconjugate of the invention.

In some embodiments, the method for diagnosing or monitoring the status of a disease associated with elevated levels of FAPY-adenine in a human or animal subject, is a method of assessing cancer risk in a human or animal subject based on the relationship between a 8-hydroxy-purine and a formamidopyrimidine-purine (FAPY-purine). Thus, the difference in base damage amounts (8-hydroxy purine versus FAPY-purine) may be used to create a comparative ratio to assess cancer risk.

FIGS. 31A-31C show results of immunohistochemistry of English sole kidney tissue with antibodies 8A6 specific for 8-hydroxy-adenine (gG1), 8G14 specific for 8-hydroxy-guanine (IgM), and FA5 specific for FAPY-adenine (IgG3). The tissue was derived from a 7 year old English sole from Eagle Harbor, Puget Sound, Wash. Eagle Harbor is known for aromatic hydrocarbon contaminated sediments and is associated with a high incidence of liver cancer in fish inhabiting that location. A tissue from an exposed animal was necessary to see positive staining given that the staining would be weak or negative in tissue from a normal or non-exposed organism. Although each antibody is detecting a different structure that is derived from the same process (free radical attack on DNA), the same type of staining results were observed, as would be expected.

Antibodies specific for three distinct yet related damaged DNA bases were tested on English sole tissue. These DNA lesions are caused by single electron (free radical) oxidation reactions with either adenine or guanine. The staining profile for each antibody is similar and indicative of focal expression of cells containing altered DNA bases. Such focal expression of markers associated with precancerous conditions is frequently observed in animal tissues after exposures to toxicants. These results demonstrate consistent staining properties of the antibodies and that the antibody FA5 is well suited for detection of the FAPY-A lesion in tissues by immunohistochemistry.

Positive staining in histologically normal tissue in fish inhabiting contaminated waterways is indicative of DNA damage resulting from such exposure. In contrast, immunohistochemistry of tissues from animals inhabiting clean reference waterways demonstrates weak or no staining with the same panel of antibodies. This profile (high expression in exposed animals and weak or negative expression in control unexposed animals) is consistent with results obtained using chemical detection methods. Thus, immunohistochemistry using the FA5 antibody as well as other antibodies specific for other DNA base lesions is useful to characterize the amount of pro-mutagenic DNA base damage present in an organism. This information can be used to assess a potential risk for future cancer incidence in an organism given the known mutagenic potential of oxidative DNA base lesions such as 8-hydroxy-adenine, 8-hydroxy-guanine and FAPY-adenine. Such a risk analysis would involve of oxidized DNA bases using immunoassay methods such as immunochemical/immunohistochemical quantitation. This could include, for example, determining the expression ratio of the amount of one or more 8-hydroxy-purine products to the amount of one or more FAPY-purine products. The formation of 8-hydroxy-purine products is favored under oxidative conditions in tissues and the formation of ring-opening FAPY-purine products is favored under more reducing conditions. Generally, cancerous or precancerous tissues have a more oxidative redox status compared to a more reductive redox status of normal tissues. Thus, the amount and identity of oxidative DNA base lesions can provide useful information related to the future risk of an organism developing cancer. Altering the tissue redox status using one or more antioxidants can reduce the amount of DNA damage in an organism's tissues.

In some embodiments, the method of assessing cancer risk comprises:

comparing the measured amount of an 8-hydroxy-purine (such as 8-hydroxy-adenine, 8-hydroxy-guanine, or both) in a biological specimen obtained from the human or animal subject to the measured amount of a FAPY-purine (such as FAPY-adenine) in a biological specimen obtained from the human or animal subject. This comparison can provide a ratio or score related to the risk that the subject will develop cancer in the future, wherein a higher measured amount of 8-hydroxy-purine relative to the measured amount of FAPY-purine is indicative of an increased risk of developing cancer, and wherein a higher measured amount of FAPY-purine relative to the measured amount of 8-hydroxy-purine is indicative of a lower risk of developing cancer.

The 8-hydroxy-purine and FAPY-purine can be measured in the same specimen or separate specimens. If measured in separate specimens, the specimens are preferably the same type of specimen (e.g., blood specimens, or specimens from the same tissue).

The amount of 8-hydroxy-purine and/or FAPY-purine can be measured using various assays and assay formats. For example, the amount of 8-hydroxy-purine and/or FAPY-purine can be measured by a method selected from the group consisting of enzyme-linked immunosorbent assay (ELISA), immunochemistry, immunohistochemistry (IHC), immunoprecipitation, immunoelectrophoresis, dipstick (antibody, antigen-binding fragment, or immunoconjugate, coupled to a solid support), radioimmunoassay (MA), photochemical assay, and fluorescence assay.

In some embodiments, the FAPY purine is FAPY-adenine. FAPY-adenine may be measured using an antibody, antigen-binding fragment, or immunoconjugate of the invention. In some embodiments, the antibody or antigen-binding fragment is obtained from the hybridoma having American Type Culture Collection (ATCC) Deposit Designation PTA-121431, deposited with the ATCC on Jul. 24, 2014.

In some embodiments, the measured amount of 8-hydroxy-purine is a measured amount of 8-hydroxy-adenine, a measured amount of 8-hydroxy-guanine, or both.

Antibodies useful for measuring 8-hydroxy-purine, and methods for their use, are described in U.S. Pat. No. 6,187,551 (Holmes et al.) and U.S. Pat. No. 6,900,291 (Holmes et al.), which are incorporated by reference herein.

In some embodiments, the amount of FAPY-purine is measured by:

a. contacting the biological specimen with an antibody, antigen-binding fragment, or an immunoconjugate disclosed herein, to form a complex of: (i) antibody, antigen-binding fragment, or immunoconjugate, and (ii) epitope, and b. determining the amount of complex formed as a measure of the amount of epitope in the biological specimen.

In some embodiments, the amount of 8-hydroxy-purine is measured by:

a. contacting the biological specimen with the antibody, antigen-binding fragment, or immunoconjugate having specific binding affinity for the 8-hydroxy-purine, to form a complex of: (i) antibody, antigen-binding fragment, or immunoconjugate, and (ii) epitope, and b. determining the amount of complex formed as a measure of the amount of epitope in the biological specimen.

Optionally, the comparing step can involve electronically comparing in a computer values reflective of the measured amount of 8-hydroxy-purine and FAPY-purine.

The biological specimen from a human or animal subject may be selected from among cells, tissue, blood, saliva, serum, plasma, synovial fluid, exhaled breath condensate, semen, seminal fluid, and urine, for example. In some embodiments, the biological specimen is a tissue specimen.

The method may further include the step of obtaining the sample from the subject and/or the step of measuring the 8-hydroxy-purine(s) and FAPY-purine in the sample.

Cancers within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain.

Representative cancer types that can be the diagnosed, monitored, and/or treated in accordance with the methods of the invention include, but are not limited to, those listed in Table 1.

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |

| | |
|---|---|
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, Childhood | Oral Cavity Cancer, Lip and Oropharyngeal Cancer |
| Germ Cell Tumor, Extragonadal | Osteosarcoma/Malignant Fibrous |
| Germ Cell Tumor, Ovarian | Histiocytoma of Bone |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral Astrocytoma | Ovarian Low Malignant Potential Tumor |
| | Pancreatic Cancer |
| Glioma, Childhood Visual Pathway and Hypothalamic | Pancreatic Cancer, Childhood |
| | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive |
| Soft Tissue Sarcoma, Childhood | Neuroectodermal Tumors, Childhood |
| Squamous Cell Carcinoma, see Skin Cancer (non-Melanoma) | Pituitary Tumor |
| | Plasma Cell Neoplasm/Multiple Myeloma |
| Squamous Neck Cancer with Occult Primary, Metastatic | Pleuropulmonary Blastoma |
| | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The term "tumor" is inclusive of solid tumors and non-solid tumors.

Treatments

Another aspect of the invention concerns a method for binding FAPY-adenine in a human or animal subject, comprising administering the antibody or antigen-binding fragment, or the immunoconjugate of the invention to a human or animal subject. The antibody or antigen-binding fragment can provide a benefit by binding to FAPY-adenine and inhibiting FAPY-adenine-induced nucleotide transversions in the subject. The antibody, antibody fragment, or immunoconjugate can be administered within a pharmaceutical composition further comprising a pharmaceutically acceptable carrier. In some embodiments, the antibody is a human or humanized antibody or antigen-binding fragment thereof.

In some embodiments, the human or animal subject has a disease associated with elevated levels of FAPY-adenine, and the administered antibody, antigen-binding fragment, or immunoconjugate treats the disease. In other embodiments, the human or animal subject does not have a disease associated with elevated levels of FAPY-adenine, and the antibody, antigen-binding fragment, or immunoconjugate is administered prophylactically to prevent or delay onset of the disease.

Diseases caused, or exacerbated, by oxidative stress may be treated, prevented, or their onset delayed, by administration of an antibody, antigen-binding fragment, or immunoconjugate of the invention. Oxidative stress occurs when free radicals and other reactive species overtake the availability of antioxidants. Reactive oxygen species (ROS), reactive nitrogen species, and their counterpart antioxidant agents are essential for physiological signaling and host defense, as well as for the evolution and persistence of inflammation. When their normal steady state is disturbed, imbalances between oxidants and antioxidants may provoke pathological reactions causing a range of diseases that may be treated with the antibody, antigen-binding fragment, or immunoconjugate of the invention. For example, diseases that may be treated include neurodegenerative diseases such as Alzheimer's disease, Parkinson's disease, multiple sclerosis, amyolotrophic lateral sclerosis. Other examples of diseases associated with oxidative stress and free radicals that may be treated include chronic obstructive pulmonary disease (COPD) such as emphysema, and age-related diseases such as diabetes, cardiovascular disease, and autoimmune disease. In some cases, the disease involves or results in an ischemic condition. The disease may be caused by exposure to an environmental contaminant.

In some embodiments, the disease is one in which FAPY-adenine is chronically produced in a localized tissue and the antibody, antigen-binding fragment, or immunoconjugate is administered systemically or locally at the anatomical site of FAPY-adenine production.

FAPY-adenine within dying cells, which are more permeable, and cell debris will generally be more accessible to antibodies, antigen-binding, and immunoconjugates. Protein transduction domains (PTDs) may be fused to the antibody or antibody fragment (serving as a moiety of the immunoconjugate). PTDs are short peptide sequences that enable proteins such antibodies or antibody fragments to translocate across the cell membrane and be internalized within the cell through atypical secretory or internalization pathways.

Antibodies, antibody fragments, and immunoconjugates of the invention can be administered in combination with biologically active agents such as other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine. In some embodiments, the biologically active agent is an anti-cancer agent.

Antibodies, antibody fragments, and immunoconjugates of the invention can be formulated and administered using techniques conventional for biologic agents. Formulations can include excipients, such as taught in Gennaro, ed., Remington: The Science and Practice of Pharmacy, 20th Ed. (Lippincott Williams & Wilkins 2003), the contents of which is incorporated herein by reference. Exemplary excipients include, without limitation, buffering agents (e.g., phosphates, acetate, tris(hydroxymethyl)aminomethane (Tris)), solubilizers and emulsifiers (e.g., polysorbate), preservatives (e.g., thimerosal, benzyl alcohol), salts (e.g., NaCl, KCl) chelators (e.g., EDTA), carbohydrates (e.g., sucrose, dextrose, maltose, trehalose), carriers (e.g., albumin), amino acids and their respective hydrochloride salts, citrates, sorbitol, dextran, and the like.

The antibodies, antibody fragments, and immunoconjugates can be provided as lyophilized powders with or without excipients, which can then be dissolved in a medium such as sterile water for injection, sodium chloride solution for injection, or dextrose solution for injection, with or without additional excipients.

Alternatively, the antibody, antibody fragment, and immunoconjugate can be provided as a concentrated solution, optionally including excipients, which is then diluted to the desired concentration prior to administration. Alternative forms include dispersions, microemulsion, and liposomes.

Preferably, a pharmaceutical composition is suitable for intravenous ("IV"), intramuscular, subcutaneous, parenteral, spinal or epidermal administration (e.g., by injection or infusion). The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Preferred modes of administration include IV infusion, IV bolus, subcutaneous, and intramuscular.

A "therapeutically effective amount" preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be a non-human mammal, such as a non-human mammal.

Dosage regimens are adjusted to provide a therapeutic response. For example, a single dose may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier. Devices such as prefilled syringes, two-chamber syringes, and autoinjectors can be used.

The dosage will vary according to the disease being treated, patient traits such as age, gender, and genotype, and the stage of the treatment regimen. Typically, the dose can be from about 0.5 mg/kg to about 300 mg/kg.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents include but are not limited to those listed in Table 2.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Several examples of chemotherapeutic agents that may be used in conjunction with the antibodies, antibody fragments, and immunoconjugates of the invention are listed in Table 2.

TABLE 2

Examples of Anti-Cancer Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |

TABLE 2-continued

Examples of Anti-Cancer Agents

| | |
|---|---|
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |

TABLE 2-continued

Examples of Anti-Cancer Agents

| | |
|---|---|
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

In the case of cancers, positive clinical outcomes that may result from the methods of the invention that involve treatment include, but are not limited to, alleviation of one or more symptoms of the cancer, diminishment of extent of disease, stabilized (i.e., not worsening) state of disease, delay or slowing of disease progression, amelioration or palliation of the disease state, remission (whether partial or total), whether detectable or undetectable, tumor regression, inhibition of tumor growth, inhibition of tumor metastasis, reduction in cancer cell number, inhibition of cancer cell infiltration into peripheral organs, improved time to disease progression (TTP), improved response rate (RR), prolonged overall survival (OS), prolonged time-to-next-treatment (TNTT), or prolonged time from first progression to next treatment, or a combination of two or more of the foregoing.

Further Definitions

As used herein, the terms "FAPY-adenine", "FAPY-Ade", and "FAPY-A" refer to both bound, e.g., incorporated into DNA or RNA, and free forms of the nucleotide base.

As used herein, the terms "8-OH-adenine", "8-OH-Ade", and "8-OH-A" refer to both bound, e.g., incorporated into DNA or RNA, and free forms of the nucleotide base.

As used in this specification, the singular forms "a", "an", and "the" include plural reference unless the context clearly dictates otherwise. Thus, for example, a reference to "a compound" includes more than one such compound. A reference to "a cell" includes more than one such cell, and so forth.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof), such as a disease associated with elevated levels of FAPY-adenine, or caused, or exacerbated, by oxidative stress. Examples of such diseases include cancer, Alzheimer's disease, Parkinson's disease, multiple sclerosis, amyolotrophic lateral sclerosis, or other neurodegenerative disease; emphysema or other chronic obstructive pulmonary disease (COPD); or diabetes, cardiovascular disease, autoimmune disease, or other age-related disease. In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to prophylaxis (preventing or delaying the onset or development or progression of the disease or disorder).

As used herein, the term "administration" is intended to include, but is not limited to, the following delivery methods: topical, oral, parenteral, subcutaneous, transdermal, transbuccal, intravascular (e.g., intravenous or intra-arterial), intramuscular, subcutaneous, intranasal, and intra-ocular administration. Administration can be local at a particular anatomical site, or systemic.

As used herein, the term "contacting" in the context of contacting a cell with at least one antibody, antigen-binding fragment thereof, or immunoconjugate of the invention in vitro or in vivo means bringing at least one antibody, antigen-binding fragment, or immunoconjugate into contact with the cell, or vice-versa, or any other manner of causing the antibody, antigen-binding fragment, or immunoconjugate and the cell to come into contact. Likewise, as used herein, the term "contacting" in the context of contacting a specimen with at least one antibody, antigen-binding fragment thereof, or immunoconjugate of the invention means bringing at least one antibody, antigen-binding fragment, or immunoconjugate into contact with the specimen, or vice-versa, or any other manner of causing the antibody, antigen-binding fragment, or immunoconjugate and the specimen to come into contact.

As used herein, the terms "patient", "subject", and "individual" are used interchangeably and are intended to include human and non-human animal species. For example, the subject may be a human or non-human mammal. In some embodiments, the subject is a non-human animal model or veterinary patient. For example, the non-human animal patient may be a mammal, reptile, fish, or amphibian. In some embodiments, the non-human animal is a dog, cat, mouse, rat, guinea pig. In some embodiments, the non-human animal is a primate. In some embodiments, the non-human animal is a sentinel species, which are useful as models for epidemiological studies of diseases and environmental exposures. New chemicals are being added each year to the burden of toxic substances in the environment, leading to increased pollution of ecosystems. Sentinel species are the first to be affected by adverse changes in their environment. Detection of DNA damage in sentinel species using the antibodies, fragments, immunoconjugates, and methods of the invention can thus be used to provide information about the genotoxic potential of their habitat at an early stage. In some embodiments, the non-human animal subject is a sentinel species found in sediments of a contaminated site. Sentinel animals can be collected for environmental risk assessment, or during an environmental remediation operation, and tested for FAPY-adenine levels. Thus, the methods of the invention can provide a marker more relevant to the physiological impact of contamination than other markers, such as eggshell thinning, for example.

The terms "sample" and "specimen" are used interchangeably herein to refer to any medium that contains, or has the potential to contain, a target substance for detection and/or measurement, such as FAPY-Ade. The sample may be in any physical state, e.g., solid, liquid, vapor. In some cases, the sample is a biological sample (of biological origin). In some embodiments, the sample is a biological fluid or tissue. In some embodiments, the biological sample is obtained from a subject. The biological sample can be provided as a known or unknown quantity of urine, semen, seminal fluid, synovial fluid, saliva, exhaled breath condensate, tissue, blood, or a blood derived product such as serum or plasma. Samples for study of oxidative DNA damage generally come from two main sources: urinary excretions of oxidized nucleosides and bases from DNA isolated target tissue or cells, such as lymphocytes. Examples of tissue samples include but are not limited to breast, liver, prostate, testes, brain, and skin.

As used herein, the term "antibody" refers to whole antibodies and any antigen binding fragment (i.e., "antigen-binding portion") or single chains thereof. A whole antibody is a glycoprotein comprising at least two heavy (H) chains and two light (L) chains inter-connected by disulfide bonds. Each heavy chain comprises a heavy chain variable region (VH) and a heavy chain constant region comprising three domains, CH1, CH2 and CH3. Each light chain comprises a light chain variable region (VL or Vk) and a light chain constant region comprising one single domain, CL. The VH and VL regions can be further subdivided into regions of hypervariability, termed complementarity determining regions (CDRs), interspersed with more conserved framework regions (FRs). Each VH and VL comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a KD of $5 \times 10^{-8}$ M or less, more preferably $1 \times 10^{-8}$ M or less, more preferably $6 \times 10^{-9}$M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing. The antibody may be any isotype, such as IgM or IgG.

As used herein, the terms "antibody fragment", "antigen-binding fragment", and "antigen-binding portion" of an antibody (or simply "antibody portion") refer to one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment, which is essentially an Fab with part of the hinge region (see, for example, Abbas et al., Cellular and Molecular Immunology, 6th Ed., Saunders Elsevier 2007); (iv) an Fd fragment consisting of the VH and CH1 domains; (v) an Fv fragment consisting of the VL and VH domains of a single arm of an antibody, (vi) a dAb fragment (Ward et al., (1989) *Nature* 341:544-546), which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" or "antigen-binding fragment" of an antibody.

As used herein, the term "isolated antibody" means an antibody or antibody fragment that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

As used herein, the term "monoclonal antibody" or "monoclonal antibody composition" means a preparation of antibody molecules of single molecular composition, which displays a single binding specificity and affinity for a particular epitope.

As used herein, the term "human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

As used herein, the term "human monoclonal antibody" refers to an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

As used herein, the term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

Exemplified Embodiments

Embodiment 1. An antibody, or antigen-binding fragment thereof, having specific binding affinity for 4,6-diamino-5-(formylamino)pyrimidine (FAPY-adenine).

Embodiment 2. The antibody or antigen-binding fragment of embodiment 1, wherein the antibody is a monoclonal antibody.

Embodiment 3. The antibody or antigen-binding fragment of embodiment 1, wherein the antibody is a polyclonal antibody.

Embodiment 4. The antibody or antigen-binding fragment of embodiment 1, wherein the antibody or antigen-binding fragment is produced by the hybridoma having American Type Culture Collection (ATCC) Deposit Designation PTA-121431, deposited with the ATCC on Jul. 24, 2014.

Embodiment 5. The antibody or antigen-binding fragment of any preceding embodiment, wherein the antibody or antigen-binding fragment specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 6. The antibody or antigen-binding fragment of embodiment 2, wherein the antibody or antigen-binding fragment specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 7. The antibody or antigen-binding fragment of embodiment 1, wherein the antibody or antigen-binding fragment comprises:

(a) an immunoglobulin heavy chain variable region ($V_H$) comprising CDR1 sequence at least 80% identical to the CDR1 in FIG. 19, a CDR2 sequence at least 80% identical to the CDR2 sequence in FIG. 19, and a CDR3 at least 80% identical to the CDR3 sequence in FIG. 19; and (b) an immunoglobulin light chain variable region ($V_L$) comprising CDR1 sequence at least 80% identical to the CDR1 in FIG. 21, a CDR2 sequence at least 80% identical to the CDR2 sequence in FIG. 21, and a CDR3 at least 80% identical to the CDR3 sequence in FIG. 21.

Embodiment 8. An immunoconjugate comprising the antibody or antigen-binding fragment of any one of embodiments 1 to 7, coupled to a moiety.

Embodiment 9. The immunoconjugate of embodiment 8, wherein the moiety is a biologically active agent.

Embodiment 10. The immunoconjugate of embodiment 8, wherein the moiety is an immune-stimulating carrier molecule; nanoparticle; detectable label; drug; toxin; chelating agent; biotinylated moiety; tumor targeting agent; protein transduction domain or membrane permeating peptide; or part of a solid support.

Embodiment 11. A hybridoma secreting a monoclonal antibody having specific binding affinity for 4,6-diamino-5-(formylamino)pyrimidine (FAPY-adenine).

Embodiment 12. The hybridoma of embodiment 11, having American Type Culture Collection (ATCC) Deposit Designation PTA-121431, deposited with the ATCC on Jul. 24, 2014.

Embodiment 13. The hybridoma of embodiment 11, wherein the hybridoma produces a monoclonal antibody that specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 14. The hybridoma of embodiment 11, wherein the hybridoma produces a monoclonal antibody that specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 15. A method for determining the presence or amount of FAPY-adenine in a biological specimen, comprising the steps of contacting the specimen with the antibody or antigen-binding fragment of any one of embodiments 1 to 7, or the immunoconjugate of any one of embodiments 8 to 10, to form a complex of (i) antibody, antigen-binding fragment, or immunoconjugate, and (ii) FAPY-adenine; and determining the presence or amount of the complex formed as an indication of the presence or amount of FAPY-adenine in the specimen.

Embodiment 16. The method of embodiment 15, wherein the antibody or antigen-binding fragment is obtained from the hybridoma having American Type Culture Collection (ATCC) Deposit Designation PTA-121431, deposited with the ATCC on Jul. 24, 2014.

Embodiment 17. The method of embodiment 15 or 16, wherein the biological specimen is selected from the group consisting of: cells, tissue, blood, saliva, serum, plasma, synovial fluid, exhaled breath condensate, semen, seminal fluid, and urine.

Embodiment 18. The method of any one of embodiments 15 to 17, wherein the antibody or antigen-binding fragment specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 19. A method for diagnosing or monitoring the status of a disease associated with elevated levels of FAPY-adenine in a human or animal subject, comprising the steps of:

a. contacting a biological specimen of nucleic acids from the human or animal subject with the antibody or antigen-binding fragment of any one of embodiments 1 to 7 or the immunoconjugate of any one of embodiments 8 to 10 to form a complex of: (i) antibody, antigen-binding fragment, or immunoconjugate, and (ii) FAPY-adenine; and b. determining the amount of complex formed as a measure of the presence or amount of FAPY-adenine in the specimen, wherein the amount of complex determined is indicative of the status of a disease associated with elevated levels of FAPY-adenine or is correlated with the status of a disease associated with elevated levels of FAPY-adenine.

Embodiment 20. The method of embodiment 19, wherein the disease is cancer; Alzheimer's disease, Parkinson's disease, multiple sclerosis, amyolotrophic lateral sclerosis, or other neurodegenerative disease; emphysema or other chronic obstructive pulmonary disease (COPD); or diabetes, cardiovascular disease, autoimmune disease, or other age-related disease.

Embodiment 21. The method of embodiment 19 or 20, wherein the antibody or antigen-binding fragment is obtained from the hybridoma having American Type Culture Collection (ATCC) Deposit Designation PTA-121431, deposited with the ATCC on Jul. 24, 2014.

Embodiment 22. The method of any one of embodiments 19 to 21, wherein the biological specimen obtained from the human or animal subject is selected from the group consisting of cells, tissue, blood, saliva, serum, plasma, synovial fluid, exhaled breath condensate, semen, seminal fluid, and urine.

Embodiment 23. The method of any one of embodiments 19 to 22, wherein the determination of antibody, antigen-binding fragment, or immunoconjugate bound to FAPY-adenine is determined by a method selected from the group consisting of enzyme-linked immunosorbent assay (ELISA), immunochemistry, immunohistochemistry (IHC), immunoprecipitation, immunoelectrophoresis, dipstick (antibody, antigen-binding fragment, or immunoconjugate coupled to a solid support), radioimmunoassay (RIA), photochemical assay, and fluorescence assay.

Embodiment 24. The method of any one of embodiments 19 to 23, wherein the antibody, antigen-binding fragment, or immunoconjugate specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 25. A method for determining exposure of a human or animal subject to a toxicant associated with elevated levels of FAPY-adenine in a biological specimen obtained from the human or animal subject, comprising the steps of:

(a) contacting the biological specimen obtained from the human or animal subject with a first amount of the antibody or antigen-binding fragment of any one of embodiments 1 to 7, or an immunoconjugate of any one of embodiments 8 to 10, to form a complex of: (i) antibody, antigen-binding fragment, or immunoconjugate, and (ii) FAPY-adenine;

(b) determining the amount of complex formed in step (a); and (c) comparing the amount of complex determined in step c with a range of FAPY-adenine concentrations found in human or animal specimens that have not been exposed to a toxicant associated with elevated levels of FAPY-adenine.

Embodiment 26. The method of embodiment 25, wherein the amount of complex formed in step a is determined by using a FAPY-adenine standard curve, and wherein the standard curve is obtained by the method of contacting a second amount of the antibody, antigen-binding fragment, or immunoconjugate to a known amount of FAPY-adenine.

Embodiment 27. The method of embodiment 25 or 26, wherein the biological specimen obtained from the human or animal subject is selected from the group consisting of cells, tissue, blood, saliva, serum, plasma, synovial fluid, exhaled breath condensate, semen, seminal fluid, and urine.

Embodiment 28. The method of any one of embodiments 25 to 27, wherein the determination of antibody, antigen-binding fragment, or immunoconjugate bound to FAPY-adenine is determined by a method selected from the group consisting of enzyme-linked immunosorbent assay (ELISA), immunochemistry, immunohistochemistry (IHC), immunoprecipitation, immunoelectrophoresis, dipstick (antibody, antigen-binding fragment, or immunoconjugate coupled to a solid support), radioimmunoassay (RIA), photochemical assay, and fluorescence assay.

Embodiment 29. The method of any one of embodiments 25 to 28 wherein the antibody, antigen-binding fragment, or immunoconjugate specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 30. A method for determining the amount of FAPY-adenine in a biological specimen, comprising:
  a. contacting the antibody or antigen-binding fragment of any one of embodiments 1 to 7 or the immunoconjugate of any one of embodiments 8 to 10 with the specimen to form a complex between: (i) the antibody or antigen-binding fragment, or immunoconjugate, and (ii) FAPY-adenine in the specimen;
  b. quantitating the amount of complex formed; and
  c. comparing the amount of complex formed to the amount of the antibody, antigen-binding fragment, immunoconjugate that complexes with a known amount of FAPY-adenine.

Embodiment 31. The method of embodiment 30, wherein the biological specimen obtained from a human or animal is selected from the group consisting of cells, tissue, blood, saliva, serum, plasma, synovial fluid, exhaled breath condensate, semen, seminal fluid, and urine.

Embodiment 32. The method of embodiment 30 or 31, wherein the quantitation of antibody, antigen-binding fragment, or immunoconjugate bound to FAPY-adenine is determined by a method selected from the group consisting of enzyme-linked immunosorbent assay (ELISA), immunochemistry, immunohistochemistry (IHC), immunoprecipitation, immunoelectrophoresis, dipstick (antibody, antigen-binding fragment, or immunoconjugate, coupled to a solid support), radioimmunoassay (RIA), photochemical assay, and fluorescence assay.

Embodiment 33. The method of any one of embodiments 30 to 32, wherein the antibody, antigen-binding fragment, or immunoconjugate, specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 34. A method for determining the presence or amount of FAPY-adenine in a biological specimen comprising the steps of:
  a. contacting the specimen with the antibody or antigen-binding fragment of any one of embodiments 1 to 7 or the immunoconjugate of any one of embodiments 8 to 10 to form a first complex comprising: (i) the antibody, antigen-binding fragment, or immunoconjugate, and (ii) FAPY-adenine;
  b. contacting the specimen containing the first complex with a second antibody or antigen-binding fragment capable of binding to the first complex; and
  c. determining the amount of second complex formed as a measure of the presence or amount of FAPY-adenine in the specimen.

Embodiment 35. The method of embodiment 34, wherein the biological specimen from a human or animal is selected from the group consisting of cells, tissue, blood, saliva, serum, plasma, synovial fluid, exhaled breath condensate, semen, seminal fluid, and urine.

Embodiment 36. A method for determining the presence or amount of an epitope which comprises FAPY-adenine in a biological specimen comprising the steps of:
  a. contacting the specimen with the antibody or antigen-binding fragment of any one of embodiments 1 to 7, or the immunoconjugate of any one of embodiments 8 to 10, to form a complex of: (i) antibody, antigen-binding fragment, or immunoconjugate, and (ii) epitope, and
  b. determining the presence or amount of complex formed as a measure of the presence on amount of epitope in the specimen.

Embodiment 37. The method of embodiment 36, wherein the biological specimen from a human or animal is selected from the group consisting of cells, tissue, blood, saliva, serum, plasma, synovial fluid, exhaled breath condensate, semen, seminal fluid, and urine.

Embodiment 38. The method of embodiment 36 or 37, wherein the antibody, antigen-binding fragment, or immunoconjugate specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 39. The method of embodiment 36, wherein the antibody, antigen-binding fragment, or immunoconjugate specifically binds to an epitope on the base portion of FAPY-adenine and does not significantly cross-react with other nucleotide bases nor with carbohydrate or protein portions of carbohydrate or protein conjugates of FAPY-adenine or other nucleoside bases.

Embodiment 40. A method for binding FAPY-adenine in a human or animal subject, comprising administering the antibody or antigen-binding fragment of any one of embodiments 1 to 7, or the immunoconjugate of any one of embodiments 8 to 10, to the human or animal subject.

Embodiment 41. The method of embodiment 40, wherein the antibody or antigen-binding fragments inhibits FAPY-adenine-induced nucleotide transversion in the subject.

Embodiment 42. The method of embodiment 40 or 41, wherein the human or animal subject has a disease associated with elevated levels of FAPY-adenine, and the administered antibody, antigen-binding fragment, or immunoconjugate treats the disease.

Embodiment 43. The method of embodiment 42, wherein the disease is cancer.

Embodiment 44. The method of embodiment 42 or 43, wherein the disease is caused, or exacerbated, by oxidative stress.

Embodiment 45. The method of embodiment 42 or 44, wherein the disease is Alzheimer's disease, Parkinson's disease, multiple sclerosis, amyolotrophic lateral sclerosis, or other neurodegenerative disease; emphysema or other chronic obstructive pulmonary disease (COPD); diabetes, cardiovascular disease, autoimmune disease, or other age-related disease.

Embodiment 46. The method of any one of embodiments 42 to 45, wherein the disease is caused by exposure to an environmental contaminant.

Embodiment 47. The method of embodiment 40 or 41, wherein the human or animal subject does not have a disease associated with elevated levels of FAPY-adenine, and wherein the antibody, antigen-binding fragment, or immunoconjugate is administered prophylactically to prevent or delay onset of the disease.

Embodiment 48. The method of any one of embodiments 40 to 47, wherein the antibody, antigen-binding fragment, or immunoconjugate has an imaging agent coupled thereto, and wherein said method further comprises imaging the human or animal subject after administration of the antibody, antigen-binding fragment, or immunoconjugate.

Embodiment 49. A method of assessing cancer risk in a human or animal subject, comprising:
  comparing the measured amount of an 8-hydroxy-purine in a biological specimen obtained from the human or animal subject to the measured amount of a formamidopyrimidine-purine (FAPY-purine) in a biological specimen obtained from the human or animal subject, wherein a higher measured amount of 8-hydroxy-purine relative to the measured amount of FAPY-purine is indicative of an increased risk of developing cancer, and wherein a higher measured amount of FAPY-purine relative to the measured amount of 8-hydroxy-purine is indicative of a lower risk of developing cancer.

Embodiment 50. The method of embodiment 49, wherein the 8-hydroxy-purine is 8-hydroxy-adenine, 8-hydroxy-guanine, or both.

Embodiment 51. The method of embodiment 49 or 50, wherein the FAPY purine is FAPY-adenine.

Embodiment 52. The method of any one of embodiments 49 to 51, wherein the amount of 8-hydroxy-purine and/or FAPY-purine is measured by a method selected from the group consisting of enzyme-linked immunosorbent assay (ELISA), immunochemistry, immunohistochemistry (IHC), immunoprecipitation, immunoelectrophoresis, dipstick (antibody, antigen-binding fragment, or immunoconjugate, coupled to a solid support), radioimmunoassay (MA), photochemical assay, and fluorescence assay.

Embodiment 53. The method of any one of embodiments 49 to 52, wherein the comparing step comprises electronically comparing in a computer values reflective of the measured amount of 8-hydroxy-purine and FAPY-purine.

Embodiment 54. The method of any one of embodiments 49 to 53, wherein the amount of FAPY purine is measured by:

a. contacting the biological specimen with the antibody or antigen-binding fragment of any one of embodiments 1 to 7, or the immunoconjugate of any one of embodiments 8 to 10, to form a complex of: (i) antibody, antigen-binding fragment, or immunoconjugate, and (ii) epitope, and b. determining the amount of complex formed as a measure of the amount of epitope in the biological specimen.

Embodiment 55. The method any one of embodiments 49 to 54, wherein the biological specimen is selected from the group consisting of cells, tissue, blood, saliva, serum, plasma, synovial fluid, exhaled breath condensate, semen, seminal fluid, and urine.

Embodiment 56. The method of any one of embodiments 49 to 54, wherein the biological specimen is a tissue specimen.

Materials and Methods

Figure 1A:
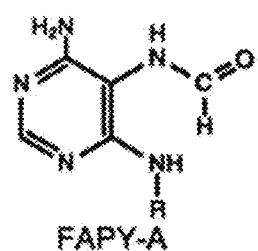
FIGS. 1A and 1B. Chemical structures of two alternative reaction products resulting from single electron oxidation reactions caused primarily by oxygen free radicals.
Figure 1B:
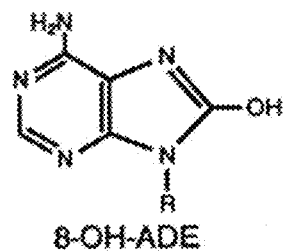
Figure 2:
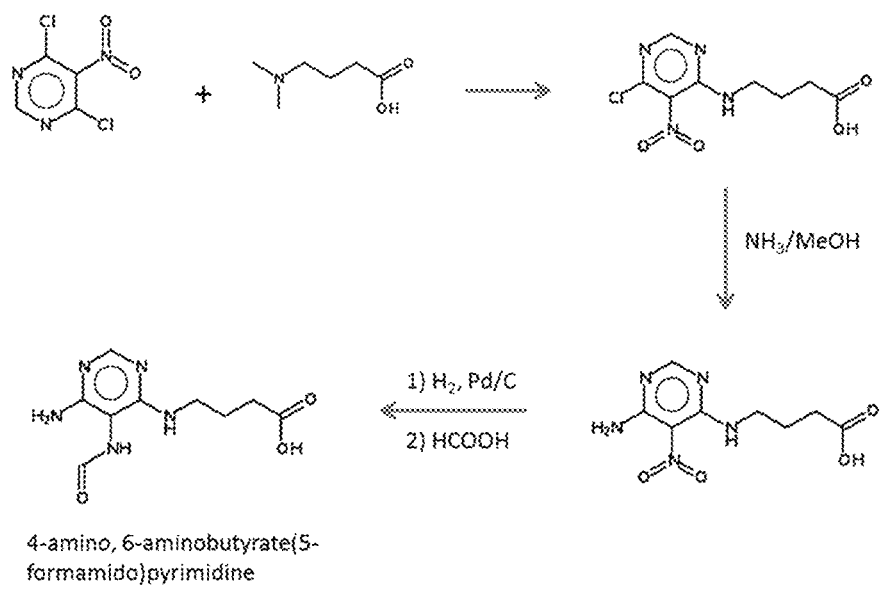
FIG. 2. Synthesis of 4-amino, 6-aminobutyrate(5-formamido)pyrimidine.

Synthesis of immunogen. The FAPY-A hapten structure containing a linker group for coupling to proteins was chemically synthesized as shown in FIG. 2. 4,6-Dichloro, 5-nitro-pyrimidine and 4-amino-butanoic acid were obtained from Sigma/Aldrich and reacted in a roughly equimolar ratio and the mono-substituted product was isolated. A second substitution reaction was performed with ammonia/MeOH to yield a product with a free aryl amine group. After isolation of the product the nitro group was reduced with H2 over Pd/C catalyst and treated with formic acid to introduce a 5-formylamido group resulting in the final product, 4-amino, 6-aminobutyrate(5-formamido)pyrimidine.

Coupling of the synthesized FAPY-A hapten to keyhole limpet hemocyanin (KLH) and bovine serum albumin (BSA) for immunization and screening, respectively, was done using standard water soluble carbodiimide coupling procedures.

Briefly, EDC (1-ethyl-3-(3-dimethylaminopropyl)carbodiimide hydrochloride), 10 mg, was mixed with Carrier protein (2 mg bovine serum albumin (BSA) or keyhole limpet hemocyanin (KLH), conjugation buffer composed of 0.1M MES (2-[N-morpholino]ethane sulfonic acid), pH 4.5-5, and 1 mg of FAPY-A hapten in a total volume of 0.7 ml and the reaction was allowed to proceed for 2 hours at room temperature followed by extensive dialysis with PBS. The FAPY-A protein conjugates were then utilized for immunization (KLH conjugate) or as a screening antigen (BSA conjugate) and could be stored frozen.

Preparation of nucleosides coupled to BSA for screening. Coupling of 8-hydroxy-adenosine and 8-hydroxy-guanosine to BSA was conducted through the ribose moiety of the nucleoside after mild oxidization by $NaIO_4$ at pH 4.5 using a sodium phosphate buffer. The progress of the oxidation reaction was followed by the change in mobility of the UV-absorbing spots after thin layer chromatography on silica gel plates using a solvent system composed of $CHCl_3$: $CH_3OH$ (2:1). The oxidized product migrates as a faster moving spot on the chromatogram. This introduces vicinal aldehyde groups capable of forming Schiff bases with primary amines.

Commercially obtained periodate oxidized nucleosides used were adenosine, cytosine, uracil, and guanosine (Sigma/Aldrich). 8-OH-guanosine was prepared according to the method described by Cho et al. (22) and 8-OH-adenosine was prepared according to the method of Cho and Evans (23).

The BSA conjugates were prepared by Schiff base formation with lysine groups followed by reduction with $NaCNBH_3$ in PBS followed by extensive dialysis versus PBS. All BSA conjugates contained approximately 15 hapten molecules per protein subunit.

Immunization of animals. An immunogen was prepared composed of 0.7 ml FAPY-A-KLH conjugate (1.43 mg/ml), 0.1 ml muramyl dipeptide (20 mg/ml), 0.2 ml deionized distilled water, and 1.0 ml Freund's incomplete adjuvant. The mixture was emulsified thoroughly to yield a thick composition that does not disperse when a drop is placed on a water surface. Balb/c mice, male, one month old, were immunized subcutaneously in two locations each with 50 µl of immunogen. Immunizations were repeated weekly for 3 weeks and then monthly until the animal was used for a fusion. Serum titers were checked by a solid phase binding assay using the FAPY-A-BSA conjugate (see FIG. 3). A final immunization on a selected mouse was done 3 days prior to fusion.

Hybridoma Preparation. Three days following the final boost with the FAPY-A-KLH conjugate, the spleen of a BALB/c mouse was aseptically removed and a single cell suspension was prepared. The red blood cells were lysed by osmotic shock and the remaining lymphocytes were suspended in RPMI-1640 medium. The splenocytes were mixed with P3X63Ag8U.1 (X63) myeloma cells (CRL 1597 from ATCC, Rockville, Md.) at a ratio of 10:1 ($100 \times 10^6$ splenocytes: $10 \times 10^6$ X63 myeloma cells). Fusion of the splenocytes to X63 cells was performed by the method of Galfre and Milstein (24). Hybridoma cells were selected by the inclusion of aminopterin in the cell culture medium (RPMI-1640-20% fetal calf serum).

Once clones of hybridoma cells appeared after HAT selection, supernatant was tested for binding to FAPY-A-BSA in a solid phase binding assay on 96-well Probind plates coated with 50 µl of 50 µg/ml FAPY-A-BSA conjugate. Wells were initially screened for positive reactivity with the FAPY-A-BSA conjugate and for negative reactivity with Adenosine-BSA and 8-hydroxy-Adenosine-BSA conjugates and BSA. All FAPY-A-BSA positive clones were expanded and frozen in liquid nitrogen and some selected for cloning. Wells containing monoclonal hybridomas were moved to 24-well plates and expanded for more detailed analysis of antibody binding specificity. Monoclonal antibodies derived from the resultant hybridoma clones were tested for specificity in a side-by-side comparison of reactivity with FAPY-A-BSA, Adenosine-BSA, 8-OH-Adenosine-BSA, Guanosine-BSA, 8-OH-Guanosine-BSA, Cytosine-BSA, and Uracil-BSA conjugates. Hybridoma cells expressing highly specific anti-FAPY-A monoclonal antibodies were expanded and frozen, and the expressed antibodies used in a variety of additional characterization studies.

Solid Phase Immunoassay. Solid phase immunoassays were used with two different detection methods, a $^{125}$I-Protein A binding assay and a colorimetric assay. Assay plates were prepared by coating 96-well Probind plates with 50 µl of a solution containing 50 µg of protein conjugate per ml of 50 mM sodium phosphate buffer, pH 7.5, 5 mM $MgCl_2$, 15 mM $NaN_3$ and incubated overnight. The plates were blocked with PBS containing 5% BSA for 2 hours, followed by incubation with antibody containing culture supernatant for 18 hours. The plates were then washed extensively with PBS. The plates were then incubated with 1:500 diluted rabbit anti-mouse whole Ig (ICN Immunobiologicals, Costa Mesa, Calif.) for 1 hour followed by extensive washing with PBS. For $^{125}$I-Protein A binding detection the plates were incubated with $^{125}$I-protein A (100,000 cpm/well) for 1 hour. The plates were washed again with PBS and the amount of $^{125}$I in each well was determined in a gamma counter.

For the colorimetric assay the 1:500 diluted rabbit anti-mouse whole Ig secondary antibody treated and PBS washed plates were incubated with 50 µl of a 1:400 dilution of HRP-conjugated Protein-A (Sigma) added to each well. Following a 1 hour incubation at room temperature, the plates were extensively washed with PBS and 100 µl of ABTS (150 mg 2,29-azino-bis[3-ethylbenzthiazoline-6-sulfonic acid in 500 ml of 0.1 M citric acid, pH 4.35]/$H_2O_2$ (10 mL 30% $H_2O_2$ per 10 ml of ABTS solution) chromogen/substrate solution was added to each well). After a 5-min incubation, the reaction was stopped with the addition of 100 µl of stop solution (SDS/dimethylformamide) and the absorbance at 405 nm was read in a microplate reader.

In some assays, varying amounts of the FAPY-A base, 4,6-diamino(5-formamide)pyrimidine (Sigma/Aldrich), was added to the hybridoma culture supernatant and incubated for 1 hour prior to assay on a FAPY-A-BSA coated plate according to the methods described above.

Murine antibody isotype determination. The isotype of the antibody secreted by the cloned hybridoma cell lines was determined using ISOStrips (Boehringer Mannheim) according to the manufacturer's instructions.

Sequencing of antibody genes. Sequencing of anti-FAPY-A clone FA5 was conducted. Specifically, total RNA was extracted from frozen hybridoma cells provided by the client and cDNA was synthesized from the RNA. RT-PCR was then performed to amplify the variable regions (heavy and light chains) and constant regions of the antibody, which were then cloned into a standard cloning vector separately and sequenced. TRIZOL® Plus RNA Purification System was used (Invitrogen, Cat. No.: 15596-026); SUPERSCRIPT™ III First-Strand Synthesis System (Invitrogen, Cat. No.: 18080-051).

Total RNA extraction. Total RNA was isolated from the hybridoma cells following the technical manual of TRIZOL® Plus RNA Purification System. The total RNA was analyzed by agarose gel electrophoresis.

RT-PCR. Total RNA was reverse transcribed into cDNA using isotype-specific anti-sense primers or universal primers following the technical manual of SUPERSCRIPT™ III First-Strand Synthesis System. The antibody fragments of VH, VL, CH and CL were amplified according to the standard operating procedure of RACE of GenScript.

Cloning of antibody genes. Amplified antibody fragments were separately cloned into a standard cloning vector using standard molecular cloning procedures. The isolated total RNA of the sample was run alongside a DNA marker Marker III (TIANGEN, Cat. No.: MD103) on a 1.5% agarose/GELRED™ gel (FIGS. 22A-22B). Screening and sequencing. Colony PCR screening was performed to identify clones with inserts of correct sizes. No less than five single colonies with inserts of correct sizes were sequenced for each antibody fragment. Four microliters of PCR products of each sample were run alongside the DNA marker Marker III on a 1.5% agarose/GELRED™ gel (FIG. 23). The PCR products were purified and stored at −20° C. until further use.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Immunization of Mice with FAPY-A-KLH Conjugate

Figure 3:
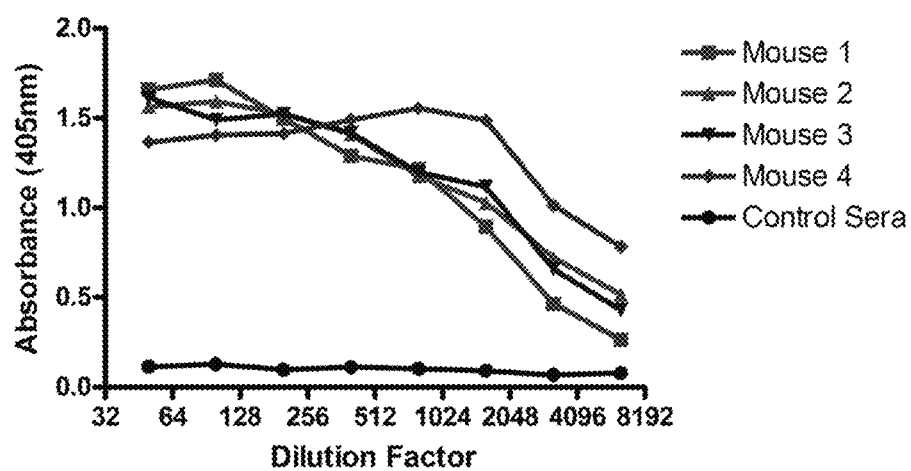
FIG. 3. Anti-FAPY-A serum titers in mice.
Figure 4:
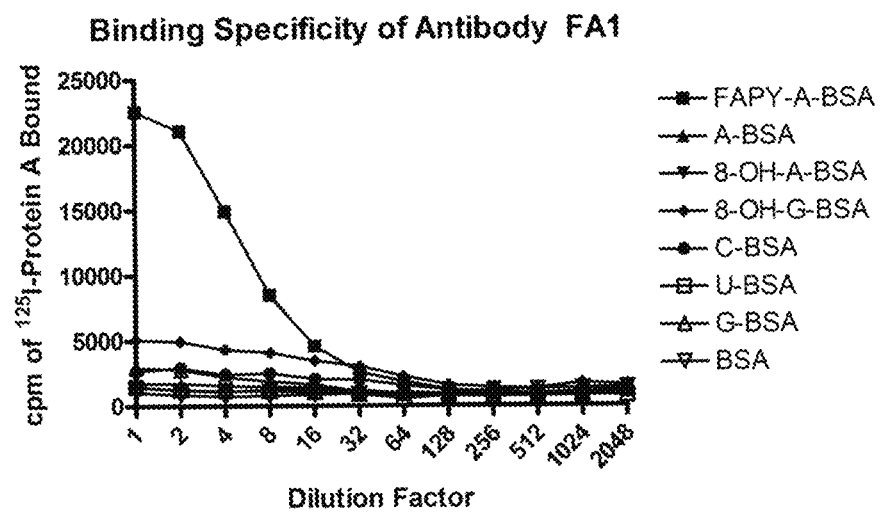
FIG. 4. Binding specificity of antibody FA1.
Figure 5:
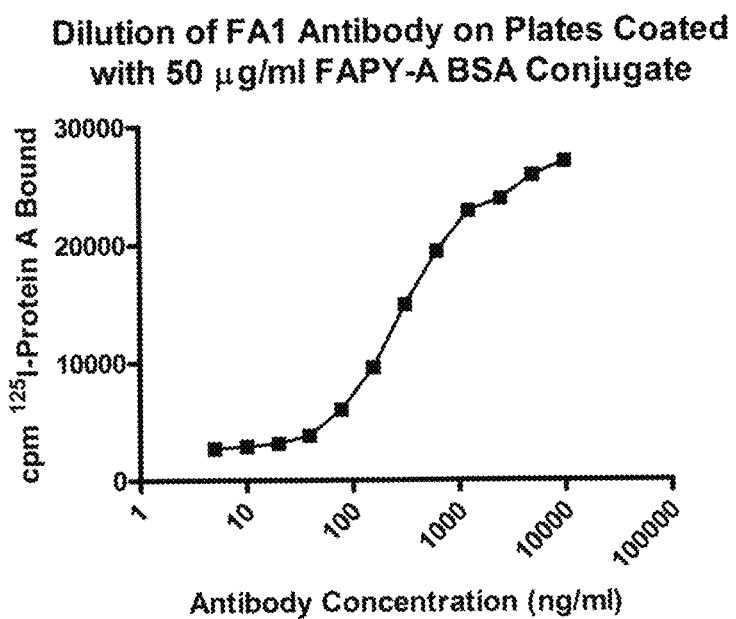
FIG. 5. Dilution of FA1 antibody on plates coated with 50 µg/ml FAPY-A BSA conjugate.
Figure 6:
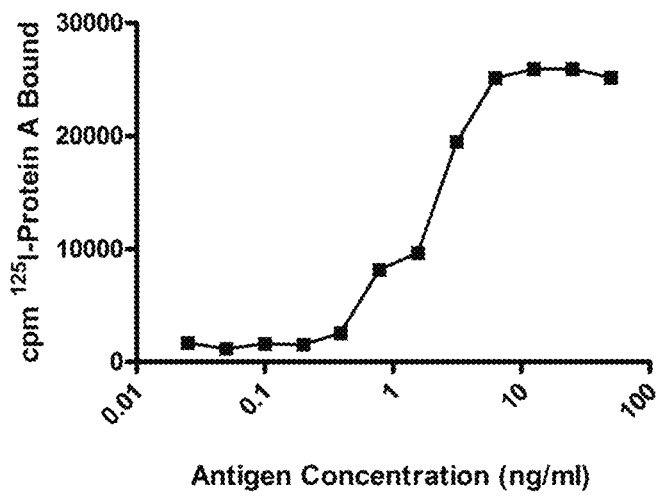
FIG. 6. Dilution FAPY-A-BSA conjugate coated on plates detected with 5 µg/ml FA1 antibody.
Figure 7:
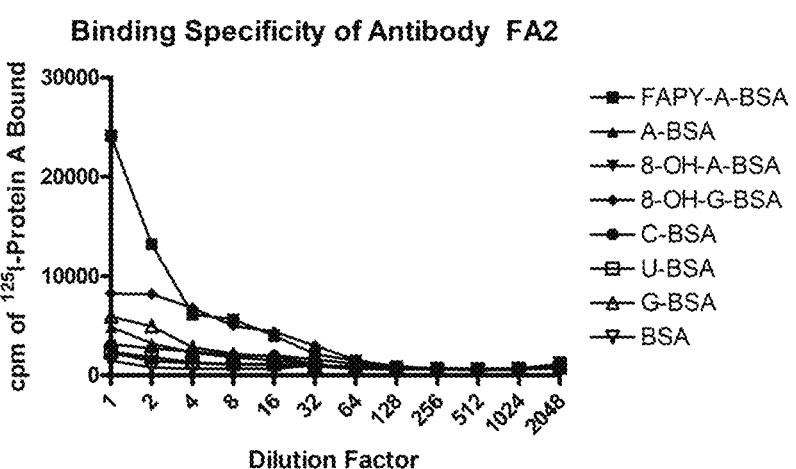
FIG. 7. Binding specificity of antibody FA2.
Figure 8:
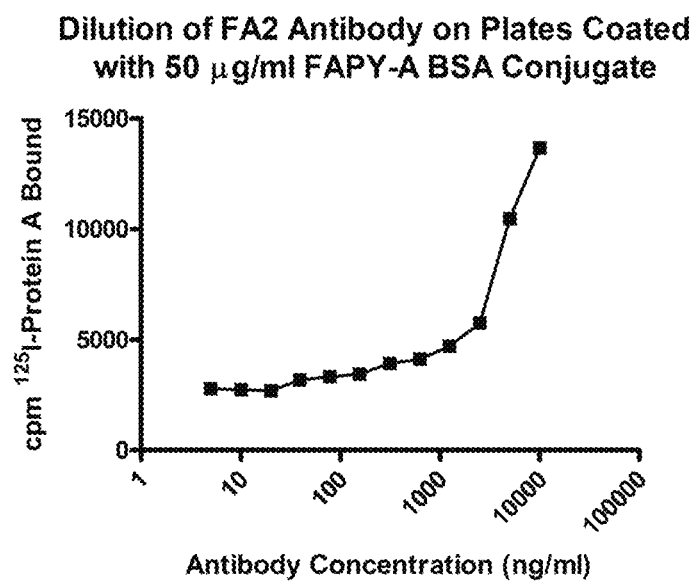
FIG. 8. Dilution of FA2 antibody on plates coated with 50 µg/ml FAPY-A BSA conjugate.
Figure 9:
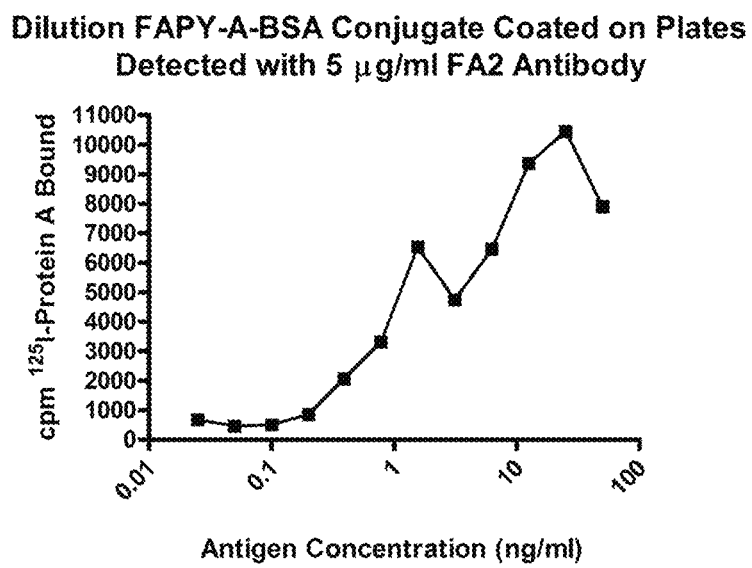
FIG. 9. Dilution FAPY-A-BSA conjugate coated on plates detected with 5 μg/ml FA2 antibody.
Figure 10:
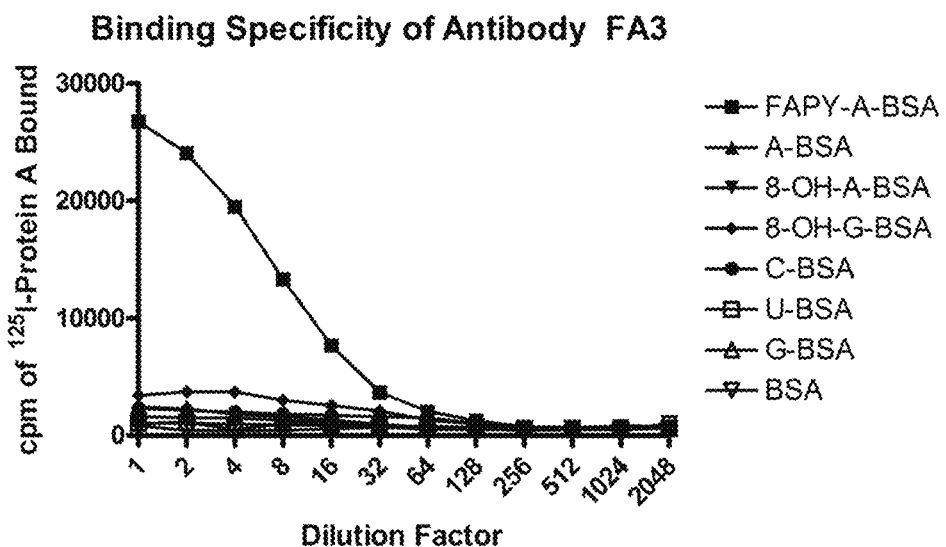
FIG. 10. Binding specificity of antibody FA3.
Figure 11:
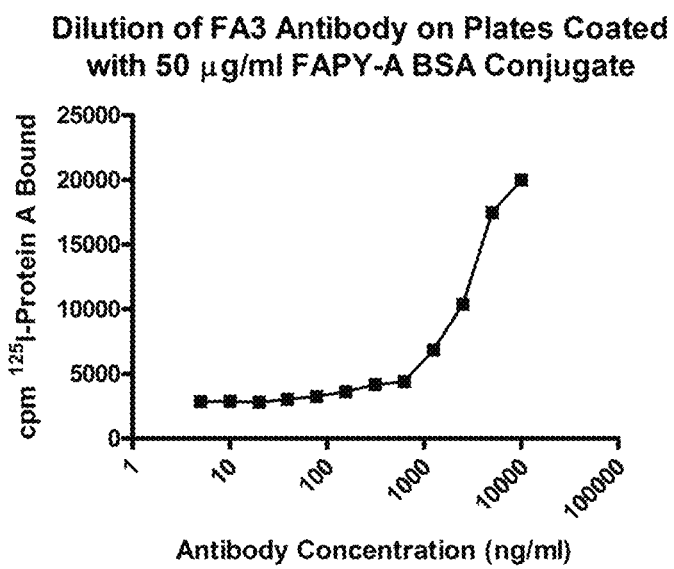
FIG. 11. Dilution of FA3 antibody on plates coated with 50 μg/ml FAPY-A BSA conjugate.
Figure 12:
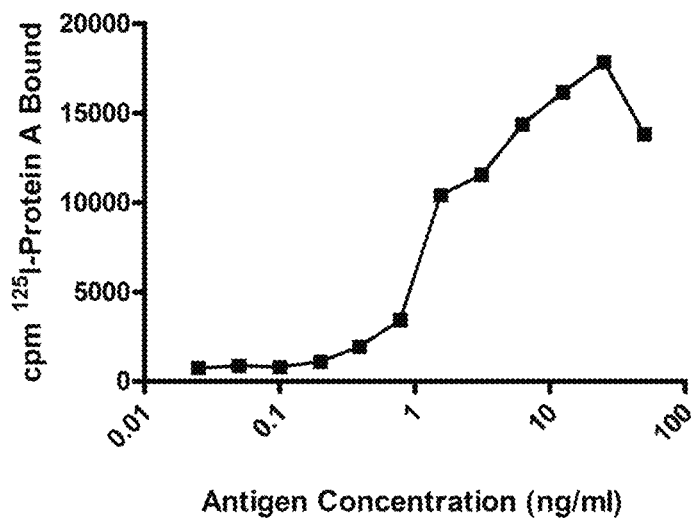
FIG. 12. Dilution FAPY-A-BSA conjugate coated on plates detected with 5 μg/ml FA3 antibody.
Figure 13:
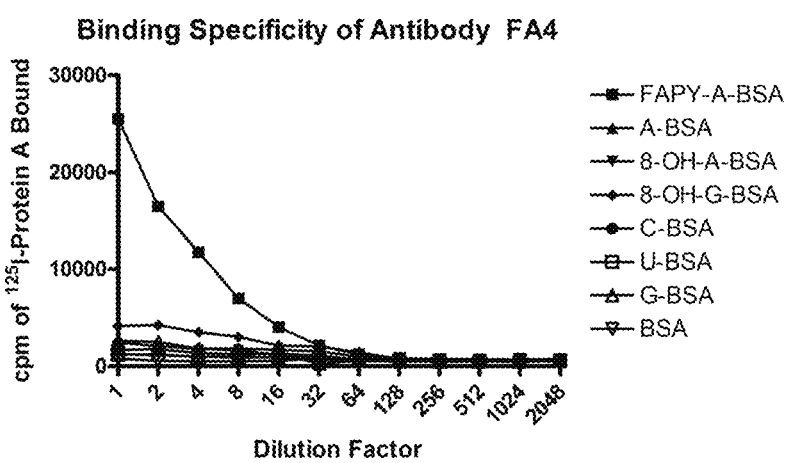
FIG. 13. Binding specificity of antibody FA4.
Figure 14:
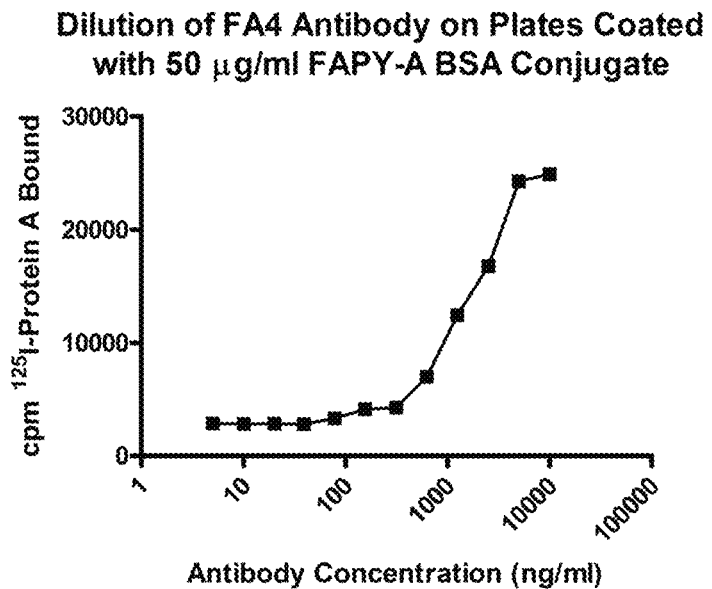
FIG. 14. Dilution of FA4 antibody on plates coated with 50 μg/ml FAPY-A BSA conjugate.
Figure 15:
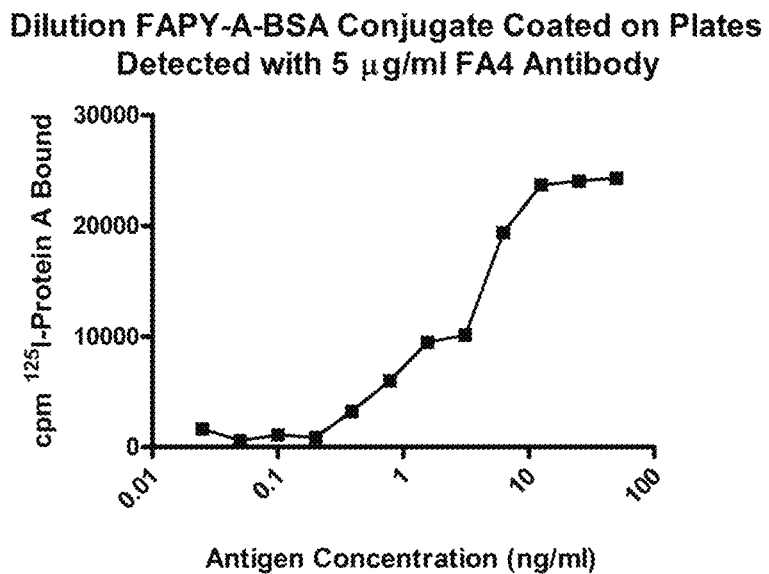
FIG. 15. Dilution FAPY-A-BSA conjugate coated on plates detected with 5 μg/ml FA4 antibody.
Figure 16:
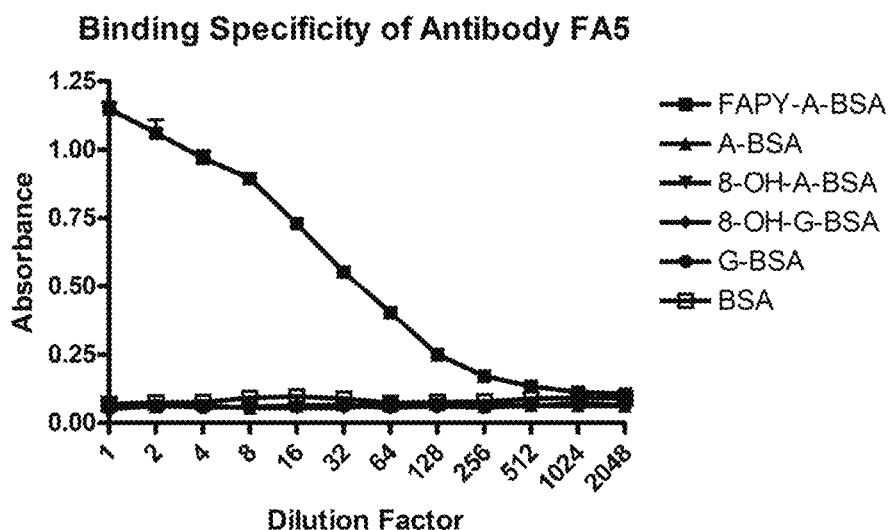
FIG. 16. Binding specificity of antibody FA5.

Serum titers after 1 month of immunization (one week after three weekly immunizations) demonstrated significant antigen titers when assayed using a FAPY-A-BSA conjugate (FIG. 3). Fusions were conducted 3 days after a subsequent final immunization or after additional monthly immunizations followed by the final immunization 3 days before fusion.

Example 2—Preparation and Initial Characterization of Anti-FAPY-A Monoclonal Antibodies A total of 35 FAPY-A positive wells were obtained from multiple fusions with animals that had been immunized over a period of 1-2 months or as much as 6 months. On initial screening with FAPY-A-BSA, 19 of which had no detectable reactivity with Adenosine-BSA, 8-hydroxy-Adenosine-BSA, or BSA and 16 which had strong FAPY-A-BSA reactivity and apparently weak binding to one or more negative control antigens. This weak reactivity in the fusion primary screen could be due to other antibodies present in the supernatant. To determine the basic properties of antibodies from this group of 35 positive hybridomas, a group of 5 FAPY-A specific hybridomas were selected and cloned and the resulting monoclonal antibodies characterized by a variety of means. The rest of the polyclonal wells expressing anti-FAPY-A antibody specificity were expanded into 24-well plates and frozen in liquid nitrogen for future attention as needed.

FIGS. 4, 7, 10, 13, and 16 demonstrate the binding specificity of cloned monoclonal antibodies FA1, FA2, FA3, FA4, and FA5, respectively. Each antibody shows strong binding to the FAPY-A-BSA conjugate. Varying amounts of antibody binding were observed to a variety of irrelevant antigens with the binding of FA3 and especially FA5 showing the least apparent irrelevant cross reactivity.

FIGS. 5, 8, 11, and 14 demonstrate binding of increasing amounts of antibodies FA1, FA2, FA3, and FA4, respectively, to a fixed amount of FAPY-A-BSA. Conversely, FIGS. 6, 9, 12, and 15 demonstrate the effect of decreasing amounts of FAPY-A-BSA on binding of a fixed amount of antibodies FA1, FA2, FA3, and FA4, respectively. These results demonstrate similar apparent antigen binding affinity and avidity for these antibodies.

Figure 17:
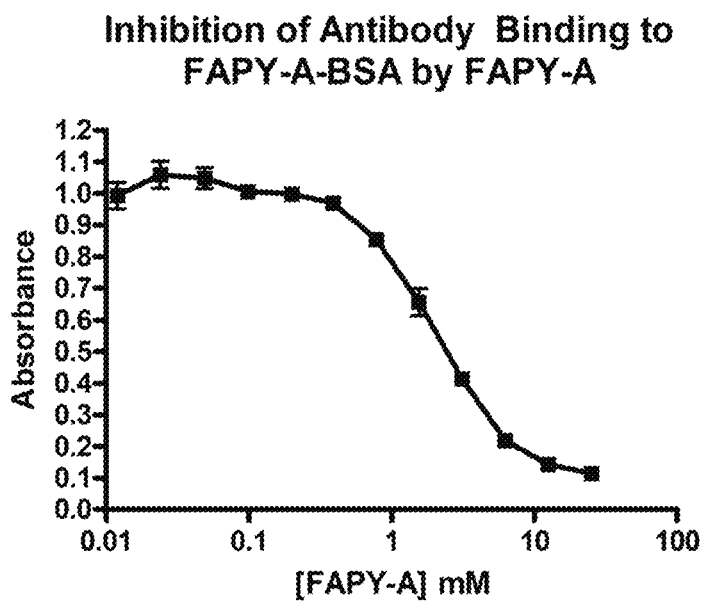
FIG. 17. Inhibition of FA5 binding.

In these studies, antibody FA5 appeared to have the highest antigen specificity and it was chosen for analysis of inhibition of binding to FAPY-A-BSA by 4,6-diamino(5-formamido)pyrimidine (FAPY-A base) in solution as shown in FIG. 17. The results demonstrated effective inhibition of binding with a 50% reduction in binding at about 2.2 mM FAPY-A base. These results confirm FAPY-A binding specificity of FA5.

Example 3—Isotype Determination

ISOStrips were used to determine the isotype of the antibody secreted by hybridomas FA1, FA2, FA3, FA4, and FA5 and the results shown in Table 3. Hybridomas FA1, FA2, FA3, and FA4 were derived from mice immunized over a period of 1-2 months and antibody FA5 from an animal immunized for 6 months.

TABLE 3

Anti-FAPY-A Murine Antibody Isotypes.

| Hybridoma | Isotype Secreted |
|---|---|
| FA1 | IgM |
| FA2 | IgG$_1$ |
| FA3 | IgG$_1$ |
| FA4 | IgM |
| FA5 | IgG$_3$ |

Example 4—Antibody Sequencing

An IgG antibody having the highest antigen specificity and binding was deemed to be optimal for future uses. Accordingly, the FA5 hybridoma was selected for sequencing of the heavy and light chain genes. The DNA and deduced amino acid sequences for these genes are shown in FIGS. 18-21, and below (SEQ ID Nos:1-4).

Hybridoma strain (designated as "Murine Hybridoma (FA5)" (ATCC Accession No. PTA-121431) was deposited with American Type Culture Collection (ATCC), Manassas, Va., USA, on Jul. 24, 2014.

Five single colonies with correct $V_H$, $V_L$, $C_H$, and $C_L$ insert sizes were sent for sequencing. The $V_H$, $V_L$, $C_H$, and $C_L$ genes of five different clones were found nearly identical (FIGS. 24 and 25). The consensus sequence, listed below, is believed to be the sequence of the antibody produced by the hybridoma FAPY-A.

Note: $V_H$ and $V_L$ plasmids encode the full-length variable regions of the antibody and a part of $C_H1$ and $C_L$. $C_H$ plasmid encodes a part of $C_H1$ and full-length $C_H2$ and $C_H3$. $C_L$ plasmid encodes a part of $C_L$. In order to get full-length constant regions or heavy/light chain, the part of constant regions encoded by $V_H$ and $V_L$ plasmids and the part of constant regions encoded by $C_H$ and $C_L$ plasmids need to be amplified by PCR separately, and then employ overlap extension PCR to obtain full-length DNAs. The primer information can be obtained from the aligned sequences in FIGS. 24 and 25.

Heavy chain: DNA sequence (1404 bp):
Leader sequence-FR1-CDR1-FR2-CDR2-FR3-CDR3-FR4-Constant region-Stop codon (SEQ ID NO: 1)
ATGAACTTTGGGCTGAGCTTGATTTTCCTTGTCCTAATTTTAAAAGGTGT

CCAGTGTGAAGTGATGCTGGTGGAGTCTGGGGGAGGCTTAGTGAAGCCTG

GAGGGTCCCTGAAACTCTCCTGTGCAGCCTCTGGATTCCCTTTCAGTAGT

TATGTCATGTCTTGGGTTCGCCAGACTCCGCAGAAGAGGCTGGAGTGGGT

CGCAACCATTAGTAGTGGTGGTGGTAGTACCTCTAATCCAGACACTGTGA

AGGGTCGGTTCACCATCTCCAGAGACAATGCCAAGAACAACCTGTACCTG

CAAATGGACAGTCTCAGGTCTGAGGACACGGCCTTGTATTACTGTGCGAG

CCTTTATTACTACGGTCGTGGGGCTTACTGGGGCCAAGGGACTCTGGTCA

CTGTCTCTGCAGCTACAACAACAGCCCCATCTGTCTATCCCTTGGTCCCT

GGCTGCAGTGACACATCTGGATCCTCGGTGACACTGGGATGCCTTGTCAA

AGGCTACTTCCCTGAGCCGGTAACTGTAAAATGGAACTATGGAGCCCTGT

CCAGCGGTGTGCGCACAGTCTCATCTGTCCTGCAGTCTGGGTTCTATTCC

CTCAGCAGCTTGGTGACTGTACCCTCCAGCACCTGGCCCAGCCAGACTGT

CATCTGCAACGTAGCCCACCCAGCCAGCAAGACTGAGTTGATCAAGAGAA

TCGAGCCTAGAATACCCAAGCCCAGTACCCCCCAGGTTCTTCATGCCCA

CCTGGTAACATCTTGGGTGGACCATCCGTCTTCATCTTCCCCCCAAAGCC

CAAGGATGCACTCATGATCTCCCTAACCCCCAAGGTTACGTGTGTGGTGG

TGGATGTGAGCGAGGATGACCCAGATGTCCATGTCAGCTGGTTTGTGGAC

AACAAAGAAGTACACACAGCCTGGACACAGCCCCGTGAAGCTCAGTACAA

CAGTACCTTCCGAGTGGTCAGTGCCCTCCCCATCCAGCACCAGGACTGGA

TGAGGGGCAAGGAGTTCAAATGCAAGGTCAACAACAAAGCCCTCCCAGCC

CCCATCGAGAGAACCATCTCAAAACCCAAAGGAAGAGCCCAGACACCTCA

AGTATACACCATACCCCCACCTCGTGAACAAATGTCCAAGAAGAAGGTTA

GTCTGACCTGCCTGGTCACCAACTTCTTCTCTGAAGCCATCAGTGTGGAG

TGGGAAAGGAACGGAGAACTGGAGCAGGATTACAAGAACACTCCACCCAT

CCTGGACTCAGATGGGACCTACTTCCTCTACAGCAAGCTCACTGTGGATA

CAGACAGTTGGTTGCAAGGAGAAATTTTTACCTGCTCCGTGGTGCATGAG

GCTCTCCATAACCACCACACACAGAAGAACCTGTCTCGCTCCCCTGGTAA

ATGA

Heavy chain: Amino acids sequence (467 AA):
Leader sequence-FR1-CDR1-FR2-CDR2-FR3-CDR3-FR4-Constant region (SEQ ID NO: 2)
MNFGLSLIFLVLILKGVQCEVMLVESGGGLVKPGGSLKLSCAASGFPFSS

YVMSWVRQTPQKRLEWVATISSGGGSTSNPDTVKGRFTISRDNAKNNLYL

QMDSLRSEDTALYYCASLYYYGRGAYWGQGTLVTVSAATTTAPSVYPLVP

GCSDTSGSSVTLGCLVKGYFPEPVTVKWNYGALSSGVRTVSSVLQSGFYS

LSSLVTVPSSTWPSQTVICNVAHPASKTELIKRIEPRIPKPSTPPGSSCP

-continued

```
PGNILGGPSVFIFPPKPKDALMISLTPKVTCVVVDVSEDDPDVHVSWFVD

NKEVHTAWTQPREAQYNSTFRVVSALPIQHQDWMRGKEFKCKVNNKALPA

PIERTISKPKGRAQTPQVYTIPPPREQMSKKKVSLTCLVTNFFSEAISVE

WERNGELEQDYKNTPPILDSDGTYFLYSKLTVDTDSWLQGEIFTCSVVHE

ALHNHHTQKNLSRSPGK
```

Light chain: DNA sequence (705 bp):
Leader sequence-FR1-CDR1-FR2-CDR2-FR3-CDR3-FR4-
Constant region-Stop codon (SEQ ID NO: 3)
```
ATGGCCTGGATTTCACTTATACTCTCTCTCCTGGCTCTCAGCTCAGGGGC

CATTTCCCAGGCTGTTGTGACTCAGGAATCTGCACTCACCACATCACCTG

GTGAAACAGTCACACTCACTTGTCGCTCAAGTTCTGGGCCTGTTACAACT

AGTAACTATGCCAACTGGGTCCAAGAAAGACCAGATCATTTATTCACTAA

TCTAATAGGTGGTACCAACAACCGAGCTCCAGGTGTTCCTGCCAGATTCT

CAGGTTCCCTGATTGGAGACAAGGCTGCCCTCACCATCACAGGGGCACAG

ACTGAGGATGAGGCAATATATTTCTGTGCTCTATGGTACAGTAACCATTT

GGTGTTCGGTGGAGGAACCAAACTGACTGTCCTAGGCCAGCCCAAGTCTT

CGCCATCAGTCACCCTGTTTCCACCTTCCTCTGAAGAGCTCGAGACTAAC

AAGGCCACACTGGTGTGTACGATCACTGATTTCTACCCAGGTGTGGTGAC

AGTGGACTGGAAGGTAGATGGTACCCCTGTCACTCAGGGTATGGAGACAA

CCCAGCCTTCCAAACAGAGCAACAACAAGTACATGGCTAGCAGCTACCTG

ACCCTGACAGCAAGAGCATGGGAAAGGCATAGCAGTTACAGCTGCCAGGT

CACTCATGAAGGTCACACTGTGGAGAAGAGTTTGTCCCGTGCTGACTGTT

CCTAG
```

Light chain: Amino acids sequence (234 AA):
Leader sequence-FR1-CDR1-FR2-CDR2-FR3-CDR3-FR4-
Constant region (SEQ ID NO: 4)
```
MAWISLILSLLALSSGAISQAVVTQESALTTSPGETVTLTCRSSSGPVTT

SNYANWVQERPDHLFTNLIGGTNNRAPGVPARFSGSLIGDKAALTITGAQ

TEDEAIYFCALWYSNHLVFGGGTKLTVLGQPKSSPSVTLFPPSSEELETN

KATLVCTITDFYPGVVTVDWKVDGTPVTQGMETTQPSKQSNNKYMASSYL

TLTARAWERHSSYSCQVTHEGHTVEKSLSRADCS
```

Example 5—Binding Specificities of Antibodies and Immunohistochemical Studies Using Tissue Sections from Prostate Cancer Specimens Damage to DNA by oxygen free radicals gives rise to altered base structures that can lead to mutations if they are left unrepaired. Pro-mutagenic oxidative lesions such as 8-hydroxy-Gua and 8-hydroxy-Ade are known to be high in cancerous tumors but are very low in corresponding normal tissues from non-cancer individuals. Relatively less is known about the incidence of formamidopyrimidine (FAPY) derivatives of guanine and adenine. These are alternate pro-mutagenic products from oxygen free radical reactions with DNA bases resulting in a ring-opening of the purine base. Some data exists to show that FAPY derivatives, particularly FAPY-Ade, can be highly expressed in normal, non-cancer tissues and are low in the DNA from cancerous tissues. The redox status between normal and cancerous tissues appears to control the nature of the reactive oxygen species (ROS) product, particularly for the DNA base adenine. Solution chemistry of ROS reaction with adenine demonstrates that a reductive environment gives rise exclusively to FAPY-Ade whereas 8-hydroxy-Ade is the only reaction product under oxidative conditions as in cancerous tumors. This suggests the hypothesis that a progression occurs upon ROS exposure wherein normal tissues in a more reductive redox status first express primarily FAPY derivatives which increase in amount with prolonged exposure. Accumulating mutations and continued ROS exposure then may begin to shift the tissue redox status to oxidative leading to a shift in products to 8-hydroxy derivatives. With continued ROS exposure and accumulating mutations the necessary and sufficient changes for malignant conversion and tumorigenesis can then follow somewhere within that tissue while retaining the high levels of 8-hydroxy purine derivatives. Such a progression suggests FAPY residues play a significant role in early stages of carcinogenesis.

Analysis of reactive oxygen species (ROS)-induced DNA damage has been conducted in a wide variety of tissues and tumors. Studies of ROS-induced DNA base lesions present in normal, non-cancerous reduction mammoplasty human breast tissue (from 15 donors, 70 samples analyzed), breast cancer (BC) tumors and histologically normal breast tissue from BC patients (from 15 donors, 22 specimens analyzed, 7 of which both tumor and microscopically normal tissue were available) demonstrated two general types of results when the levels of FAPY- and 8-hydroxy purine bases were analyzed (9). Increased levels of 8-hydroxy purine base derivatives, particularly 8-hydroxy-Ade, were observed in both cancerous tumors and the surrounding normal tissue from cancer patients compared to normal, non-cancer specimens. In contrast, very high levels of the ring opening FAPY derivatives, especially FAPY-Ade, were found in normal tissues from non-cancer donors but were very low in all cancer derived tissues. This striking result was expressed as a statistical model with high sensitivity (91%) and specificity (97%) (P<0.0001) for classifying the origin of these tissues from either cancer or non-cancer donors. Women presently have about a 1 in 8 chance of developing breast cancer within their lifetimes and the finding of variable and sometimes substantial levels of oxidative DNA damage in normal tissues is both significant and consistent with that lifetime incidence rate. Additional study is highly warranted.

The chemical basis for this dramatic difference in expression of DNA base lesions in cancer versus non-cancer tissues may have significant implications for both cancer treatment and prevention. The chemistry of adenine offers a particularly attractive means to gain a deeper understanding of the factors influencing the nature of the products of ROS reactions with DNA and their diagnostic utility. Interestingly, analysis of ROS-induced single electron oxidations of adenine in solution has demonstrated that the redox status of the reaction controls the structure of the reaction product (6). Under oxidative conditions the transient 8-oxo-Ade radical (A8OH•) is quantitatively converted through the loss of an electron and protonation to form the 8-OH-Ade product. Alternatively, under reductive conditions through two possible mechanistic routes, the ring opening formamidopyrimidine derivative is formed as the exclusive product. The inventors propose that these inherent redox properties of adenine defined in solution will also define ROS-induced reaction products in biological specimens.

The qualitative difference in the nature of ROS-induced DNA damage observed in normal tissue from non-cancer donors and cancerous human tissue likely results from the fundamentally different redox status of cancerous or pre-cancerous tissues (oxidative) versus the more reductive environment of normal non-cancer tissues, consistent with other published reports (10-13). Because of their accumulation in cancerous tissues, 8-OH-derivatives of purines have been utilized as markers for carcinogenesis. However, redox chemistry suggests they may only be present in significant amounts in more oxidative tissues occurring in cancer and later stages of oncogenesis. Thus, FAPY-derivatives may have significant utility as a marker for mutagenesis in earlier stages of oncogenesis within histologically normal tissue and potentially offer a useful risk assessment marker for predicting (or preventing) future cancer incidence.

For these applied goals to be addressed, a convenient and reliable means for their detection and quantitation is required. To date, most studies focusing on effects of ROS on DNA have relied on chemical approaches for detection and quantitation. These include GC-MS/SIM (9,14-18) and high performance liquid chromatography-electrochemical detection (HPLC-ECD) (19-21), methodologies that require initial purification of tissue DNA with high purity for derivatization and chemical analysis; time consuming, cumbersome, and impractical for applied diagnostic or screening uses outside of a research laboratory. Information concerning the specific cell types containing elevated levels of DNA lesions is lost using these methods.

To address the need for an improved detection and quantitation method, we have focused on monoclonal antibody technology. Monoclonal antibody based detection methods have significant advantages of simplicity, flexibility, speed, and can be used to identify which cells in a tissue have most DNA damage. Monoclonal antibodies specific for 8-OH-Gua were first produced in the early 1990's and have been used in a variety of studies involving quantitative ELISA and immunohistochemical (IHC) detection in tissues. Antibodies highly specific for 8-OH-Gua and 8-OH-Ade now exist, and the present inventors have developed an antibody specific for the FAPY-Ade structure. Antibody-based methods have the advantage that they do not require initial DNA purification for their use. They can directly measure genotoxic changes present in DNA in tissues via IHC or a quantitative ELISA. The antibodies and methods of the invention provide convenience, high sensitivity and, because they are applied to the DNA, measure effects on tissues directly involved in manifesting chronic damage to an organism, including cancer.

Preparation of monoclonal antibodies with high specificity to multiple ROS-induced DNA lesions is advantageous and has been accomplished using standard monoclonal antibody methodology. Mice were immunized with KLH conjugates of either periodate oxidized 8-OH-guanosine or 8-OH-adenosine with coupling via reductive amination. Alternatively, mice were immunized with a hapten composed of 4,6-diamino(5-formamido)pyrimidine (FAPY-Ade)-containing a linker to form 4-amino, 6-aminobutyrate (5-formamido)pyrimidine with coupling to KLH by water-soluble carbodiimide coupling chemistry. Bovine Serum Albumin (BSA) conjugates with the same materials and procedures were used for monoclonal antibody screening and characterization purposes that resulted in antibodies with the proper binding specificities, as summarized briefly in the descriptions of FIGS. 26-28.

Immunohistochemical studies using tissue sections from prostate cancer (PC) specimens have been conducted using these antibodies as summarized in the descriptions of FIGS. 29A, 29B, 30A, and 30B.

8-OH-Gua is a classic marker for oxidative DNA damage in a wide variety of tumors, including prostate cancer (PC). Strong staining of cancerous cells with the 8G14 antibody in PC is consistent with that property (FIGS. 29A-29B). Interestingly, strong staining of benign epithelial cells from PC tissues demonstrates that significant DNA damage is also present in these histologically normal cells indicating DNA damage may be generalized in cancer-derived tissues, a subject of study for this work. The same pattern of staining is observed in cancerous and benign prostatic cells from PC patients using the 8A6 antibody, indicating oxidative damage to adenine is similar to that found for 8-OH-Gua (FIGS. 30A-30B).

Example 6—Immunohistochemical Analysis of Fish Tissue Using Antibodies Specific for ROS-Induced DNA Lesions Antibodies specific for three distinct yet related damaged DNA bases were tested on English sole tissue. Materials and methods utilized for the immunohistochemical analysis are described below, and results are shown in FIGS. 31A-31C.

Formalin fixed, paraffin embedded tissues from English sole were used which were obtained from multiple locations in Puget Sound, Wash. having varying water quality (clean reference waterways and those with sediments contaminated with PCBs). IHC analysis with the following antibodies was conducted.

TABLE 4

| Antibody | Specificity | Murine Isotype |
| --- | --- | --- |
| 8G14 | 8-OH-Gua | IgM |
| 8A9 | 8-OH-Ade | IgG1 |
| FA5 | FAPY-Ade | IgG3 |

Sections were cut and processed according to standard immunofluorescence staining methods as follows.
1. Cut paraffin sections at 5-6 microns and mount on charged slides.
2. Deparaffinize with treatment with xylenes and dehydrated through graded alcohols, rehydrated, and pretreated by steam in citrate buffer, pH 6.2.
3. Treat slides with RNase (100 µg/ml) in Tris buffer (pH 7.5; 10 mM Trizma base, 1 mM EDTA, and 0.4 M NaCl) at 37° C. for 1 hour, wash 1× with PBS.
4. Treat slides with Proteinase K (10 µg/ml) at room temperature for 7 minutes, rinse with PBS.
5. Denature DNA in 4N HCl for 7 minutes at room temperature.
6. Block endogenous peroxidase activity in $H_2O_2$/MeOH (DAKO #K0673) for 10 minutes at room temperature.
7. Rinse in running tap water for 2 minutes, then wash with PBS twice, 2 minutes each.
8. Add primary antibody with appropriate dilution in a commercial antibody diluent (DAKO #S0809) to the test slide. Add antibody diluent buffer to the negative control slide. Be sure that the section is completely covered with solution (200-300 µl required). Incubate 45 minutes at room temperature.
9. Drain off antibody and rinse twice with PBS, 2 minutes each.

10. Add appropriately diluted FITC-labeled secondary antibody (rabbit anti-mouse IgM for the 8G14 stained sections and rabbit anti-mouse IgG for sections stained with 8A9 and FA5) (Sigma) to appropriate slides. Incubate 20 minutes at room temperature.
11. Drain off secondary antibody and rinse twice with PBS, 2 minutes each, coverslip for viewing.

These DNA lesions are caused by single electron (free radical) oxidation reactions with either adenine or guanine. The staining profile for each antibody is similar and indicative of focal expression of cells containing altered DNA bases. Such focal expression of markers associated with precancerous conditions is frequently observed in animal tissues after exposures to toxicants. These results demonstrate consistent staining properties of the antibodies and that the antibody FA5 is well suited for detection of the FAPY-A lesion in tissues by immunohistochemistry.

Positive staining in histologically normal tissue in fish inhabiting contaminated waterways is indicative of DNA damage resulting from such exposure. In contrast, immunohistochemistry of tissues from animals inhabiting clean reference waterways demonstrates weak or no staining with the same panel of antibodies. This profile (high expression in exposed animals, and weak or negative expression in control unexposed animals) is consistent with results obtained using chemical detection methods. Thus, immunohistochemistry using the FA5 antibody as well as other antibodies specific for other DNA base lesions is useful to characterize the amount of pro-mutagenic DNA base damage present in an organism. This information can be used to assess a potential risk for future cancer incidence in an organism given the known mutagenic potential of oxidative DNA base lesions such as 8-hydroxy-adenine, 8-hydroxy-guanine and FAPY-adenine. Such a risk analysis would involve an immunochemical/immunohistochemical quantitation of oxidized DNA bases. This can include determining the expression ratio of the amount of one or more 8-hydroxy-purine products to the amount of one or more FAPY-purine products. The formation of 8-hydroxy-purine products is favored under oxidative conditions in tissues, and the formation of ring-opening FAPY-purine products is favored under more reducing conditions. Generally, cancerous or precancerous tissues have a more oxidative redox status compared to a more reductive redox status of normal tissues. Thus, the amount and identity of oxidative DNA base lesions can provide useful information related to the future risk of an organism developing cancer. Altering the tissue redox status using one or more antioxidants can reduce the amount of DNA damage in an organism's tissues.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Miller E C, Miller J A. (1981) Mechanisms of chemical carcinogenesis. *Cancer*, 47(suppl 5):1055-1064.
2. Weinstein I B. (1982) Carcinogenesis as a multistage process—experimental evidence. *IARC Sci Publ.*, 39:9-25.
3. Slaga T J, Fischer S M, Weeks C E, Klein-Szanto A J, Reiners J. (1982) Studies on the mechanisms involved in multistage carcinogenesis in mouse skin. *J Cell Biochem*, 18:99-119.
4. Reid T M, Fry M, Loeb L A. (1991) Endogenous mutations and cancer. *Princess Takamatsu Symp.*, 22:221-229.
5. Cheng K C, Cahill D S, Kasai H, Nishimura S, Loeb L A. (1992) 8-Hydroxyguanine, an abundant form of oxidative DNA damage, causes G - - - T and A - - - C substitutions. *J Biol Chem.*, 267:166-172.
6. Steenken, S. (1989) Purine bases, nucleosides and nucleotides: aqueous solution redox chemistry and transformation of their radical cations e- and OH adducts. *Chem. Rev.*, 89:503-520.
7. Kalam M A, Haraguchi K, Chandani S, Loechler E L, Moriya M, Greenberg M M, Basu A K. (2006) Genetic effects of oxidative DNA damages: comparative mutagenesis of the imidazole ring-opened formamidopyrimidines (Fapy lesions) and 8-oxo-purines in simian kidney cells. *Nucleic Acids Res.*, 34:2305-2315.
8. Smela M E, Hamm M L, Henderson P T, Harris C M, Harris T M, Essigmann J M. (2002) The aflatoxin B(1) formamidopyrimidine adduct plays a major role in causing the types of mutations observed in human hepatocellular carcinoma. *Proc Natl Acad Sci USA*, 99:6655-6660.
9. Malins, D. C., Holmes, E. H., Polissar, N. L., and Gunselman, S. J. (1993) The etiology of breast cancer: characteristic alterations in hydroxyl radical-induced DNA base lesions during oncogenesis with potential for evaluating incidence risk. *Cancer*, 71:3036-3043.
10. Acharya, A., Das, I., Chandhok, D., and Saha, T. (2010) Redox regulation in cancer: A double-edged sword with therapeutic potential. *Oxidative Medicine and Cellular Longevity*, 3:23-34.
11. Circu M L, Aw T Y. (2010) Reactive oxygen species, cellular redox systems, and apoptosis. *Free Radic Biol Med.*, 48:749-762.
12. Aw T. (2003) Cellular redox: a modulator of intestinal epithelial cell proliferation. *News Physiol Sci.*, 18:201-204.
13. Aw, T. (1999) Molecular and cellular responses to oxidative stress and changes in oxidation-reduction imbalance in the intestine. *Am J Clin Nutr.*, 70:557-565.
14. Dizdaroglu, M. (1985) Application of capillary gas chromatography-mass spectrometry to chemical characterization of radiation-induced base damage of DNA: implications for assessing DNA repair processes. *Anal. Biochem.*, 144:593-603.
15. Dizdaroglu M, Gajewski E. (1990) Selected-ion mass spectrometry: assays of oxidative DNA damage. *Methods Enzymol.*, 186:530-544.
16. Djuric Z, Luongo D A, Harper D A. (1991) Quantitation of 5-(hydroxymethyl)uracil in DNA by gas chromatography with mass spectral detection. *Chem Res Toxicol.*, 4:687-691.
17. Dizdaroglu, M. (1984) The use of capillary gas chromatography-mass spectrometry for identification of radiation-induced DNA base damage and DNA base-amino acid cross-links. *J. Chromatog.*, 295:103-121.

18. Aruoma, O. I., Halliwell, B., and Dizdaroglu, M. (1989) Damage to the bases in DNA induced by hydrogen peroxide and ferric ion chelates. *J. Biol. Chem.,* 264: 13024-13028.
19. Floyd R A, West M S, Eneff K L, Hogsett W E, Tingey D T. (1988) Hydroxyl free radical mediated formation of 8-hydroxyguanine in isolated DNA. *Arch Biochem Biophys.,* 262:266-272.
20. Shigenaga M K, Ames B N. (1991) Assays for 8-hydroxy-2'-deoxyguanosine: a biomarker of in vivo oxidative DNA damage. *Free Radic Biol Med.,* 10:211-216.
21. Loft S, Fischer-Nielsen A, Jeding I B, Vistisen K, Poulsen H E. (1993) 8-Hydroxydeoxyguanosine as a urinary biomarker of oxidative DNA damage. *J Toxicol Environ Health,* 40:391-404.
22. Cho et al. (1990) *Chem. Res. Toxicol.,* 3:445-452.
23. Cho and Evans (1991) *Nucleic Acids Research,* 19(5): 1041-1047.
24. Galfre and Milstein (1981), Methods in Enzymology, Vol. 73, Immunochemical Techniques, Part B.

We claim:

1. An antibody, or antigen-binding fragment thereof, having specific binding affinity for 4,6-diamino-5-(formamido)pyrimidine (FAPY-adenine), wherein the antibody or antigen-binding fragment specifically binds to an epitope on the base portion of FAPY-adenine and does not significantly bind to 8-hydroxy-adenine, 8-hydroxy-guanine, adenosine, cytosine, uracil, and guanine.

2. The antibody or antigen-binding fragment of claim 1, wherein the antibody comprises:
   (a) an immunoglobulin heavy chain variable region ($V_H$) comprising a CDR1 sequence at least 80% identical to amino acids 50 to 54 of SEQ ID NO:2, a CDR2 sequence at least 80% identical to amino acids 69 to 85 of SEQ ID NO:2, and a CDR3 sequence at least 80% identical to amino acids 118 to 126 of SEQ ID NO:2; and
   (b) an immunoglobulin light chain variable region ($V_L$) comprising a CDR1 sequence at least 80% identical to amino acids 42 to 55 of SEQ ID NO:4, a CDR2 sequence at least 80% identical to amino acids 71 to 77 of SEQ ID NO:4, and a CDR3 sequence at least 80% identical to amino acids 110 to 118 of SEQ ID NO:4.

3. A hybridoma secreting a monoclonal antibody having specific binding affinity for 4,6-diamino-5-(formamido)pyrimidine (FAPY-adenine), wherein the hybridoma produces a monoclonal antibody that specifically binds to an epitope on the base portion of FAPY-adenine and does not significantly bind to 8-hydroxy-adenine, 8-hydroxy-guanine, adenosine, cytosine, uracil, and guanine.

4. The hybridoma of claim 3, wherein the monoclonal antibody comprises:
   (a) an immunoglobulin heavy chain variable region ($V_H$) comprising a CDR1 sequence at least 80% identical to amino acids 50 to 54 of SEQ ID NO:2, a CDR2 sequence at least 80% identical to amino acids 69 to 85 of SEQ ID NO:2, and a CDR3 sequence at least 80% identical to amino acids 118 to 126 of SEQ ID NO:2; and
   (b) an immunoglobulin light chain variable region ($V_L$) comprising a CDR1 sequence at least 80% identical to amino acids 42 to 55 of SEQ ID NO:4, a CDR2 sequence at least 80% identical to amino acids 71 to 77 of SEQ ID NO:4, and a CDR3 sequence at least 80% identical to amino acids 110 to 118 of SEQ ID NO:4.

5. A method for determining the presence or amount of FAPY-adenine in a biological specimen, comprising the steps of: (a) contacting the specimen with the antibody or antigen-binding fragment of claim 1, or an immunoconjugate, to form a complex of (i) the antibody, antigen-binding fragment thereof, or immunoconjugate, and (ii) FAPY-adenine; and (b) determining the presence or amount of the complex formed as an indication of the presence or amount of FAPY-adenine in the specimen, wherein the immunoconjugate comprises the antibody, or antigen-binding fragment thereof, covalently coupled to a detectable moiety.

6. A method for determining exposure of a human or animal subject to a toxicant associated with elevated levels of FAPY-adenine in a biological specimen obtained from the human or animal subject, comprising the steps of:
  (a) contacting the biological specimen obtained from the human or animal subject with a first amount of the antibody or antigen-binding fragment of claim 1, or an immunoconjugate, to form a complex of: (i) the antibody, antigen-binding fragment thereof, or immunoconjugate, and (ii) FAPY-adenine, wherein the immunoconjugate comprises the antibody, or antigen-binding fragment thereof, covalently coupled to a detectable moiety;
  (b) determining the amount of complex formed in step (a); and
  (c) comparing the amount of complex determined in step (b) with a range of FAPY-adenine concentrations found in human or animal specimens that have not been exposed to the toxicant associated with elevated levels of FAPY-adenine.

7. A method for determining the amount of FAPY-adenine in a biological specimen, comprising:
  a. contacting the antibody or antigen-binding fragment of claim 1, or an immunoconjugate, with the specimen to form a complex between: (i) the antibody, antigen-binding fragment thereof, or immunoconjugate, and (ii) FAPY-adenine in the specimen, wherein the immunoconjugate comprises the antibody, or antigen-binding fragment thereof, covalently coupled to a detectable moiety;
  b. quantitating the amount of complex formed; and
  c. comparing the amount of complex formed to the amount of the antibody, antigen-binding fragment thereof, or immunoconjugate that complexes with a known amount of FAPY-adenine.

8. A method for determining the presence or amount of an epitope which comprises FAPY-adenine in a biological specimen comprising the steps of:
  a. contacting the specimen with the antibody or antigen-binding fragment of claim 1, or an immunoconjugate, to form a complex of: (i) the antibody, antigen-binding fragment thereof, or immunoconjugate, and (ii) the epitope which comprises FAPY-adenine, wherein the antibody and antigen-binding fragment thereof have specific binding affinity for FAPY-adenine, wherein the immunoconjugate comprises the antibody, or antigen-binding fragment thereof, covalently coupled to a detectable moiety; and
  b. determining the presence or amount of complex formed as a measure of the presence or amount of the epitope which comprises FAPY-adenine in the specimen.

9. The hybridoma of claim 3, wherein the monoclonal antibody comprises:
  (a) an immunoglobulin heavy chain variable region ($V_H$) comprising a CDR1 sequence comprising amino acids 50 to 54 of SEQ ID NO:2, a CDR2 sequence comprising amino acids 69 to 85 of SEQ ID NO:2, and a CDR3 sequence comprising amino acids 118 to 126 of SEQ ID NO:2; and
  (b) an immunoglobulin light chain variable region ($V_L$) comprising a CDR1 sequence comprising amino acids 42 to 55 of SEQ ID NO:4, a CDR2 sequence comprising amino acids 71 to 77 of SEQ ID NO:4, and a CDR3 sequence comprising amino acids 110 to 118 of SEQ ID NO:4.

10. The antibody or antigen-binding fragment of claim 1, wherein the antibody comprises:
  (a) an immunoglobulin heavy chain variable region ($V_H$) comprising a CDR1 sequence comprising amino acids 50 to 54 of SEQ ID NO:2, a CDR2 sequence comprising amino acids 69 to 85 of SEQ ID NO:2, and a CDR3 sequence comprising amino acids 118 to 126 of SEQ ID NO:2; and
  (b) an immunoglobulin light chain variable region ($V_L$) comprising a CDR1 sequence comprising amino acids 42 to 55 of SEQ ID NO:4, a CDR2 sequence comprising amino acids 71 to 77 of SEQ ID NO:4, and a CDR3 sequence comprising amino acids 110 to 118 of SEQ ID NO:4.

11. The antibody or antigen-binding fragment of claim 1, wherein the antibody or antigen-binding fragment thereof is the antibody.

12. The antibody or antigen-binding fragment of claim 1, wherein the antibody or antigen-binding fragment thereof is the antigen-binding fragment.

13. The antibody or antigen-binding fragment of claim 12, wherein the antigen-binding fragment thereof is selected from the group consisting of a Fab fragment, an F(ab')$_2$ fragment, and an FIT fragment.

14. The antibody or antigen-binding fragment of claim 1, wherein the antibody is an IgG or IgM molecule.

15. The antibody or antigen-binding fragment of claim 1, wherein the antibody is a humanized antibody.

16. The antibody or antigen-binding fragment of claim 1, wherein the antibody is a monoclonal antibody.

17. The antibody or antigen binding fragment of claim 16, wherein the monoclonal antibody is produced by the hybridoma deposited under ATCC Accession Number PTA-121431.

18. A hybridoma deposited under ATCC Accession Number PTA-121431.

19. A monoclonal antibody produced by the hybridoma deposited under ATCC Accession Number PTA-121431.

20. The antibody or antigen-binding fragment of claim 1, wherein the FAPY-adenine is present in a nucleic acid.

* * * * *

UNITED STATES PATENT AND TRADEMARK OFFICE
CERTIFICATE OF CORRECTION

PATENT NO. : 9,884,920 B2  
APPLICATION NO. : 15/289783  
DATED : February 6, 2018  
INVENTOR(S) : Eric Holmes and Gary Ostrander Page 1 of 1

It is certified that error appears in the above-identified patent and that said Letters Patent is hereby corrected as shown below:

In the Specification

Column 43,
Line 21, "(MA)" should read --(RIA)--.

Signed and Sealed this
Twenty-fifth Day of September, 2018

Andrei Iancu
*Director of the United States Patent and Trademark Office*